US009783560B2

(12) United States Patent
Benson et al.

(10) Patent No.: US 9,783,560 B2
(45) Date of Patent: Oct. 10, 2017

(54) REAGENTS USEFUL FOR SYNTHESIZING RHODAMINE-LABELED OLIGONUCLEOTIDES

(71) Applicant: APPLIED BIOSYSTEMS, LLC, Carlsbad, CA (US)

(72) Inventors: Scott C. Benson, Alameda, CA (US); Ruiming N. Zou, Foster City, CA (US); Krishna G. Upadhya, Union City, CA (US); Paul M. Kenney, Sunnyvale, CA (US); Jonathan M. Cassel, Half Moon Bay, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 39 days.

(21) Appl. No.: 14/702,499

(22) Filed: May 1, 2015

(65) Prior Publication Data

US 2015/0232494 A1 Aug. 20, 2015

Related U.S. Application Data

(62) Division of application No. 11/695,548, filed on Apr. 2, 2007, now Pat. No. 9,040,674.

(60) Provisional application No. 60/787,777, filed on Mar. 31, 2006.

(51) Int. Cl.
  *C07D 311/96* (2006.01)
  *C07H 19/04* (2006.01)
  *C07F 9/6561* (2006.01)
  *C07H 21/04* (2006.01)

(52) U.S. Cl.
  CPC .......... *C07F 9/6561* (2013.01); *C07D 311/96* (2013.01); *C07H 19/04* (2013.01); *C07H 21/04* (2013.01)

(58) Field of Classification Search
  CPC ...... C07F 9/6561; C07D 311/96; C07H 19/04
  See application file for complete search history.

(56) References Cited

U.S. PATENT DOCUMENTS

| 4,557,862 A | 12/1985 | Mangel et al. |
| 4,965,349 A | 10/1990 | Woo et al. |
| 5,231,191 A | 7/1993 | Woo et al. |
| 5,942,610 A | 8/1999 | Nelson et al. |
| 6,080,852 A | 6/2000 | Lee et al. |
| 6,255,476 B1 | 7/2001 | Vinayak et al. |
| 6,544,744 B1 | 4/2003 | Mathies et al. |
| 6,583,168 B1 | 6/2003 | Menchen et al. |
| 6,750,357 B1 | 6/2004 | Chiarello et al. |
| 2004/0014131 A1 | 1/2004 | Benson et al. |

FOREIGN PATENT DOCUMENTS

| WO | WO-00/50432 | 8/2000 |
| WO | WO-00/75236 | 12/2000 |
| WO | WO-03/002715 | 1/2003 |
| WO | WO-2005/007678 | 1/2005 |
| WO | WO-2006/020947 | 2/2006 |

OTHER PUBLICATIONS

Berry & Associates Products Catalog, (Products FF 6015, FF 6030, FF 6020, FF 6050, FF 6040, FF 6070, FF 6060, FF 6080, FF 6090, FF 6100, FT 6220 and FT 6230), 2002, pp. 66-68 and 101.
Berry & Associates Products Catalog Supplement, (Products BA 0054, BA 0147, BA 0202, BA 0107, BA 0139, BA 1022 and BA 0130), 2005, pp. 38-40.
Glen Research Handbook, 1999, pp. 36-37, 42-53, 62-69 and 75.
Glen Research Products Catalog, (note especially pp. 80 and 77-79), 2006, pp. 77-89.
07759970.2, Extended European Search Report mailed Sep. 22, 2010.
Ju, Jingyue et al., "Fluorescence energy transfer dye-labeled primers for DNA sequencing and analysis", *Proc. Natl. Acad. Sci*, vol. 92(10), May 1995, 4347-4350.
Kutyavin, et al., "3'-Minor groove binder-DNA probes increase sequence specificity at PCR extension temperatures", *Nucleic Acids Research*, vol. 28, No. 2, Jan. 15, 2000, 655-661.
Lyttle, et al., "A Tetramethyl Rhodamine (Tamra) Phosphoramidite Facilitates Solid-Phase-Supported Synthesis of 5'-Tamra DNA", *Journal of Organic Chemistry*, vol. 65, No. 26, 2000, pp. 9033-9038.
Mullah, Bashar et al., "Automated Synthesis of Double Dye-Labeled Oligonucleotides using Tetramethylrhodamine (TAMRA) Solid Supports", *Tetrahedron Letters*, vol. 38, No. 33, 1997, pp. 5751-5754.
PCT/US2007/065798, International Preliminary Report on Patentability mailed, Sep. 30, 2008.
PCT/US2007/065798, International Search Report mailed, Nov. 13, 2007.
Sun, Wei-Chuan et al., "Synthesis of Fluorinated Fluoresceins", *Journal of Organic Chemistry*, vol. 62, No. 19, 1997, pp. 6469-6475.
Vinayak, Ravi, "A Convenient, Solid-Phase Coupling of Rhodamine Dye Acids to 5' Amino-Oligonucleotides", *Tetrahedron Letters*, 40, 1999, Jul. 1999, 7611-7613.

*Primary Examiner* — Jonathan S Lau
(74) *Attorney, Agent, or Firm* — McNeill Baur PLLC

(57) ABSTRACT

The present disclosure provides reagents that can be used to label synthetic oligonucleotides with rhodamine dyes or dye networks that contain rhodamine dyes.

16 Claims, 14 Drawing Sheets

REAGENTS USEFUL FOR SYNTHESIZING RHODAMINE-LABELED OLIGONUCLEOTIDES

1. CROSS REFERENCE TO RELATED APPLICATIONS

This application is a divisional of U.S. non-provisional application Ser. No. 11/695,548, filed Apr. 2, 2007, which claims benefit under 35 U.S.C. §119(e) to provisional application No. 60/787,777, filed Mar. 31, 2006, which disclosures are herein incorporated by reference in their entirety.

2. BACKGROUND

The use of fluorescent dyes as detection labels has found widespread use in molecular biology, cell biology and molecular genetics. For example, the use of fluorescently-labeled oligonucleotides is now widespread in a variety of different assays, including polynucleotide sequencing, fluorescence in situ hybridization (FISH), hybridization assays on nucleic acid arrays, fluorescence polarization studies, and nucleic acid amplification assays, including polymerase chain amplification assays carried out with fluorescent probes and/or primers.

Some fluorescent labels can be attached to nascent or completed oligonucleotide chains synthesized in situ using fluorescent phosphoramidite reagents. For example, fluorescein phosphoramidite reagents are available commercially (see, e.g., 2006 product catalog of Glen Research Corporation, Sterling, Va.). In such reagents, the 3'- and 6'-exocyclic oxygen atoms of the fluorescein ring are protected with pivaloyl groups to prevent side reactions. Modification of the fluorescien ring with these groups also holds the carboxylate group at the 3-position in the closed, spiro lactone form, preventing proton donation from the carboxylate to the phosphoramidite group, which would convert this phosphoramidite group into a good leaving group, leading to decomposition of the reagent. The fluorescein ring is also stable to the conditions used to oxidize the nascent oligonucleotide and to treatment with aqueous ammonium, the standard method by which the nucleobase protecting groups are removed and the synthetic oligonucleotide is cleaved from the synthesis resin.

Unfortunately, many rhodamine dyes are susceptible to chemical modification when treated with the reagents commonly employed to oxidize and deprotect/cleave synthetic oligonucleotides negatively impacting their fluorescent properties. As a consequence, rhodamine dyes are commonly attached to oligonucleotides following synthesis, deprotection and cleavage from the synthesis resin. This adds additional steps and manual labor, resulting in greater cost and inconvenience in the overall synthesis of rhodamine-labeled oligonucleotides.

Owing to these and other limitations, there are currently only two rhodamine dyes that are commercially available as phosphoramidite reagents: tetramethyl rhodamine ("TAMRA") and rhodamine X ("ROX"). Additional reagents that permit labeling of oligonucleotides with myriad different rhodamine dyes during solid phase chemical synthesis would be desirable.

3. SUMMARY

In one aspect, the present disclosure provides reagents useful for labeling synthetic oligonucleotides with labels comprising rhodamine dyes that fluoresce when irradiated with incident light of an appropriate wavelength. The labels can comprise a single rhodamine dye, or they can comprise a dye network in which at least one of the dyes is a rhodamine dye. The reagents can be used to label synthetic oligonucleotides with rhodamine dye-containing labels directly during the step-wise synthesis of the oligonucleotides, thereby reducing the manipulation steps necessary to obtain oligonucleotides that are labeled with rhodamine dyes. Moreover, because the labels are attached to the oligonucleotide directly during step-wise synthesis, HPLC separation of uncoupled label from the labeled oligonucleotide, which is necessary when using currently available post-synthesis rhodamine labeling reagents such as rhodamine NHS esters, is unnecessary.

The reagents can be used to label an oligonucleotide at its 3'-terminus, at its 5-terminus, and/or at one or more internal positions. The resultant label can be attached to the terminal hydroxyl(s) of the oligonucleotide, to one or more nucleobases comprising the oligonucleotide, or it can be disposed between two nucleotides comprising the oligonucleotide chain. Thus, the reagents can take the form of non-nucleosidic synthesis reagents (see, e.g., FIGS. 3 and 5), nucleosidic synthesis reagents (see, e.g., FIGS. 4 and 6), non-nucleosidic solid supports (see, e.g., FIG. 7) and/or nucleosidic solid supports (see, e.g., FIG. 8).

The synthesis reagents generally comprise a label moiety, a phosphate ester precursor ("PEP") group and an optional linker linking the phosphate ester precursor group to the label moiety. The phosphate ester precursor group generally comprises a functional group that, when used in the step-wise synthesis of oligonucleotides, ultimately yields, after optional deprotection and/or oxidation, the internucleotide phosphate ester linkage. Several types of chemistries and functional groups suitable for synthesizing internucleotide phosphate ester linkages are known in the art, and include, by way of example and not limitation, phosphite triester chemistry, which utilizes phosphoramidite PEP groups (see, e.g., Letsinger et al., 1969, J. Am. Chem. Soc. 91:3350-3355; Letsinger et al., 1975, J. Am. Chem. Soc. 97:3278; Matteucci & Caruthers, 1981, J. Am. Chem. Soc. 103:3185; Beaucage & Caruthers, 1981, Tetrahedron Lett. 22:1859), phosphotriester chemistry, which utilizes 2-chlorophenyl- or 2,5-dichlorophenyl-phosphate PEP groups (see, e.g., Sproat & Gait, "Solid Phase Synthesis of Oligonucleotides by the Phosphotriester Method," In: *Oligonucleotide Synthesis, A Practical Approach*, Gait, Ed., 1984, IRL Press, pages 83-115) and H-phosphonate chemistry, which utilizes H-phosphonate PEP groups (see, e.g., Garegg et al., 1985, Chem. Scr. 25:280-282; Garegg et al., 1986, Tet. Lett. 27:4051-4054; Garegg et al. 1986, Tet. Lett. 27:4055-4058; Garegg et al., 1986, Chem. Scr. 26:59-62; Froehler & Matteucci, 1986, Tet. Lett. 27:469-472; Froehler et al., 1986, Nucl. Acid Res. 14:5399-5407). All of these various PEP groups, as well as later-discovered PEP groups, can comprise the phosphate ester precursor group of the synthesis reagents described herein. The identity of the PEP group is not critical for success, and will depend upon the desired chemistry for synthesizing the labeled oligonucleotides. In some embodiments, the phosphate ester precursor group comprises a phosphoramidite group.

The optional linker linking the label moiety and phosphate ester precursor group can comprise virtually any combination of atoms or functional groups stable to the synthetic conditions used for the synthesis of the labeled oligonucleotides, and can be linear, branched, or cyclic in structure, or can include combinations of linear, branched and/or cyclic structures. The linker can be designed to have specified properties, such as the ability to be cleaved under desired conditions.

The synthesis reagents may optionally further comprise one or more synthesis handles to which nucleosides or other groups or moieties can be attached. The synthesis handles can include protecting groups that can be selectively removed during the step-wise synthesis of the labeled oligonucleotide, permitting attachment of moieties to the synthetic oligonucleotide prior to cleavage from the resin, or, alternatively, the synthesis handles can include protecting groups that are stable to the conditions used to deprotect and/or cleave the synthesized oligonucleotide from the synthesis resin, permitting attachment of moieties to the synthetic labeled oligonucleotide following synthesis, deprotection and cleavage from the synthesis resin. The synthesis handles comprising a synthesis reagent that includes more than one synthesis handle may be the same or different.

In some embodiments, the synthesis reagents comprise a single optional synthesis handle that comprises a protected hydroxyl of the formula $-OR^e$, where $R^e$ represents an acid-labile protecting group.

The synthesis handle can be linked to the label moiety, or it can be included in the optional linker linking the label moiety and phosphate ester precursor group. Embodiments in which a synthesis handle of the formula $-OR^e$ is included in the optional linker can be non-nucleosidic in nature or nucleosidic in nature, in which latter case the linker comprises a nucleoside and the synthesis handle is provided by a hydroxyl group on the sugar moiety of a nucleoside, typically the 5'-hydroxyl of the nucleoside sugar moiety. Specific, non-limiting embodiments of non-nucleosidic synthesis reagents in which the linker includes a synthesis handle are illustrated in FIG. 5. Specific, non-limiting embodiments of nucleosidic synthesis reagents in which the linker includes a synthesis handle are illustrated in FIG. 6.

The solid support reagents generally comprise a label moiety, a synthesis handle of the formula $-OR^e$ where $R^e$ is as defined above, a solid support and a linker linking the label moiety and the synthesis handle to the solid support. The synthesis handle provides a group to which nucleoside monomer reagents can be coupled. The solid support reagents can optionally include one or more additional synthesis handles, which can be the same or different.

A wide variety of materials suitable for use as solid supports in the solid-phase synthesis of oligonucleotides that either include appropriate functional groups, or that can be derivatized to include appropriate functional groups, are known in the art, and include, by way of example and not limitation, controlled pore glass (CPG), polystyrene, and various graft co-polymers. All of these various materials are suitable for use as the solid support in the solid support reagents described herein.

The shape of the solid support is not critical. Virtually any shape can be utilized. For example, the solid support can be in the form of spherical or irregularly shaped beads, cubes, rectangles, cylinders, cylindrical tubes, or even sheets. The solid support may be porous or non-porous. In some embodiments, the solid support is a CPG or polystyrene bead.

The linker linking the label moiety and synthesis handle to the solid support can comprise virtually any combination of atoms or functional groups stable to the synthesis conditions typically used for the solid phase synthesis of oligonucleotides, and can be linear, branched, or cyclic in structure, or can include combinations of linear, branched and/or cyclic structures. The linker can be designed to have specified properties, such as the ability to be cleaved under desired conditions. In some embodiments, the linker includes a linkage that can be cleaved under specified conditions to release the solid support from the remainder of the reagent. For example, the linker can include linkages that are stable under oligonucleotides synthesis conditions and labile to the conditions used to deprotect the synthesized oligonucleotides (for example, incubation in ammonium hydroxide at 55° C. or room temperature). Such specifically cleavable linkages are well-known in the art, and include by way of example and not limitation, esters, carbonate esters, diisopropylsiloxy ethers, modified phosphate esters, etc.

As described above for the synthesis reagents, the linker of the solid support reagents can include the synthesis handle, and can be nucleosidic or non-nucleosidic in nature. Specific, non-limiting embodiments of non-nucleosidic solid support reagents are illustrated in FIG. 7. Specific, non-limiting embodiments of nucleosidic solid support reagents are illustrated in FIG. 8.

The label moiety of the synthesis and solid support reagents described herein comprises a rhodamine dye. The exocyclic nitrogen atoms at the 3'- and 6'-positions of the rhodamine dye are either unsubstituted or mono-substituted such they are included in a primary or secondary amine, and are further substituted with a protecting group (unprotected rhodamine dyes having primary or secondary amine groups at their 3'- and 6'-positions are referred to herein as "NH-rhodamines" and rhodamine dyes having protecting groups at their 3'- and 6'-positions are referred to herein as "N-protected NH-rhodamines").

The protecting group can be virtually any specifically removable group that is stable to the synthesis conditions that will be used to synthesize the labeled oligonucleotide, for example the phosphite triester chemistry conditions typically used for solid-phase synthesis of oligonucleotides. It has been discovered that protecting the 3'- and 6'-secondary or primary amines of NH-rhodamines with groups that form amides, such as, for example carboxamides, sulfonamides, phosphoramides, etc., permits the N-protected NH-rhodamine to exist in the closed, lactone form, thereby permitting the rhodamines to be used in the step-wise synthesis of oligonucleotides to conveniently synthesize oligonucleotides including rhodamine dyes without the need for post-synthesis manipulation or purification. As demonstrated in the working examples, phosphoramidite reagents including such N-protected NH-rhodamines are soluble in the solvents commonly employed in the step-wise synthesis of oligonucleotides, are stable to multiple rounds of DMT deprotection, coupling, oxidation and capping, and also to treatment with concentrated ammonium hydroxide, conditions which are commonly used to deprotect any exocyclic amine protecting groups and cleave the synthetic oligonucleotide from the synthesis resin.

The protecting groups can be labile, and thus removable, under the conditions used to remove the nucleobase protecting groups of the synthesized labeled oligonucleotide, or, alternatively, the protecting groups can be stable to these conditions and labile to other conditions. In most instances, it will likely be desirable to utilize protecting groups that are labile to the conditions used to remove the nucleobase protecting groups of the synthesized labeled oligonucleotide and/or to cleave the labeled synthetic oligonucleotide from the synthesis resin.

In some embodiments, the protecting groups are acyl groups of the formula $-C(O)R^{10}$, where $R^{10}$ is selected from lower alkyl, methyl, $-CX_3$, $-CHX_2$, $-CH_2X$, $-CH_2-OR^b$ and phenyl optionally mono-substituted with a lower alkyl, methyl, X, —OR$^b$, cyano or nitro group, where R$^b$ is selected from lower alkyl, pyridyl and phenyl and each X is a halo group, typically fluoro, chloro or bromo. In a specific, non-limiting embodiment, R$^{10}$ is t-butyl or trifluoromethyl.

The label moiety may further comprise additional protected fluorophores, such that the N-protected NH-rhodamine dye is a member of a larger, energy-transfer dye network. Such energy-transfer dye networks are well-known in the art, and include combinations of fluorophores whose spectral properties are matched, or whose relative distances to one another are adjusted, so that one fluorophore in the network, when excited with incident irradiation of an appropriate wavelength, transfers its excitation energy to another fluorophore in the network, which in turn transfers its excitation energy to yet another fluorophore in the network, and so forth, resulting in fluorescence by the ultimate acceptor fluorophore in the network. Such networks give rise to labels having long Stokes shifts. In such networks, fluorophores that transfer, or donate, their excitation to another fluorophore in the network are referred to as "donors." Fluorophore that receive, or accept, excitation energy from another fluorophore and fluorescein reagents thereto are referred to as "acceptors." In dye networks containing only two dyes, one dye typically acts as the donor and the other as the acceptor. In dye networks containing three or more different dyes, at least one dye acts as both a donor and acceptor.

Energy transfer dye networks containing two, three, four, or even more dyes are well-known in the art (see, e.g., US 2006/057565). Any of the dyes used in these networks that can be suitably protected for use in the solid phase synthesis oligonucleotides can be included in the label moieties described herein.

In some embodiments of the synthesis and solid support reagents described herein, the label moiety further comprises a suitably protected donor for the N-protected NH-rhodamine. When deprotected, such donors transfer their excitation energy to the NH-rhodamine such that the NH-rhodamine emits fluorescence upon excitation of the donor.

In some embodiments of the synthesis and solid support reagents described herein, the label moiety further comprises a suitably protected acceptor for the N-protected NH-rhodamine. When deprotected, such acceptors accept excitation energy from the donor NH-rhodamine such that the acceptor fluoresces upon excitation of the donor NH-rhodamine.

The identities of the donor or acceptor will depend upon the identity of the NH-rhodamine comprising the label moiety. Examples of fluorophores capable of acting as a donor for a wide variety of rhodamine dyes are well-known in the art. Non-limiting examples of such donors include xanthene dyes (such as, for example) fluoresceins, rhodamines and rhodols), pyrene dyes, coumarin dyes (for example hydroxy and amino coumarins), cyanine dyes, phthalocyanine dyes, and lanthenide complexes. Examples of fluorophores capable of acting as acceptors for rhodamine dyes are also well-known in the art. Non-limiting examples of such acceptors include rhodamines dyes and cyanines dyes. Any of these dyes that can be suitably protected for use under the conditions used to synthesize oligonucleotides, such as the phosphite triester chemistry conditions typically used for the solid-phase synthesis of oligonucleotides, can be used as the donor or acceptor in the synthesis and solid support reagents described herein.

The mechanism by which energy is transferred from a donor to the acceptor is not critical. All that is necessary for such donor-acceptor pairs to be operable is that the acceptor fluoresce in response to excitation of the donor.

The label moiety may also include acceptors that are non-fluorescent. Such non-fluorescent acceptors can be used to quench, either in whole or in part, the fluorescence of the NH-rhodamine or other fluorescent dye(s) comprising the label moiety. Examples of such non-fluorescent moieties that can act as quenchers for rhodamine dyes such as the NH-rhodamines described herein include, but are not limited to, dabcyl, the various non-fluorescent quenchers described in WO 01/86001 and the various non-fluorescent quenchers described in US 2005/0164225, the disclosures of which are incorporated herein by reference.

In some embodiments, the label moiety further comprises a donor dye that in turn comprises an N-protected NH-rhodamine dye as described herein or a fluorescein dye in which the exocyclic 3'- and 6'-oxygen atoms are protected with protecting groups that are stable to oligonucleotide synthesis conditions, such as the phosphite triester chemistry conditions typically used for the solid phase synthesis of oligonuclotides, and labile to the conditions used to deprotect the synthesized oligonucleotide. Suitable protecting groups are well-known in the art and include, by way of example and not limitation, acyl groups carbonates and carbamates. Fluorescein dyes including protecting groups at the 3'- and 6'-exocyclic oxygen atoms are referred to herein as "O-protected fluoresceins." In a specific, non-limiting embodiment, the protecting groups on the O-protected fluorescein are acyl groups.

The N-protected NH-rhodamine or O-protected fluorescein donor dye and the N-protected NH-rhodamine acceptor dye can be linked to one another in a variety of orientations, either directly or with the aid of a linker. In some embodiments, the donor is linked to the 2'-, 2"-, 4'-, 5'-, 7', 7"-, 5- or 6-position of the N-protected NH-rhodamine acceptor via its 2'-, 2"-, 4'-, 5'-, 7'-, 7"-, 5- or 6-position, optionally with the aid of a linker. In some embodiments, the donor and acceptor are linked to one another in a head-to-head, head-to-tail, tail-to-tail or side-to-side orientation, as will be described in more detail in a later section.

The optional linker linking the dyes may comprise virtually any combination of atoms and/or functional groups stable to oligonucleotide synthesis conditions, such as the phosphite triester chemistry conditions typically used for the solid phase synthesis of oligonucleotides. Combinations of atoms and/or functional groups can be selected to tailor the properties and/or length of the linker as desired. A variety of linkers useful for linking fluorescein and rhodamine dyes to one another in the context of energy transfer dye networks are known in the art (see, e.g., US 2006/057565, U.S. Pat. No. 7,015,000, U.S. Pat. No. 6,627,748, U.S. Pat. No. 6,544,744, U.S. Pat. No. 6,177,247, U.S. Pat. No. 6,150,107, U.S. Pat. No. 6,028,190, U.S. Pat. No. 5,958,180, U.S. Pat. No. 5,869,255, U.S. Pat. No. 5,853,992, U.S. Pat. No. 5,814,454, U.S. Pat. No. 5,804,386, U.S. Pat. No. 5,728,528, U.S. Pat. No. 5,707,804 and U.S. Pat. No. 5,688,648, the disclosures of which are incorporated herein by reference.) All of these linkers can be used to link O-protected fluoresceins to N-protected NH-rhodamines in the reagents described herein. In some embodiments, the linker is rigid in nature and is about 8 to 16 Å in length.

The label moiety, phosphate ester precursor group and optional synthesis handle of the synthesis reagents, and the label moiety, solid support and synthesis handle of the solid support reagents can be linked to one another in any fashion or orientation that does not interfere with the abilities of the various groups and moieties to carry out their respective functions. The label moiety is typically linked to one of the other moieties or groups comprising the particular reagent via a linker linked to a functional group on one of the dyes comprising the label moiety, or, alternatively, to a linker linking two or more dyes of a dye network. In embodiments in which the label moiety includes only a single N-protected NH-rhodamine fluorophore, the label moiety can be linked to the reagent via any position of the NH-rhodamine ring that does not interfere with the ability of the NH-rhodamine ring to exist in the closed, spiro lactone form. Suitable positions include, but are not limited to, carbon atoms that are adjacent to an exocyclic nitrogen atom, or atoms on the phenyl moiety, such as, for example, the 2'-, 2"-, 4'-, 5'-, 7'-, 7"-, 5- or 6-position of the rhodamine dye. In some embodiments, the label moiety is linked to a group or moiety of the reagent via the 5- or 6-position of the N-protected NH-rhodamine dye.

In embodiments in which the label moiety comprises a dye network, the label moiety may be linked to any group or moiety of the reagent at any position on any one of the dyes comprising the network that does not interfere with the desired function of the reagent, or to a linker linking two or more dyes of the network. In some specific embodiments in which the label moiety comprises an O-protected fluorescein or N-protected NH-rhodamine donor in addition to the N-protected NH-rhodamine acceptor, the label moiety can be linked to a group or moiety of the reagent at any available position on the donor or acceptor, such as, for example, the 2'-, 2"-, 4'-, 5'-, 7'-, 7"-, 5- or 6-position of the donor or acceptor. In some embodiments, the label moiety is linked to a group or moiety of the regent via the 5- or 6-position of the donor or acceptor.

In some embodiments, the label moiety is linked to a group or moiety of the reagent via the linker linking the donor and N-protected NH-rhodamine acceptor.

In other aspects, the disclosure provides intermediate molecules useful for synthesizing the reagents described herein, methods of making the reagents described herein, compounds labeled with the reagents described herein, such as, for example, tabled oligo or polynucleotides, and methods of using the labeled compounds in a variety of contexts. All of the various aspects of the disclosure are described in more detail below.

4. BRIEF DESCRIPTION OF THE FIGURES

FIGS. 1A and 1B provide exemplary embodiments of parent NH-rhodamine dyes that can be incorporated into the reagents described herein;

FIG. 1C provides exemplary embodiments of parent fluorescein dyes that can act as donors for NH-rhodamines, and that can be incorporated into the reagents described herein in embodiments in which the label moiety comprises a dye network;

FIG. 2 provides exemplary linkers that can be used to link the various different moieties comprising the reagents described herein to one another;

FIG. 3 provides exemplary embodiments of non-nucleosidic synthesis reagents that do not include synthesis handles;

FIG. 4 provides exemplary embodiments of nucleosidic synthesis reagents that do not include synthesis handles;

FIG. 5 provides exemplary embodiments of non-nucleosidic synthesis reagents that include a synthesis handle;

FIG. 6 provides exemplary embodiments of nucleosidic synthesis reagents that include synthesis handles;

FIG. 7 provides exemplary embodiments of non-nucleosidic solid support reagents;

FIG. 8 provides exemplary embodiments of nucleosidic solid support reagents;

5. DETAILED DESCRIPTION

Figure 1A:
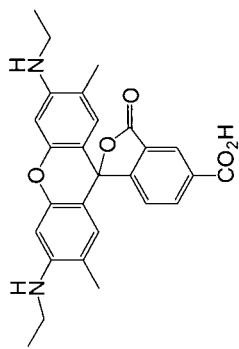
Figure 1A:
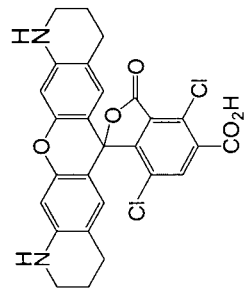
Figure 1A:
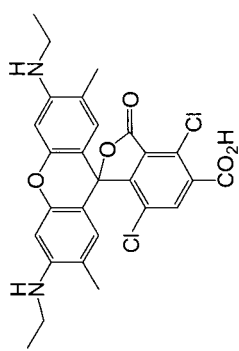
Figure 1A:
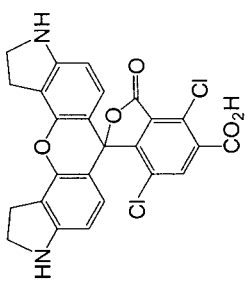
Figure 1A:
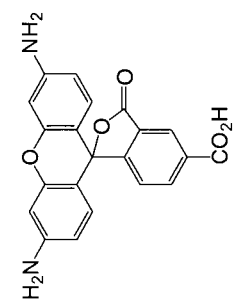
Figure 1A:
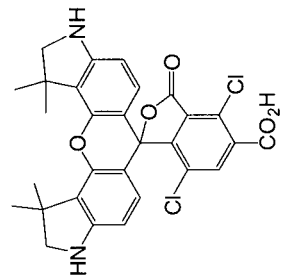
Figure 1A:
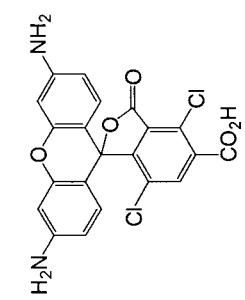
Figure 1A:
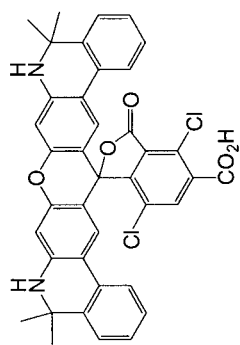

It is to be understood that both the foregoing general description and the following detailed description are exemplary and explanatory only, and are not intended to be restrictive of the compositions and methods described herein. In this disclosure, the use of "or" means "and/or" unless stated otherwise. Similarly, the expressions "comprise," "comprises," "comprising," "include," "includes" and "including" are not intended to be limiting.

5.1 Definitions

As used herein, the following terms and phrases are intended to have the following meanings:

Alkyl," by itself or as part of another substituent, refers to a saturated or unsaturated branched, straight-chain or cyclic, monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. As used herein, "lower alkyl" means (C1-C8)alkyl.

"Alkanyl," by itself or as part of another substituent, refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl(isopropyl), cyclopropan-1-yl, etc.; butanyls such as butan-1-yl, butan-2-yl(sec-butyl), 2-methyl-propan-1-yl(isobutyl), 2-methyl-propan-2-yl(t-butyl), cyclobutan-1-yl, etc.; and the like. As used herein, "lower alkanyl" means (C1-C8)alkanyl.

"Alkenyl," by itself or as part of another substituent, refers to, to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. As used herein, "lower alkenyl" means (C2-C8)alkenyl.

"Alkynyl," by itself or as part of another substituent, refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. As used herein, "lower alkynyl" means (C2-C8)alkynyl.

"Alkyldiyl," by itself or as part of another substituent, refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In some embodiments, the alkyldiyl group is (C1-C8)alkyldiyl. Specific embodiments include saturated acyclic alkanyldiyl groups in which the radical centers are at the terminal carbons, e.g., methandiyl (methano); ethan-1,2-diyl(ethano); propan-1,3-diyl(propano); butan-1,4-diyl(butano); and the like (also referred to as alkylenos, defined infra). As used herein, "lower alkyldiyl" means (C1-C8)alkyldiyl.

"Alkylene," by itself or as part of another substituent, refers to a straight-chain saturated or unsaturated alkyldiyl group having two terminal monovalent radical centers derived by the removal of one hydrogen atom from each of two terminal carbon atoms of straight-chain or branched parent alkane, alkene or alkyne, or by the removal of one hydrogen atom from each of two different ring atoms of a parent cycloalkyl. The locant of a double bond or triple bond, if present, in a particular alkylene is indicated in square brackets. Typical alkylene groups include, but are not limited to, methylene(methano); ethylenes such as ethano, etheno, ethyno; propylenes such as propano, prop[1]eno, propa[1,2]dieno, prop[1]yno, etc.; butylenes such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In some embodiments, the alkylene group is (C1-C8) or (C1-C3)alkylene. Specific embodiments include straight-chain saturated alkano groups, e.g., methano, ethano, propano, butano, and the like. As used herein, "lower alkylene" means (C1-C8)alkylene.

"Heteroalkyl," Heteroalkanyl," Heteroalkenyl," Heteroalkynyl," Heteroalkyldiyl" and "Heteroalkylene," by themselves or as part of another substituent, refer to alkyl, alkanyl, alkenyl, alkynyl, alkyldiyl and alkylene groups, respectively, in which one or more of the carbon atoms are each independently replaced with the same or different heteroatoms or heteroatomic groups. Typical heteroatoms and/or heteroatomic groups which can replace the carbon atoms include, but are not limited to, —O—, —S—, —S—O—, —NR'—, —PH—, —S(O)—, —SO$_2$—, —S(O)NR'—, —SO$_2$NR'—, and the like, including combinations thereof, where R' is hydrogen or a substitutents, such as, for example, (C1-C8)alkyl, (C6-C14) aryl or (C7-C20) arylalkyl.

"Cycloalkyl" and "Heterocycloalkyl," by themselves or as part of another substituent, refer to cyclic versions of "alkyl" and "heteroalkyl" groups, respectively. For heteroalkyl groups, a heteroatom can occupy the position that is attached to the remainder of the molecule. Typical cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like. Typical heterocycloalkyl groups include, but are not limited to, tetrahydrofuranyl (e.g., tetrahydrofuran-2-yl, tetrahydrofuran-3-yl, etc.), piperidinyl (e.g., piperidin-1-yl, piperidin-2-yl, etc.), morpholinyl (e.g., morpholin-3-yl, morpholin-4-yl, etc.), piperazinyl (e.g., piperazin-1-yl, piperazin-2-yl, etc.), and the like.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, tetrahydronaphthalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, tetrahydronaphthalene, triphenylene, trinaphthalene, and the like.

"Aryl," by itself or as part of another substituent, refers to a monovalent aromatic hydrocarbon group having the stated number of carbon atoms (i.e., C6-C14 means from 6 to 14 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. Specific exemplary aryls include phenyl and naphthyl.

"Arylalkyl," by itself or as part of another substituent, refers to an acyclic alkyl group in which one of the hydrogen atoms bonded to a carbon atom, in some embodiments a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where alkyl moieties having a specified degree of saturation are intended, the nomenclature arylalkanyl, arylalkenyl and/or arylalkynyl is used. When a defined number of carbon atoms are stated, for example, (C7-C20) arylalkyl, the number refers to the total number of carbon atoms comprising the arylalkyl group.

"Parent Heteroaromatic Ring System" refers to a parent aromatic ring system in which one or more carbon atoms are each independently replaced with the same or different heteroatoms or heteroatomic groups. Typical heteroatoms or heteroatomic groups to replace the carbon atoms include, but are not limited to, N, NH, P, O, S, S(O), $SO_2$, Si, etc. Specifically included within the definition of "parent heteroaromatic ring systems" are fused ring systems in which one or more of the rings are aromatic and one or more of the rings are saturated or unsaturated, such as, for example, benzodioxan, benzofuran, chromane, chromene, indole, indoline, xanthene, etc. Also included in the definition of "parent heteroaromatic ring system" are those recognized rings that include common substituents, such as, for example, benzopyrone and 1-methyl-1,2,3,4-tetrazole. Typical parent heteroaromatic ring systems include, but are not limited to, acridine, benzimidazole, benzisoxazole, benzodioxan, benzodioxole, benzofuran, benzopyrone, benzothiadiazole, benzothiazole, benzotriazole, benzoxazine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl," by itself or as part of another substituent, refers to a monovalent heteroaromatic group having the stated number of ring atoms (e.g., "5-14 membered" means from 5 to 14 ring atoms) derived by the removal of one hydrogen atom from a single atom of a parent heteroaromatic ring system. Typical heteroaryl groups include, but are not limited to, groups derived from acridine, benzimidazole, benzisoxazole, benzodioxan, benzodiaxole, benzofuran, benzopyrone, benzothiadiazole, benzothiazole, benzotriazole, benzoxazine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like, as well as the various hydro isomers thereof.

"Heteroarylalkyl," by itself or as part of another substituent, refers to an acyclic alkyl group in which one of the hydrogen atoms bonded to a carbon atom, in some embodiments a terminal or $sp^3$ carbon atom, is replaced with a heteroaryl group. Where alkyl moieties having a specified degree of saturation are intended, the nomenclature heteroarylalkanyl, heteroarylalkenyl and/or heteroarylalkynyl is used. When a defined number of atoms are stated, for example, 6-20-membered hetoerarylalkyl, the number refers to the total number of atoms comprising the arylalkyl group.

"Haloalkyl," by itself or as part of another substituent, refers to an alkyl group in which one or more of the hydrogen atoms is replaced with a halogen. Thus, the term "haloalkyl" is meant to include monohaloalkyls, dihaloalkyls, trihaloalkyls, etc. up to perhaloalkyls. For example, the expression "(C1-C2)haloalkyl" includes fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

The above-defined groups may include prefixes and/or suffixes that are commonly used in the art to create additional well-recognized substituent groups. As non-limiting specific examples, "alkyloxy" and/or "alkoxy" refer to a group of the formula —OR", "alkylamine" refers to a group of the formula —NHR" and "dialkylamine" refers to a group of the formula —NR"R", where each R" is an alkyl.

5.2 Exemplary Embodiments

The present disclosure provides reagents that can be used to chemically synthesize oligonucleotides bearing label moieties that comprise rhodamine dyes. Traditionally, it has been difficult to chemically synthesize rhodamine-labeled oligonucleotides owing, in part, to the lack of availability of rhodamine-containing synthesis reagents that are stable to the synthesis and/or deprotection conditions commonly employed in the step-wise chemical synthesis of oligonucleotides. It has now been discovered that protecting the exocyclic amine groups of NH-rhodamine dyes with base-labile protecting groups, such as acetyl groups, provides N-protected NH-rhodamine dyes that are stable to the chemical synthesis and deprotection conditions commonly employed in the solid-phase synthesis of oligonucleotides. As a consequence, the N-protected NH-rhodamines can be incorporated into reagents that can be used to synthesize oligonucleotides labeled with label moieties that comprise rhodamine dyes, thereby obviating the need to attach the labels post-synthesis. Because the labels are attached during synthesis, the resultant labeled oligonucleotide can be purified for use without the use of HPLC.

The reagents take advantage of various features of reagents and chemistries that are well-known for the step-wise solid phase synthesis of oligonucleotides, and can be in the form of synthesis reagents that are coupled to a hydroxyl group during the step-wise solid phase synthesis of an oligonucleotide chain, or in the form of solid support reagents to which nucleoside monomer reagents, such as nucleoside phosphoramidite reagents, and/or optionally other reagents, are coupled in a step-wise fashion to yield a synthetic oligonucleotide.

The synthesis and solid support reagents can be nucleosidic in nature in that they can include a nucleoside moiety, or they can be non-nucleosidic in nature.

All of the reagents described herein include a label moiety that comprises an N-protected NH-rhodamine dye or moiety. The N-protected NH-rhodamine dye can be the only dye comprising the label moiety or, alternatively, it can be one of two or more dyes comprising a larger dye network. The solid support reagents additionally include a solid support and one or more synthesis handles to which additional groups can be coupled. The synthesis reagents additionally include a phosphate ester precursor group useful for coupling the reagent to a primary hydroxyl group, and may optionally include one or more synthesis handles. The various moieties and groups comprising the reagents can be linked together in any fashion and/or orientation that permits them to carry out their respective functions. They can be linked to one another through linking groups included on the moieties, or they can be linked to one another with the aid of linkers.

The various moieties, groups and linkers comprising the reagents described herein are described in more detail below.

5.3 Linkers and Linking Groups

The various groups and moieties comprising the reagents described herein are typically connected to one another with linkers. The identity of any particular linker will depend, in part, upon the identities of the moieties being linked to one another. In general, the linkers include a spacing moiety that can comprise virtually any combination of atoms or functional groups stable to the synthetic conditions used for the synthesis of labeled oligonucleotides, such as the conditions commonly used to synthesize oligonucleotides by the phosphite triester method, and can be linear, branched, or cyclic in structure, or can include combinations of linear, branched and/or cyclic structures. The spacing moiety can be monomeric in nature, or it can be or include regions that are polymeric in nature. The spacing moiety can be designed to have specified properties, such as the ability to be cleaved under specified conditions, or specified degrees of rigidity, flexibility, hydrophobicity and/or hydrophilicity.

As will be described in more detail below, many embodiments of the reagents described herein are synthesized by condensing synthons to one another in specified fashions to yield the desired reagents. Each synthon typically includes one or more linking groups suitable for forming the desired linkages. Generally, the linking group comprises a functional group $F^y$ that is capable of reacting with, or that is capable of being activated so as to be able to react with, another functional group $F^z$ to yield a covalent linkage Y—Z, where Y represents the portion of the linkage contributed by $F^y$ and Z the portion contributed by $F^z$. Such groups $F^y$ and $F^z$ are referred to herein as "complementary functional groups."

Pairs of complementary functional groups capable of forming covalent linkages with one another are well-known in the art. In some embodiments, one of $F^y$ or $F^z$ comprises a nucleophilic group and the other one of $F^y$ or $F^z$ comprises an electrophilic group. Complementary nucleophilic and electrophilic groups useful for forming linkages (or precursors thereof that are or that can be suitably activated so as to form linkages) that are stable to a variety of synthesis and other conditions are well-known in the art. Examples of suitable complementary nucleophilic and electrophilic groups that can be used to effect linkages in the various reagents described herein, as well as the resultant linkages formed therefrom, are provided in Table 1, below:

TABLE 1

| Electrophilic Group | Nucleophilic Group | Resultant Covalent Linkage |
|---|---|---|
| activated esters* | amines/anilines | carboxamides |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| Alkyl halides | amines/anilines | alkyl amines |
| Alkyl halides | carboxylic acids | esters |
| Alkyl halides | thiols | thioethers |
| Alkyl halides | alcohols/phenols | ethers |
| Alkyl sulfonates | thiols | thioethers |
| Alkyl sulfonates | carboxylic acids | esters |
| Alkyl sulfonates | alcohols/phenols | esters |
| anhydrides | alcohols/phenols | esters |
| anhydrides | amines/anilines | caroboxamides |
| aryl halides | thiols | thiophenols |
| aryl halides | amines | aryl amines |
| aziridines | thiols | thioethers |
| boronates | glycols | boronate esters |
| carboxylic acids | amines/anilines | carboxamides |
| carboxylic acids | alcohols | esters |
| carboxylic acids | hydrazines | hydrazides |
| carbodiimides | carboxylic acids | N-acylureas or anhydrides |
| diazoalkanes | carboxylic acids | esters |
| epoxides | thiols | thioethers |
| haloacetamides | thiols | thioethers |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | Thiols | thioethers |
| phosphoramidites | Alcohols | phosphate esters |
| silyl halides | Alcohols | silyl ethers |
| sulfonate esters | amines/anilines | alkyl amines |
| sulfonate esters | Thiols | thioethers |
| sulfonate esters | carboxylic acids | esters |
| sulfonate esters | Alcohols | esters |
| sulfonyl halides | amines/anilines | sulfonamides |
| sulfonyl halides | phenols/alcohols | sulfonate esters |
| Diazonium salt | aryl | azo |

*Activated esters, as understood in the art, generally have the formula -C(O)Ω, where Ω is a good leaving group (e.g., oxysuccinimidyl, oxysulfosuccinimidyl, 1-oxybenzotriazolyl, etc.).
**Acyl azides can rearrange to isocyanates.

Thus, linker synthons can generally be described by the formula LG-Sp-LG, where each LG represents, independently of the other, a linking group, and Sp represents the spacing moiety. In some embodiments, linker synthons can be described by the formula $F^z$-Sp-$F^z$, where each $F^z$ represents, independently of the other, one member of a pair of complementary nucleophilic or electrophilic functional groups as described above. In specific embodiments, each $F^z$ is, independently of the other, selected from the groups listed in Table 1, supra. Linker synthons of this type form linker moieties of the formula —Z-Sp-Z—, where each Z represents, independently of the other, a portion of a linkage as described above.

Figure 2:
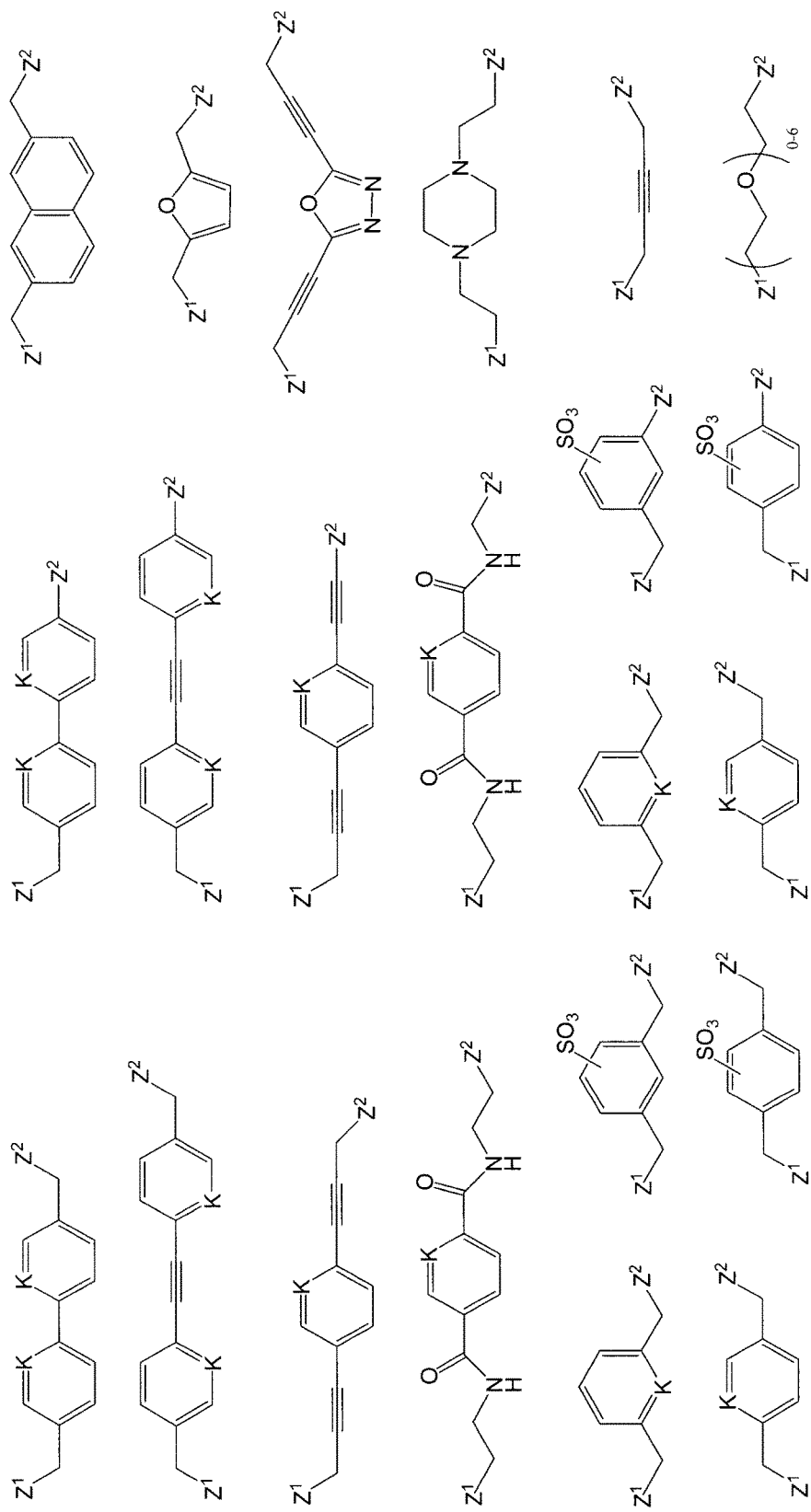

Specific linkers suitable for linking specified groups and moieties to one another in the reagents described herein will be discussed in more detail in connection with exemplary embodiments of the reagents. Non-limiting exemplary embodiments of linkers that can be used to link the various groups and moieties comprising the reagents described herein to one another are illustrated in FIG. 2. In FIG. 2, $Z^1$ and $Z^2$ each represent, independently of one another, a portion of a linkage contributed by a functional group $F^z$, as previously described, and K is selected from —CH— and —N—. In some specific embodiments of the linkers illustrated in FIG. 2, one of $Z^1$ or $Z^2$ is —NH— and the other is selected from —O—, —C(O)— and —S(O)$_2$—.

5.4 Label Moiety

All of the reagents described herein include a label moiety that comprises an NH-rhodamine dye that is protected at the exocyclic amine groups with a protecting group having specified properties. Generally, rhodamine dyes are characterized by four main features: (1) a parent xanthene ring; (2) an exocyclic amine substituent; (3) an exocyclic imminium substituent; and (4) a phenyl group substituted at the ortho position with a carboxyl group. The exocyclic amine and/or imminium groups are typically positioned at the C3 and C6 carbon atoms of the parent xanthene ring, although "extended" rhodamines in which the parent xanthene ring comprises a benzo group fused to the C3 and C4 carbons and/or the C5 and C6 carbons are also known. In these extended rhodamines, the characteristic exocyclic amine and imminium groups are positioned at the corresponding positions of the extended xanthene ring.

The carboxyl-substituted phenyl group is attached to the C9 carbon of the parent xanthene ring. As a consequence of the ortho carboxyl substituent, rhodamine dyes can exist in two different forms: (1) the open, acid form; and (2) the closed, lactone form. While not intending to be bound by any theory of operation, because NMR spectra of exemplary N-protected NH-rhodamine dyes described herein are consistent with the closed spiro lactone form of the dye, it is believed that the N-protected NH-rhodamine dyes comprising the label moiety of the reagents described herein are in the closed, spiro lactone form. Thus, the various rhodamines, as well as their unprotected counterparts, are illustrated herein in their closed, spiro lactone form. However, it is to be noted that this is for convenience only and is not intended to limit the various reagents described herein to the lactone form of the dyes.

In the closed, spiro lactone form, the A and C rings of the parent xanthene ring are aromatic, and both the C3' and C6' substituents are amines. The exocyclic amine groups of the rhodamine dyes included in the label moieties described herein are either unsubstituted or mono-substituted such that these amine groups are primary or secondary amines. Such rhodamine dyes are referred to herein as "NH-rhodamines." Thus, as used herein, an "NH-rhodamine" generally comprises one of the following parent NH-rhodamine ring structures:

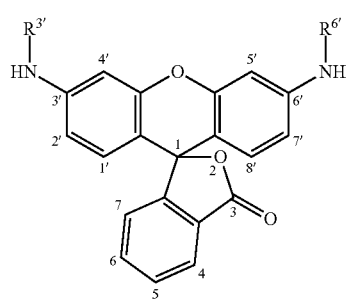
(Ia)

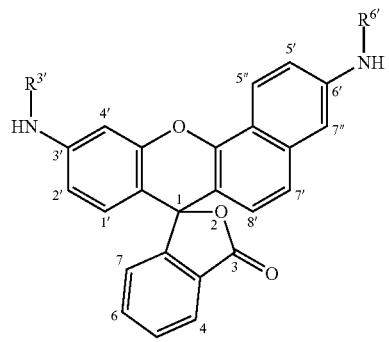
(Ib)

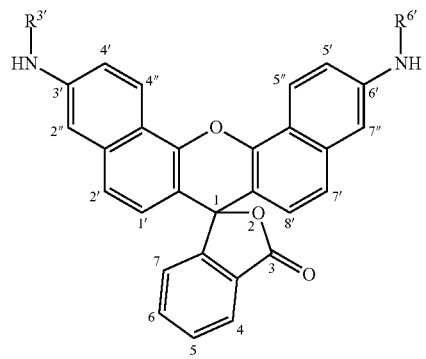
(Ic)

In the parent NH-rhodamine rings depicted above, the various carbon atoms are numbered using an arbitrary numbering convention adopted from a numbering convention commonly used for the closed, spiro lactone form of rhodamine dyes. This numbering system is being used for convenience only, and is not intended to be limiting in any way.

Figure 1B:
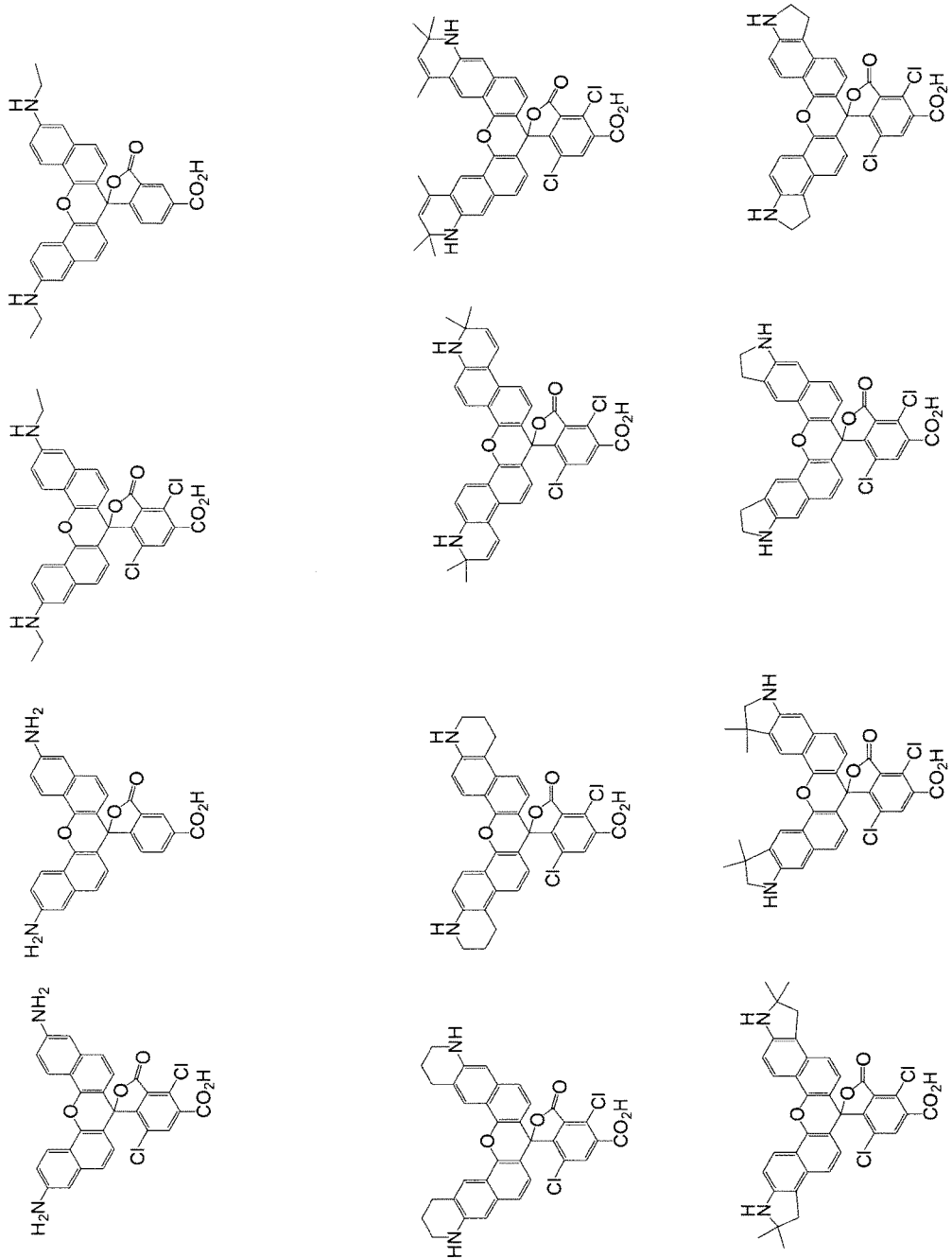

In the parent NH-rhodamines rings of structural formula (Ia), (Ib) and (Ic), $R^{3'}$ and $R^{6'}$ represent hydrogen or substituent groups substituting the exocyclic amines. The $R^{3'}$ and/or $R^{6'}$ substituents can be the same or different, and can comprise groups such as substituted or unsubstituted alkyl, aryl or arylalkyl groups. Alternatively, the $R^{3'}$ and/or $R^{6'}$ groups can comprise substituents that are bridged to an adjacent carbon atom such that the illustrated nitrogen atom is included in a ring that contains 5- or 6-ring atoms. The ring may be saturated or unsaturated, and one or more of the ring atoms can be substituted. When the ring atom(s) are substituted, the substituents are typically, independently of one another, selected from lower alkyl, C6-C10 aryl and C7-C16 arylalkyl groups. Alternatively, two adjacent ring atoms may be included in an aryl bridge, such as a benzo or naphtho group. Non-limiting exemplary embodiments of rhodamine dyes that include a parent NH-rhodamine ring according to structural formula (Ia) in which the $R^{3'}$ and/or $R^{6'}$ groups are hydrogen or lower alkyl groups or are included in optionally substituted rings with adjacent carbon atoms are illustrated in FIG. 1A. Non-limiting exemplary embodiments of rhodamine dyes that include a parent NH-rhodamine ring according to structural formula (Ic) in which the $R^{3'}$ and $R^{6'}$ groups are hydrogen or lower alkyl groups or are included in optionally substituted rings with adjacent carbon atoms are illustrated in FIG. 1B.

One or more of the carbon atoms at positions C1', C2', C2", C4', C4", C5', C5", C7', C7" and C8' of the parent NH-rhodamine rings according to structural formulae (Ia), (Ib) and (Ic) can be, independently of one another, substituted with substituent groups. Groups useful for substituting rhodamine dyes at these positions are well known in the art, and are described, for example, in U.S. Pat. No. 4,622,400, U.S. Pat. No. 5,750,409, U.S. Pat. No. 5,847,162, U.S. Pat. No. 6,017,712, U.S. Pat. No. 6,080,852, U.S. Pat. No. 6,184,379 and U.S. Pat. No. 6,248,884, the disclosures of which are incorporated herein by reference. All of these substituent groups can be used to substitute the parent NH-rhodamine rings described herein.

In some embodiments, the substituent groups are, independently of one another, selected from lower alkyl, (C6-C14) aryl, (C7-C20) arylalkyl, 5-14 membered heteroaryl, 6-20 membered heteroarylalkyl, —$R^b$ and —$(CH_2)_x$—$R^b$, where x is an integer ranging from 1 to 10 and $R^b$ is selected from —X, —OH, —$OR^a$, —SH, —$SR^a$, —$NH_2$, —$NHR^a$, —$NR^cR^c$, —$N^+R^cR^cR^c$, perhalo lower alkyl, trihalomethyl, trifluoromethyl, —$B(OH)_3$, —$B(OR^a)_3$, —$B(OH)O^-$, —$B(OR^a)_2O^-$, —$B(OH)(O^-)_2$, —$B(OR^a)(O^-)_2$, —$P(OH)_2$, —$P(OH)O^-$, —$P(OR^a)_2$, —$P(OR^a)O^-$, —$P(O)(OH)_2$, —$P(O)(OH)O^-$, —$P(O)(O^-)_2$, —$P(O)(OR^a)_2$, —$P(O)(OR^a)O^-$, —$P(O)(OH)(OH)(OR^a)$, —$OP(OH)_2$, —$OP(OH)O^-$, —$OP(OR^a)_2$, —$OP(OR^a)O^-$, —$OP(O)(OH)_2$, —$OP(O)(OH)O^-$, —$OP(O)(O^-)_2$, —$OP(O)(OR^a)_2$, —$OP(O)(OR^a)O^-$, —$OP(O)(OR^a)(OH)$, —$S(O)_2O^-$, —$S(O)_2OH$, —$S(O)_2R^a$, —C(O)H, —$C(O)R^a$, —C(S)X, —$C(O)O^-$, —C(O)OH, —$C(O)NH_2$, —$C(O)NHR^a$, —$C(O)NR^cR^c$, —$C(S)NH_2$, —$C(O)NHR^a$, —$C(O)NR^cR^c$, —$C(NH)NH_2$, —$C(NH)NHR^a$, and —$C(NH)NR^cR^c$, where X is a halo (preferably fluoro or chloro), each $R^a$ is, independently of the others, selected from lower alkyl, (C6-C14) aryl, (C7-C20) arylalkyl, 5-14 membered heteroaryl and 6-20 membered heteroarylalkyl, and each $R^c$ is, independently of the others, an $R^a$, or, alternatively, two $R^c$ bonded to the same nitrogen atom may be taken together with that nitrogen atom to form a 5- to 8-membered saturated or unsaturated ring that may optionally include one or more of the same or different ring heteroatoms, which are typically selected from O, N and S.

Alternatively, the C1' and C2' substituents, the C7' and C8' substituents, the C5' and C5" substituents and/or the C4' and C4" substituents can be taken together to form substituted or unsubstituted aryl bridges, such as benzo bridges, with the proviso that the C1' and C2' substituents, and C7' and C8' substituents are not simultaneously included in an aryl bridge.

In general, the groups used to substitute the C1', C2', C2", C4', C4", C5', C5", C7', C7" and C8' carbons should not promote quenching of the rhodamine dye, although in some embodiments quenching substituents may be desirable. Substituents that tend to quench rhodamine dyes include carbonyl, carboxylate, heavy metals, nitro, bromo and iodo. Phenyl groups positioned at $R^{3'}$ and/or $R^{6'}$ also tend to cause quenching.

The carbon atoms at positions C4, C5, C6 and C7 of the parent NH-rhodamine rings of structural formulae (Ia), (Ib) and (Ic) can also, independently of one another, include optional substituents. These substituents can be selected from the various substituents described above. In some embodiments, the carbon atoms at positions C4 and C7 are substituted with chloro groups such that the parent NH-rhodamine dye is an NH-4,7-dichlororhodamine dye.

A vast number of rhodamine dyes that include parent NH-rhodamine rings according to structural formulae (Ia), (Ib) and (Ic) that can be included in the label moiety of the reagents described herein are known in the art, and are described, for example, in U.S. Pat. No. 6,248,884; U.S. Pat. No. 6,111,116; U.S. Pat. No. 6,080,852; U.S. Pat. No. 6,051,719; U.S. Pat. No. 6,025,505; U.S. Pat. No. 6,017,712; U.S. Pat. No. 5,936,087; U.S. Pat. No. 5,847,162; U.S. Pat. No. 5,840,999; U.S. Pat. No. 5,750,409; U.S. Pat. No. 5,366,860; U.S. Pat. No. 5,231,191; U.S. Pat. No. 5,227,487; WO 9736960; WO 9927020; Lee et al., 1992, Nucl. Acids Res. 20:2471-2483; Arden-Jacob, "Neue Lanwellige Xanthen-Farbstoffe für Fluoreszenzsonden and Farbstoff Lauer, Springer-Verlag, Germany, 1993; Sauer et al., 1995, Fluorescence 5:247-261; Lee et al., 1997, Nucl. Acids Res. 25:2816-2822; and Rosenblum et al., 1997, Nucl. Acids Res. 25:4500-4504, the disclosures of which are incorporated herein by reference. Any of the dyes described in these references in which the exocyclic amines are primary or secondary amines as described herein, or 4,7-dichloro analogues of such NH-rhodamine dyes, can be included in the label moiety of the reagents described herein.

When included in a label moiety, the exocyclic amines of the parent NH-rhodamine ring are protected with protecting groups having specified properties. Such protected NH-rhodamines are referred to herein as "N-protected NH-rhodamines." The N-protected NH-rhodamines that correspond to the parent NH-rhodamine rings of structural formulae (Ia), (Ib) and (Ic) and are illustrated below as structural formulae (IIa), (IIb) and (IIc):

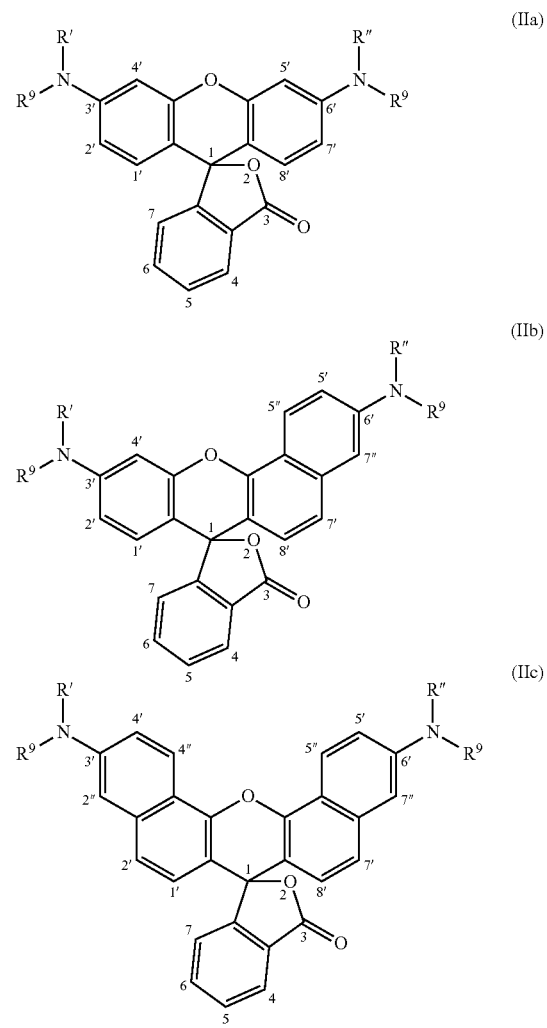

In structural formulae (IIa), (IIb) and (IIc), R' is hydrogen or $R^{3'}$ and R" is hydrogen or $R^{6'}$, where $R^{3'}$ and $R^{6'}$ are as defined for structural formulae (Ia), (Ib) and (Ic), supra, and $R^9$ represents a protecting group. The N-protected NH-rhodamines can include substituents at one or more of positions C1', C2', C2", C4', C4", C5', C5", C7', C7", C8', C4, C5, C6, and C7, as previously described in connection with the parent NH-rhodamine rings according to structural formulae (Ia), (Ib) and (Ic).

Since the reagents described herein will be used to chemically synthesize labeled oligonucleotides, protecting groups $R^9$ that are stable to the organic synthesis conditions used to synthesize oligonucleotides should be used. As mentioned above, protecting groups $R^9$ that protect the amine in the form of an amide, for example, a carboxamide, a sulfonamide or a phosphoramide, should be selected, as protecting the exocyclic amines in this matter is believed to "lock" the protected NH-rhodamine in the closed, lactone, form, contributing to the stability of the reagents described herein. Although not required, it is convenient to utilize protecting groups $R^9$ that are labile under the conditions used to remove the groups protecting the exocyclic amines of the nucleobases of the synthetic oligonucleotide, so that all protecting groups can be removed in a single step.

The conditions used to synthesize and deprotect synthetic oligonucleotides are well-known in the art, and are described, for example, in Current Protocols in Nucleic Acid Chemistry, Vol. I, Beancage et al., Eds., John Wiley & Sons, 2002, the disclosure of which are incorporated herein by reference. Briefly, synthesis methods that employ phosphoramidite reagents involve multiple rounds of: (i) DMT deprotection to reveal a free hydroxyl, which can be effected by treatment with 2.5% or 3% di- or tri-chloroacetic acid in dichloromethane; (ii) coupling of nucleoside or other phosphoramidite reagents to the free hydroxyl, which can be carried out in acetonitrile containing 0.45 M or 0.5 M tetrazole; (iii) oxidation, which can be carried out by treatment with $I_2$/2,6-lutidine/$H_2O$; and capping, which can be carried out by treatment with 6.5% acetic anhydride in tetrahydrofuran (THF) followed by treatment with 10% 1-methylimidazole (NMI) in THF.

Other conditions for carrying out the various steps in the synthesis are also known and used. For example, phosphoramidite coupling can be carried out in acetonitrile containing 0.25 M 5-ethylthio-1H-tetrazole, 0.25 M4,5-dicyanoimidazole (DCI) or 0.25 M 5-benzylthio-1H-tetrazole (BTT). Oxidation an be carried out in 0.1 M, 0.05 M or 0.02 M $I_2$ in THF/$H_2O$/pyridine (7:2:1). Capping can be carried out by treatment with THF/lutidine/acetic anhydride followed by treatment with 16% NMI in THF; by treatment with 6.5% DMAP in THF followed by treatment with 10% MeIm in THF; or by treatment with 10% MeIm in THF followed by treatment with 16% MeIm in THF.

Removal of any protecting groups and cleavage from the synthesis reagent is typically effected by treatment with concentrated ammonium hydroxide at 60° C. for 1-12 hr, although nucleoside phosphoramidite reagents protected with groups that can be removed under milder conditions, such as by treatment with concentrated ammonium hydroxide at room temperature for 4-17 hrs or treatment with 0.05 M potassium carbonate in methanol, or treatment with 25% t-butylamine in $H_2O$/EtOH, are also known and used.

Skilled artisans will be readily able to select protecting groups having properties suitable for use under specific synthesis and deprotection and/or cleavage conditions. A wide variety of amine protecting groups are taught, for example in, Greene & Wuts, "Protective Groups In Organic Chemistry," 3d Edition, John Wiley & Sons, 1999 (hereinafter "Green & Wuts") at for example, pages 309-405. Skilled artisans can readily select protecting groups $R^9$ having suitable properties from amongst those taught in Green & Wuts.

In some embodiments, the protecting groups $R^9$ are acyl groups of the formula —C(O)$R^{10}$, where $R^{10}$ is selected from hydrogen, lower alkyl, methyl, —$CX_3$, —$CHX_2$, —$CH_2X$, —$CH_2$—$OR^d$ and phenyl optionally mono-substituted with a lower alkyl, methyl, —X, —$OR^d$, cyano or nitro group, where $R^d$ is selected from lower alkyl, phenyl and pyridyl, and each X is a halo group, typically fluoro, or chloro. In some embodiments, $R^{10}$ is methyl. In some embodiments, $R^{10}$ is trifluoromethyl.

Acyl protecting groups such as those defined by —C(O)$R^{10}$ can be removed under a variety of basic conditions, including the mild conditions used to remove protecting groups from oligos synthesized with "base labile" phosphoramidite reagents, as are well-known in the art. Exemplary conditions that can be used are specified above.

As will be described in more detail in later sections, the N-protected NH-rhodamine moiety comprising the label moiety may be linked to other groups or moieties. For example, the N-protected NH-rhodamine may be linked to another dye comprising the label moiety, to a phosphate ester precursor group, to a linker, to a synthesis handle, to a quenching moiety, to a moiety that functions to stabilize base-pairing interactions (such as, for example an intercalating dye or a minor-groove-binding molecule), or to other moieties. Such linkages are typically effected via linking groups LG (described above in connection with the linkers) attached to the N-protected NH-rhodamine synthons used to synthesize the reagents.

The linking group LG can be attached to any available carbon atom of the N-protected NH-rhodamine synthon, or to a substituent group attached to one of these carbon atoms. The positions of the linking groups may depend, in part, on the group or moiety to which the N-protected NH-rhodamine synthon will be attached. In some embodiments, the linking group is attached at the C2', C2", C4', C5', C7', C7", C5, or C6 position of the N-protected NH-rhodamine synthon. In a specific embodiment, the linking group is attached at the C4', C5', C5 or C6 position.

The N-protected NH-rhodamine synthon can include a single linking group LG, or it can include more than one linking group LG. In embodiments that employ more than one linking group, the linking groups may be the same, or they may be different. N-protected NH-rhodamine synthons that include multiple linking groups LG that are different from one another can have different groups or moieties attached to different positions of the parent NH-rhodamine ring using orthogonal chemistries.

The identity of a linking group may, in some instances, depend upon its location on the parent NH-rhodamine ring. In some embodiments in which the linking group LG is attached at the C4'- or C5'-position of the parent NH-rhodamine ring, the linking group LG is a group of the formula —$(CH_2)_n$—$F^y$, where n is an integer ranging from 0 to 10 and $F^y$ is as described above. In a specific embodiment, n is 1 and $F^y$ is —$NH_2$.

In some embodiments in which the linking group LG is attached at the 5- or 6-position of the parent NH-rhodamine ring, the linking group LG is a group of the formula —$(CH_2)_n$—C(O)$OR^f$, where $R^f$ is selected from hydrogen and a good leaving group and n is as previously defined. In some specific embodiments, the linking group LG comprises an NHS ester. In some specific embodiments, n is 0 and $R^f$ is NHS.

In some embodiments, the N-protected NH-rhodamine comprising the label moiety of the various reagents described herein is described by structural formulae (IIIc), (IIIb) or (IIIc); below:

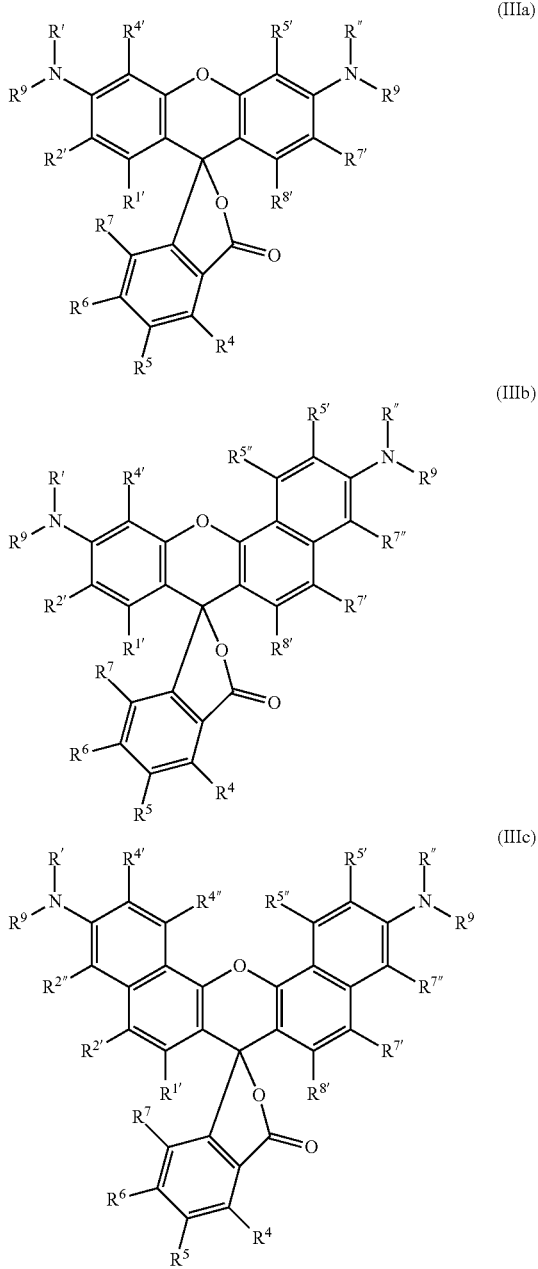

wherein:
R' is selected from $R^{3'}$ and hydrogen;
R" is selected from $R^{6'}$ and hydrogen;
$R^9$ is an acyl protecting group, optionally of the formula —C(O)$R^{10}$, where $R^{10}$ is as previously defined;
$R^{1'}$, $R^{2'}$, $R^{2''}$, $R^{4'}$, $R^{4''}$, $R^{5'}$, $R^{5''}$, $R^{7'}$, $R^{7''}$ and $R^{8'}$, when taken alone, are each, independently of one another, selected from hydrogen lower alkyl, (C6-C14) aryl, (C7-C20) arylalkyl, 5-14 membered heteroaryl, 6-20 membered heteroarylalkyl, —$R^b$ and —(CH$_2$)$_x$—$R^b$, where x and $R^b$ are as previously defined, or, alternatively, $R^{1'}$ and $R^{2'}$ or $R^{7'}$ and $R^{8'}$ are taken together with the carbon atoms to which they are bonded to form a benzo group and/or $R^{4'}$ and $R^{4''}$ and/or $R^{5'}$ and $R^{5''}$ are taken together with the carbon atoms to which they are bonded to form a benzo group;

$R^{3'}$ and $R^{6'}$, when taken alone, are each, independently of one another, selected from lower alkyl, (C6-C14) aryl, (C7-C20) arylalkyl, 5-14 membered heteroaryl and 6-20 membered heteroarylalkyl, or alternatively, $R^{3'}$ and $R^{2'}$ or $R^{4'}$ and/or $R^{6'}$ and $R^{5'}$ or $R^{7'}$ in the compounds of structural formula (IIIa), $R^{3'}$ and $R^{2'}$ or $R^{4'}$ and/or $R^{6'}$ and $R^{5'}$ or $R^{7''}$ in the compounds of structural formula (IIIb), or $R^{3'}$ and $R^{2''}$ or $R^{4'}$ and/or $R^{6'}$ and $R^{5'}$ or $R^{7''}$ in the compounds of structural formula (IIIc) are taken together with the atoms to which they are bonded to form a 5- or 6-membered saturated or unsaturated ring that may optionally include from 1 to 4 additional heteroatoms (typically selected from O, N and S) and that is optionally substituted with one or more of the same or different lower alkyl, benzo or pyrido groups;

and $R^4$, $R^5$, $R^6$, and $R^7$ are each, independently of one another, selected from hydrogen, lower alkyl, (C6-C14) aryl, (C7-C20) arylalkyl, 6-14 membered heteroaryl, 7-20 membered heteroarylalkyl, —$R^b$ and —(CH$_2$)$_x$—$R^b$, where x and $R^b$ are as previously defined, with the proviso that at least one of $R^{2'}$, $R^{4'}$, $R^{5'}$, $R^{7'}$, $R^5$ or $R^6$ in the compounds structural formula (IIIa), at least one of $R^{2'}$, $R^{4'}$, $R^{5'}$, $R^{7''}$, $R^5$ or $R^6$ in the compounds of structural formula (IIIb) and at least one of $R^{2''}$, $R^{4'}$, $R^{5'}$, $R^{7''}$, $R^5$ or $R^6$ in the compounds of structural formula (IIIc) comprises a group of the formula —Y—, where Y represents a portion of a linkage contributed by a linking group comprising a functional group $F^y$, as described above.

In some embodiments, the N-protected NH-rhodamine comprising the label moiety of the various reagents described herein excludes 4,7-dichloro R6G (5- and/or 6-isomers) and/or rhodamines described by structural formula (IIIa) in which:
R' and R" are each ethyl;
$R^{1'}$, $R^{4'}$, $R^{5'}$ and $R^{6'}$ are each hydrogen;
$R^{2'}$ and $R^{7'}$ are each methyl;
$R^4$ and $R^7$ are each chloro; and
one of $R^5$ or $R^6$ is hydrogen and the other is —C(O)—.

In some embodiments, the N-protected NH-rhodamine moieties according to structural formulae (IIIa), (IIIb) and (IIIc), are, respectively, selected from moieties defined by structural formulae (IIIa.1), (IIIa.2), (IIIb.1), (IIIb.2), (IIIc.1) and (IIIc.2), below:

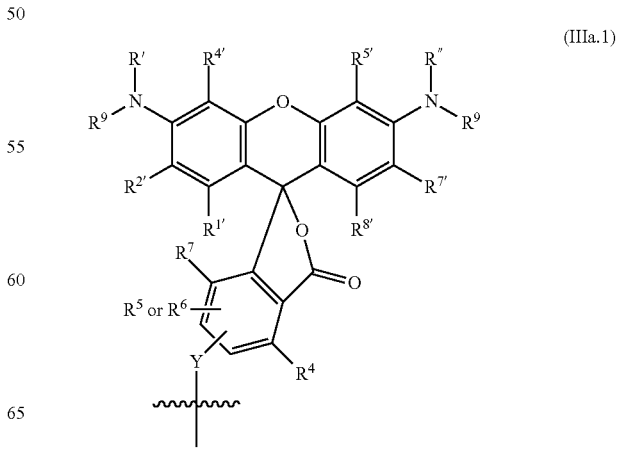

-continued

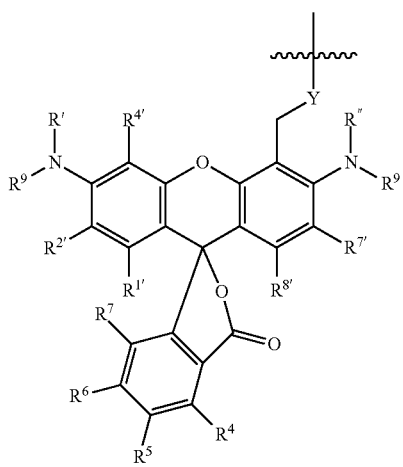
(IIIa.2)

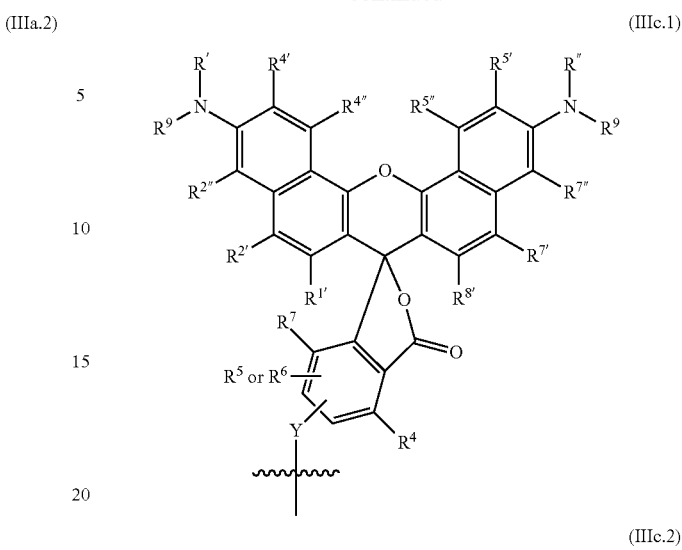
(IIIc.1)

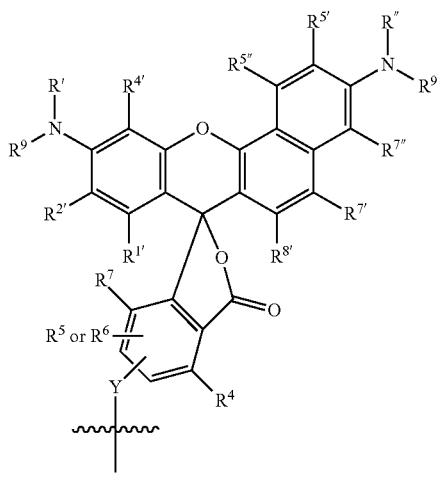
(IIIb.1)

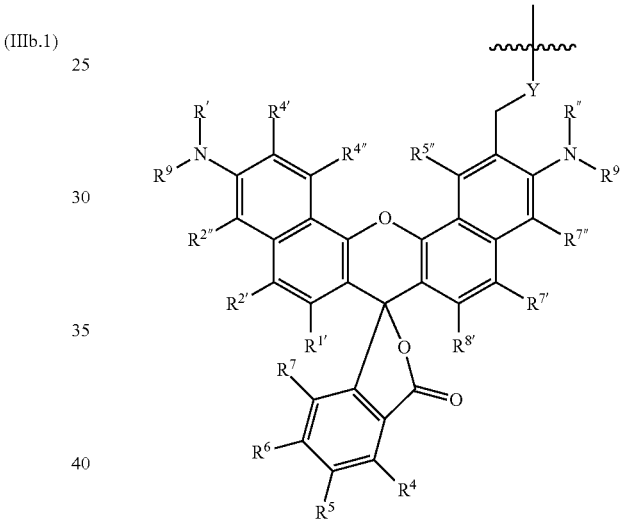
(IIIc.2)

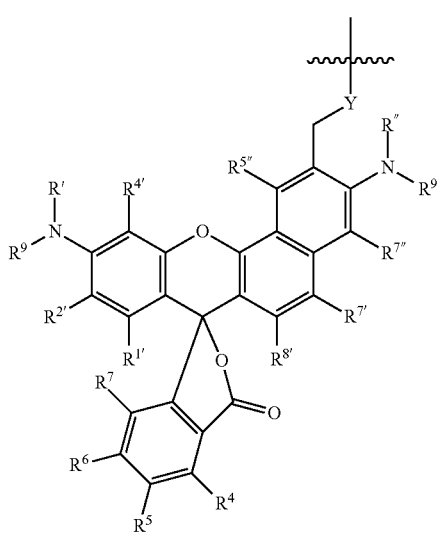
(IIIb.2)

wherein R', R", R$^{1'}$, R$^{2'}$, R$^{2''}$, R$^{3'}$, R$^{4'}$, R$^{4''}$, R$^{5'}$, R$^{5''}$, R$^{6'}$, R$^{7'}$, R$^{7''}$, R$^{8'}$, R$^4$, R$^5$, R$^6$, R$^7$, R$^9$ and Y are as previously defined for structural formulae (IIIa), (IIIb) and (IIIc).

Specific exemplary embodiments of moieties defined by structural formulae (IIIa), (IIIa.1), (IIIa.2), (IIIb), (IIIb.1), (IIIb.2), (IIIc), (IIIc.1) and (IIIc.2) include structures that have one or more applicable features selected from:

(i) Y is selected from —C(O)—, —S(O)$_2$—, —S— and —NH—;

(ii) R$^4$ and R$^7$ are each chloro;

(iii) R$^{1'}$ and R$^{8'}$ are each hydrogen;

(iv) R$^{1'}$ and R$^{2'}$ or R$^{7'}$ and R$^{8'}$ are taken together to form a benzo group;

(v) R$^{2'}$ and R$^{7'}$ are each hydrogen or lower alkyl;

(vi) R' is R$^{3'}$ and R" is R$^{6'}$;

(vii) R' is R$^{3'}$, R" is R$^{6'}$, and R$^{3'}$ and R$^{6'}$ are taken together with a substituent group on an adjacent carbon atom to form a group selected from —CH$_2$CH$_2$—, —CH$_2$CH$_2$CH$_2$—, —C(CH$_3$)$_2$CH═C(CH$_3$)—, —C(CH$_3$)$_2$CH═CH—, —CH$_2$—C(CH$_3$)$_2$— and

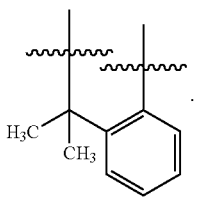

As discussed previously, the label moiety can comprise one or more additional dyes such that the N-protected NH-rhodamine, once deprotected, is a member of a larger, energy transfer dye network. Such energy transfer dye networks are well-known in the art, and include combinations of fluorescent dyes whose spectral properties are matched, and/or whose relative distances to one another are adjusted, so that one fluorescent dye in the network, when excited by incident irradiation of an appropriate wavelength, transfers its excitation energy to another fluorescent dyes in the network, which then transfers its excitation energy to yet another fluorescent dye in the network, and so forth, resulting in fluorescence by the ultimate acceptor dye in the network. Dye networks provide label moieties having long Stoke's shifts. In such networks, fluorophores that transfer, or donate, their excitation energy to another fluorophore in the network are referred to as "donors." Fluorophores that receive, or accept, excitation energy from another fluorophore are referred to as "acceptors." In dye networks containing only two fluorescent dyes, one acts as the donor and the other as the acceptor. In dye networks containing three or more fluorescent dyes, at least one dye acts as both a donor and acceptor. The principles of how dye networks work, as well as the criteria for selecting and linking individual dyes suitable for creating such networks are well known, and are described, for example, in Hung et al., 1997, Anal. Biochem. 252:78-88.

In the label moieties described herein that comprise dye networks, the N-protected NH-rhodamine dye, once deprotected, may act as a donor or an acceptor, or as both a donor and acceptor, depending upon the identities of the other dyes comprising the network and the desired incident and fluorescent wavelengths. A vast number of dyes suitable for use as donors and/or acceptors for NH-rhodamine dyes are known in the art, and include by way of example and not limitation, xanthene dyes (such as, for example, fluorescein, rhodamine and rhodol dyes), pyrene dyes, coumarin dyes (for example, hydroxy- and amino-coumarins), cyanine dyes, phthalocyanine dyes and lanthenide complexes. Specific, non-limiting examples of these dyes in the context of energy transfer dye networks are described in Hung et al., 1996, Anal. Biochem. 238:165-170; Medintz et al., 2004, Proc. Nat'l Acad. Sci. USA 101(26):9612-9617; U.S. Pat. No. 5,800,996; Sudhaker et al., 2003, Nucleosides, Nucleotides & Nucleic Acids 22:1443-1445; U.S. Pat. No. 6,358,684; Majumdar et al., 2005, J. Mol. Biol. 351:1123-1145; Dietrich et al., 2002, Reviews Mol. Biotechnology 82(3):211-231; Tsuji et al., 2001, Biophysical J. 81(1):501-515; Dickson et al., 1995, J. Photochemistry & Photobiology 27(1):3-19; and Kumar et al., 2004, Developments in Nucl. Acid Res. 1:251-274, the disclosures of which are incorporated herein by references. Any of these dyes that can be suitably protected in accordance with the principles described herein can be used as donor and acceptor dyes in label moieties that comprise dye networks. In some embodiments, one or more of the donor and/or acceptor dyes comprising the network can be an N-protected NH-rhodamine dye as described herein. Specific positions for attaching donor and/or acceptor dyes to rhodamine dyes to form dye networks, as well as specific linkages and linkers useful for attaching such dyes, are well-known in the art. Specific examples are described, for example, in U.S. Pat. No. 6,811,979; U.S. Pat. No. 6,008,379; U.S. Pat. No. 5,945,526; U.S. Pat. No. 5,863,727; and U.S. Pat. No. 5,800,996, the disclosures of which are incorporated herein by reference.

In some embodiments, the linker linking the donor and acceptor dyes is an anionic linker as described in U.S. Pat. No. 6,811,979, the disclosure of which is incorporated herein by reference (see, e.g., the disclosure at Col. 17, line 25 through Col. 18, line 37 and FIGS. 1-17).

In some embodiments of the reagents described herein, the label moiety includes a donor dye for the NH-rhodamine dye. In some embodiments, the donor dye is a fluorescein or rhodamine dye, such as, for example, one of the NH-rhodamine dyes described herein. In a specific embodiment, the donor dye is a fluorescein dye. Fluorescein dyes are similar in structure to rhodamine dyes, with the exception that the 3- and 6-positions of the parent xanthene ring (corresponding to the 3'- and 6'-positions of the NH-rhodamine rings of structural formulae (Ia), (Ib) and (Ic)), are substituted with a hydroxyl groups. Like the rhodamines, the fluoresceins can also have extended ring structures in which the carbon atoms at positions C3 and C4 and/or C5 and C6 of the parent xanthene ring are included in aryl bridges such as benzo groups. Thus, the fluoresceins generally include compounds according to structural formulae (IVa), (IVb) and (IVc), below:

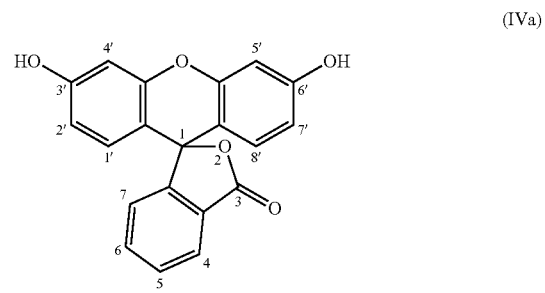

(IVa)

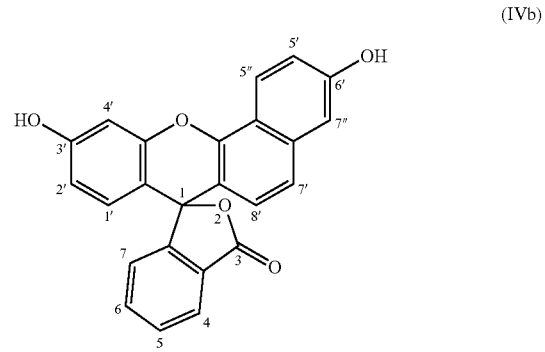

(IVb)

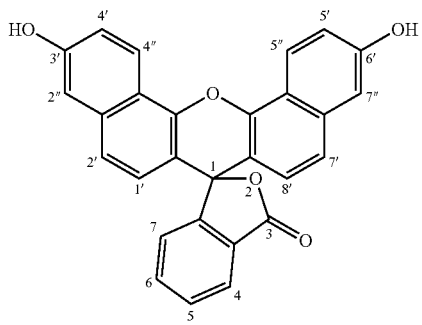

(IVc)

Like the NH-rhodamines, the carbons at positions C1', C2', C2", C4', C4", C5', C5", C7', C7", C8', C4, C5, C6 and C7 of the fluorescein rings of structural formulae (IVa), (IVb) and (IVc) can be substituted with a variety of different substituents, such as those described previously for the NH-rhodamines.

When included in the label moieties described herein, the hydroxyls at the C3' and C6' positions should be protected with protecting groups having the same general properties as the groups protecting the exocyclic amines of the NH-rhodamines, discussed above. Thus, in specific embodiments the protecting groups are stable to the conditions used to synthesize oligonucleotides, such as the conditions used to synthesize and oxidize oligonucleotides via the phosphite triester method, and are labile under the conditions typically used to deprotect and/or cleave synthetic oligonucleotides from the synthesis resin, such as, for example, incubation in concentrated ammonium hydroxide at room temperature or 55° C.

A wide variety of protecting groups having suitable properties are known in the art, and include by way of example and not limitation, the acyl groups described above in connection with N-protected NH-rhodamine dyes. In a specific embodiment, the protecting group is of the formula —C(O)—$R^{10}$, where $R^{10}$ is as previously defined. In some embodiments, $R^{10}$ is t-butyl. Fluoresceins in which the C3' and C6' exocyclic hydroxyls include protecting groups are referred to herein as "O-protected fluoresceins." O-protected fluoresceins corresponding to the fluoresceins of structural formulae (IVa), (IVb) and (IVc), respectively, are illustrated as structural formulae (Va), (Vb) and (Vc), below:

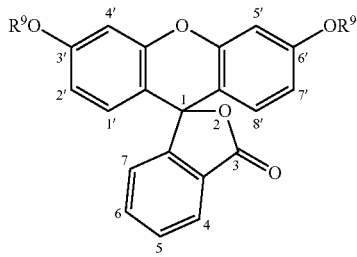

(Va)

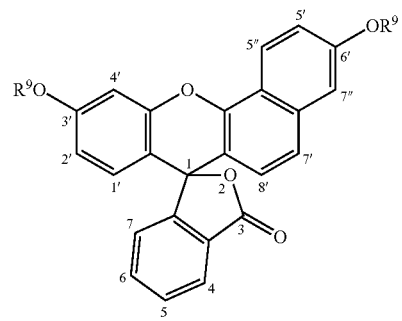

(Vb)

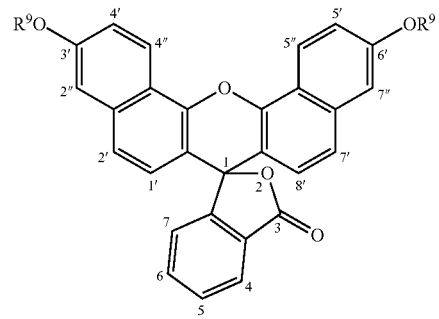

(Vc)

wherein $R^9$ represents the protecting group.

Figure 1C:
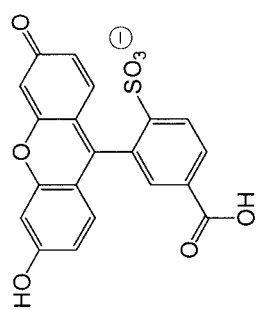
Figure 1C:
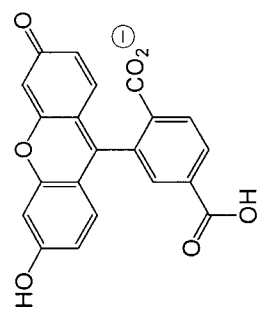
Figure 1C:
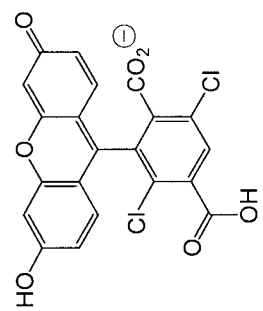
Figure 1C:
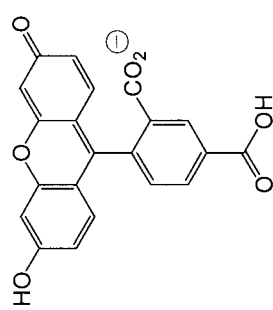
Figure 1C:
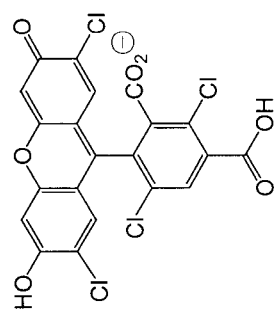

A vast variety of different fluorescein dyes that can be suitably protected and incorporated into label moieties for use as a donors for the NH-rhodamine moiety are known in the art. Specific exemplary fluorescein dyes are described, for example, in U.S. Pat. No. 6,221,604; U.S. Pat. No. 6,008,379; U.S. Pat. No. 5,840,999; U.S. Pat. No. 5,750,409; U.S. Pat. No. 5,654,441; U.S. Pat. No. 5,188,934; U.S. Pat. No. 5,066,580; U.S. Pat. No. 4,481,136; U.S. Pat. No. 4,439,356; WO 99/16832; and EP 0 050 684, the disclosures of which are incorporated herein by reference. Skilled artisans will be able to select a fluorescein having spectral properties suitable for use as a donor for a specific NH-rhodamine. Specific embodiments of parent fluorescein dyes that may be incorporated in the label moieties of the reagents described herein are illustrated in FIG. 1C.

The donor and N-protected NH-rhodamine acceptor can be linked to one another in a variety of orientations, either directly or with the aid of a linker. In some embodiments in which the donor is an O-protected fluorescein or an N-protected NH-rhodamine, the donor is linked to the 2'-, 2"-, 4'-, 5'-, 7'-, 7"-, 5- or 6-position of the N-protected NH-rhodamine acceptor via its 2'-, 2"-, 4'-, 5'-, 7'-, 7"-, 5- or 6-position.

Specific exemplary linkage orientations are provided in Table 2, below:

TABLE 2

| donor/acceptor | acceptor/donor | nickname |
| --- | --- | --- |
| 4'- or 5'- | 4'- or 5'- | head-to-head |
| 4'- or 5'- | 5- or 6- | head-to-tail |
| 5- or 6' | 5- or 6- | tail-to-tail |
| 2'-, 2"-, 7'- or 7"- | 2'-, 2-, 7'- or 7"- | side-to-side |
| 2'-, 2"-, 7'- or 7"- | 4'- or 5'- | side-to-head |
| 2'-, 2"-, 7'- or 7"- | 5- or 6- | side-to-tail |

Label moieties comprising dye networks, such as the donor-acceptor dye networks of Table 2, can be linked to the remainder of the reagent at any available position. In some embodiments, label moieties comprising head-to-head linked acceptor/donor pairs are attached to the remainder of the reagent via the 5- or 6-position of the donor or acceptor moiety. In some embodiments, label moieties comprising head-to-tail linked acceptor/donor pairs are attached to the remainder of the reagent via an available 4'-, 5'-, 5- or 6-position of the donor or acceptor moiety. In some embodiments, label moieties comprising tail-to-tail linked acceptor/donor pairs are attached to the remainder of the reagent via the 4'- or 5'-position of the donor or acceptor. In some embodiments, label moieties comprising side-to-side linked acceptor/donor pairs are attached to the remainder of the reagent via the 4'-, 5'-, 5- or 6-position of the donor or acceptor. In some embodiments, label moieties comprising side-to-head linked acceptor/donor pairs are attached to the remainder of the reagent via an available 4'-, 5'-, 5- or 6-position of the donor or acceptor. In some embodiments, label moieties comprising side-to-tail linked acceptor/donor pairs are attached to the remainder of the reagent via an available 4'-, 5'-, 5- or 6-position of the donor or acceptor.

Regardless of their orientation, the O-protected fluorescein or N-protected NH-rhodamine donor and the N-protected NH-rhodamine acceptor are typically linked to one another via a linker. It has been discovered previously that it may be advantageous to link such donor and acceptor dyes via linkers that are rigid in nature and/or that are relatively long, for example, in the range of approximately 12-20 Å in length (as used herein, the "length" of a linker refers to the distance between the linked moieties as determined by calculating the sum of the lengths of the chemical bonds defining the shortest continuous path between the moieties). Without intending to be bound by any theory of operation, it is believed that linkers that tend to hold the donor and acceptor in close proximity to one another without permitting their chromophores to touch one another yield suitably efficient energy transfer. In this regard, the rigidity and length of the linker are coupled parameters. Generally, shorter linkers (for example linkers having a length of about 5 to 12 Å) should include a greater degree of rigidity. Longer linkers (for example linkers having a length in the range of about 15 to 30 Å) can include a lesser degree of rigidity, or even no rigidity. Short, non-rigid (floppy) linkers should be avoided.

Rigidity can be achieved through the use of groups that have restricted angles of rotation about their bonds, for example, through the use of arylene or heteroarylene moieties, and/or alkylene moieties that comprise double and/or triple bonds. A variety of linkers useful for linking rhodamine and fluorescein dyes to one another in the context of energy transfer dyes are known in the art, and are described, for example, in U.S. Pat. No. 5,800,996, the disclosure of which is incorporated herein by reference. Specific examples of linkers useful for linking O-protected fluorescein or N-protected NH-rhodamine donors to N-protected NH-rhodamine acceptors in the label moieties described herein include, by way of example and not limitation, groups of the formula:

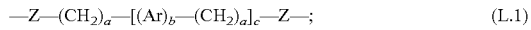 (L.1)

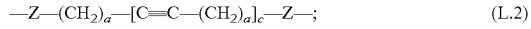 (L.2)

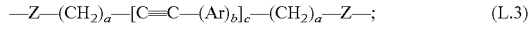 (L.3)

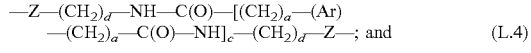 (L.4)

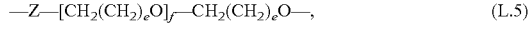 (L.5)

where each Z represents, independently of the others, a portion of a linkage contributed by a linking group $F^z$, as previously described, each a represents, independently of the others, an integer ranging from 0 to 4; each b represents, independently of the others, an integer ranging from 1 to 2; each c represents, independently of the others, an integer ranging from 1 to 5; each d represents, independently of the others, an integer ranging from 1 to 10; each e represents, independently of the others, an integer ranging from 1 to 4; each f represents, independently of the others, an integer ranging from 1 to 10; and each Ar represents, independently of the others, an optionally substituted monocyclic or polycyclic cycloalkylene, cycloheteroalkynene, arylene or heteroarylene group. Non-limiting exemplary embodiments of Ar include groups derived from lower cycloalkanes, lower cycloheteroalkanes, parent aromatic ring systems and parent heteroaromatic ring systems, as described previously. Specific, non-limiting exemplary embodiments of Ar include cyclohexane, piperazine, benzene, napthalene, phenol, furan, pyridine, piperidine, imidazole, pyrrolidine and oxadizole. Specific, non-limiting exemplary embodiments of linkers are illustrated in FIG. 2. In FIG. 2, $Z^1$ and $Z^2$ each represent, independently of one another, a portion of a linkage contributed by a functional group $F^z$, as previously described, and K is selected from —CH— and —N—. In some specific embodiments of the linkers illustrated in FIG. 2, one of $Z^1$ or $Z^2$ is —NH— and the other is selected from —O—, —C(O)— and —S(O)$_2$—.

In some embodiments, the linker linking the donor and acceptor dyes is an anionic linker as described in U.S. Pat. No. 6,811,979, the disclosure of which is incorporated herein by reference (see, e.g., the disclosure at Col. 17, line 25 through Col. 18, line 37 and FIGS. 1-17). Specific, non-limiting exemplary embodiments of suitable anionic linkers include the linkers of formulae (L.1) through (L.4), above, in which one or more of the Ar groups are substituted with one or more substituent groups having a negative charge under the conditions of use, such as, for example, at a pH in the range of about pH 7 to about pH 9. Specific, non-limiting examples of suitable substituent groups include phosphate esters, sulfate esters, sulfonate and carboxylate groups.

In some embodiments, the label moiety is of the formula (VI):

 (VI)

where A represents the N-protected NH-rhodamine acceptor, D represents the donor, for example, an N-protected NH-rhodamine or O-protected fluorescein donor, $Z^1$ and $Z^2$ represent portions of linkages provided by linking moieties comprising a functional group $F^z$, as previously described, and Sp represents a spacing moiety, as previously described. In some specific embodiments, A is selected from structural formulae A.1, A.2, A.3, A.4, A.5 and A.6 and D is selected from structural formulae D.1, D.2, D.3, D.4, D.5 and D.6, illustrated below. In some specific embodiments, A is selected from structural formulae A.7, A.8, A.9, A.10, A.11 and A.12 and D is selected from structural formulae D.7, D.8, D.9, D.10, D.11 and D.12, illustrated below.

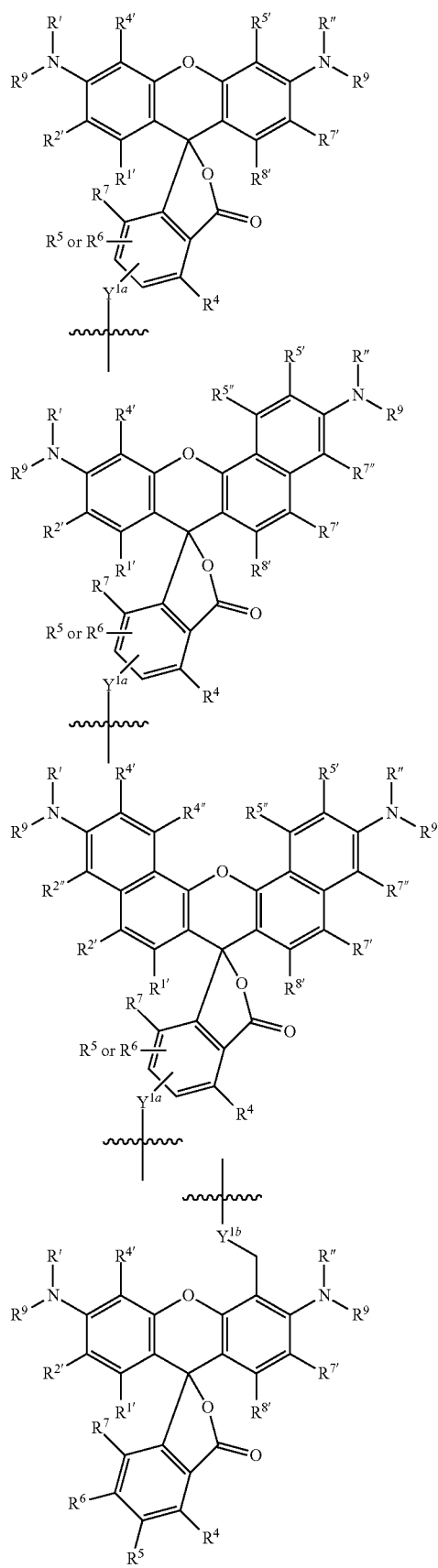
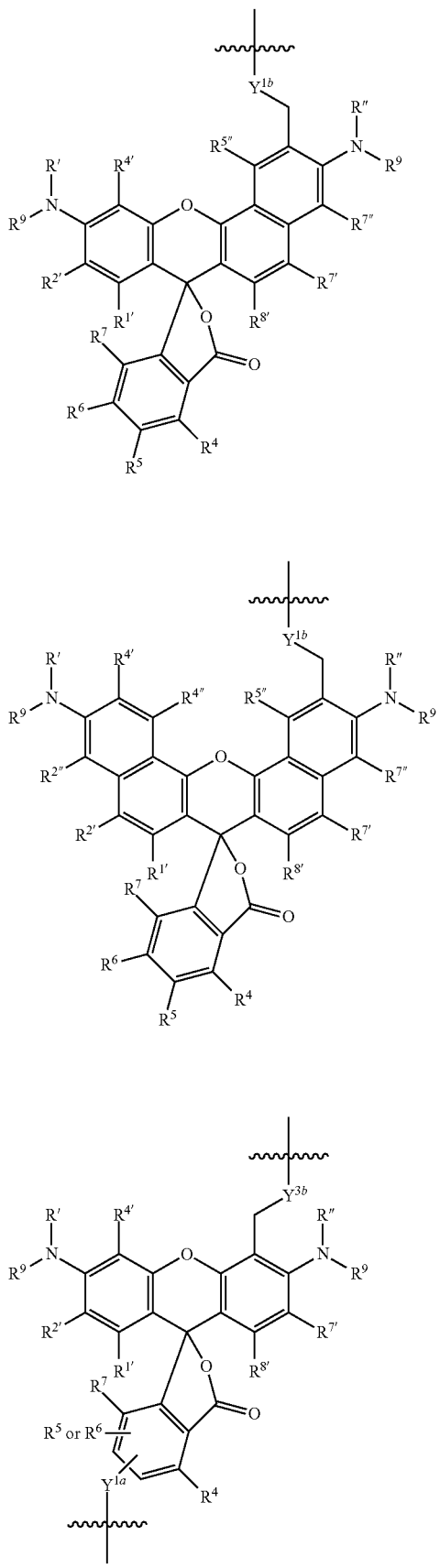

-continued
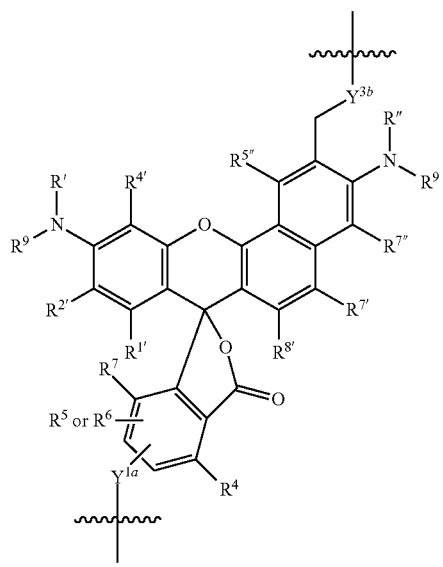
A.8
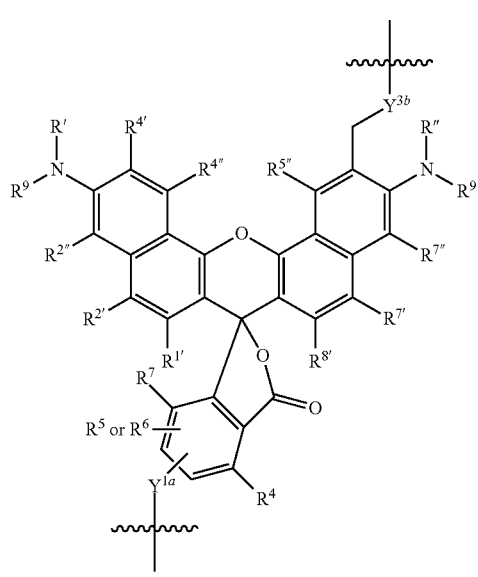
A.9
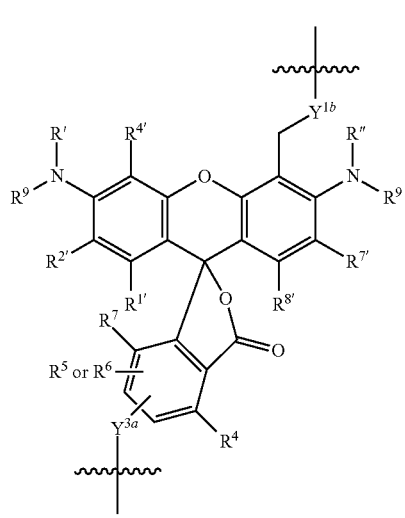
A.10
-continued
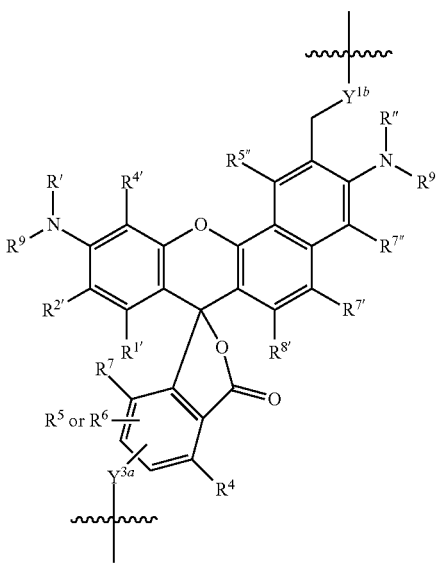
A.11
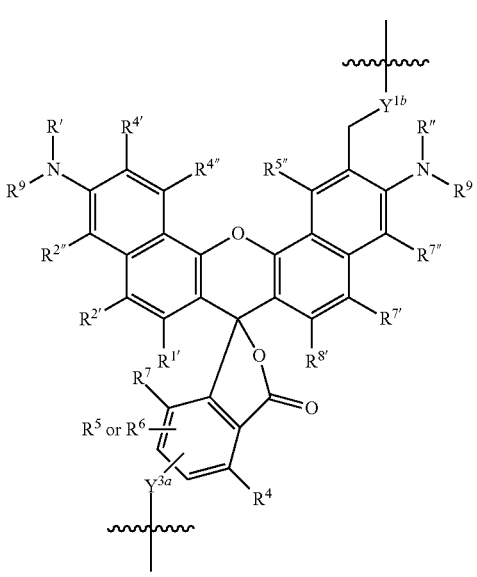
A.12
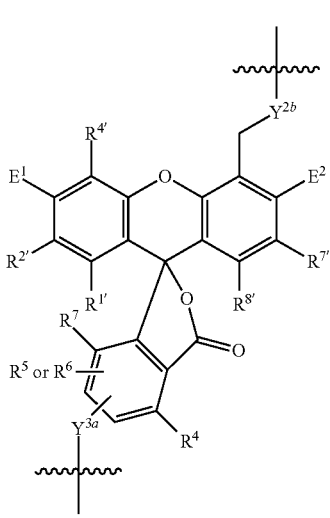
D.1

-continued
D.2 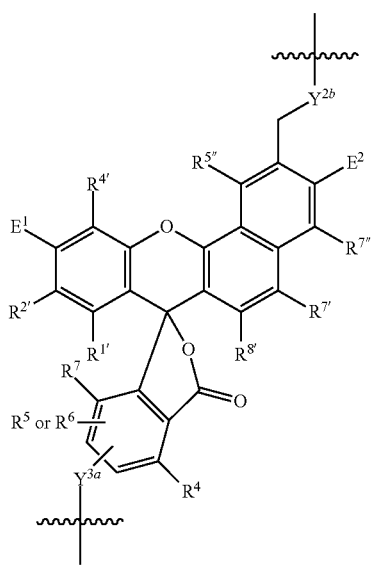
D.3 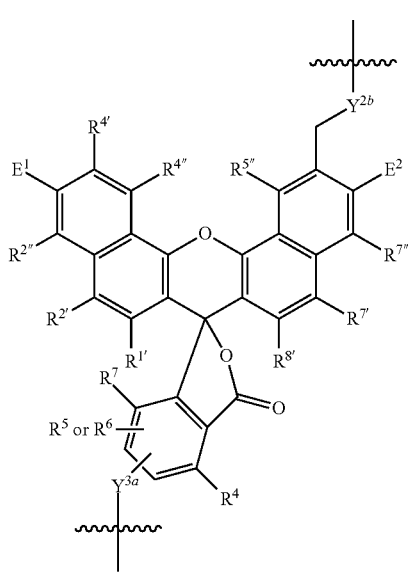
D.4 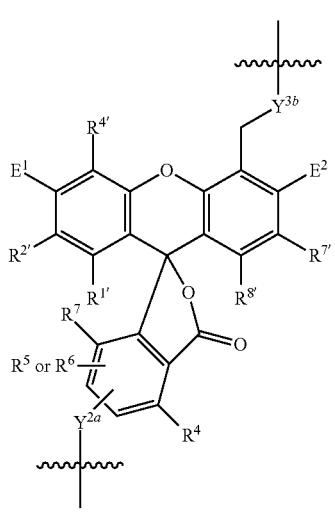
-continued
D.5 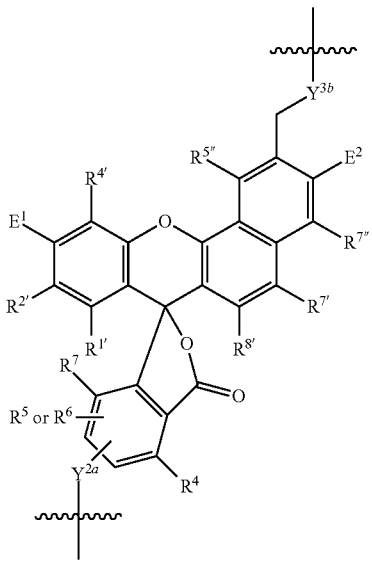
D.6 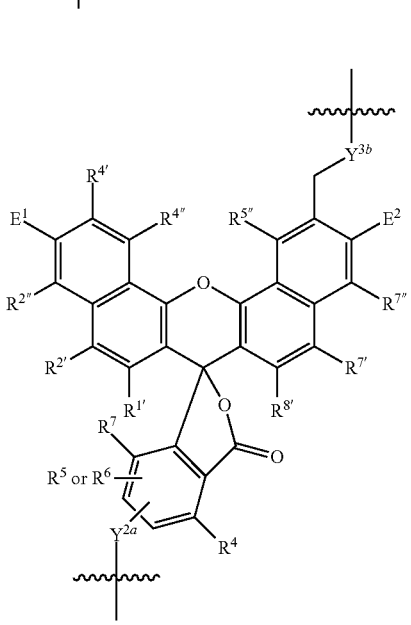
D.7 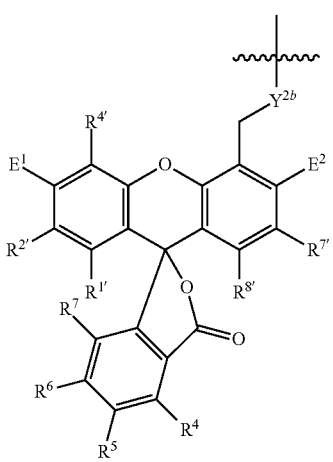

D.8
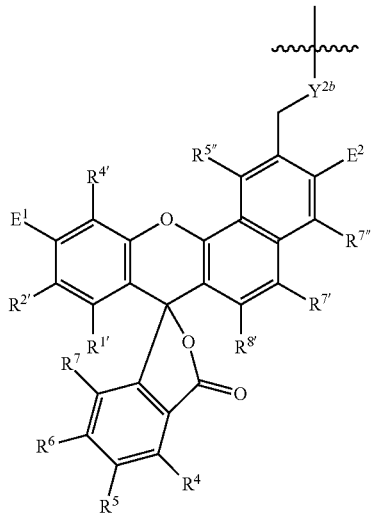

D.9
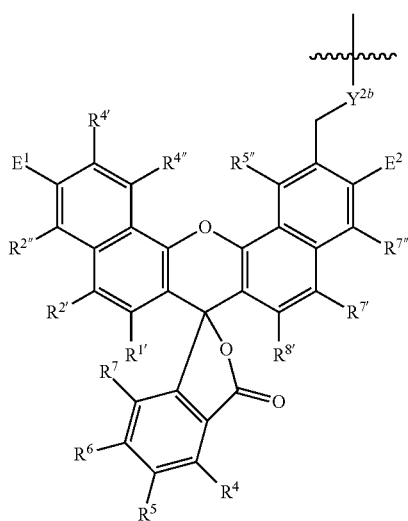

D.10
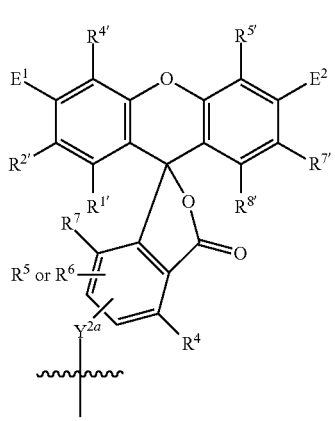

D.11
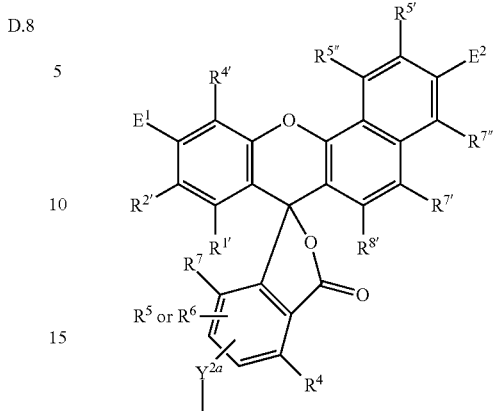

D.12
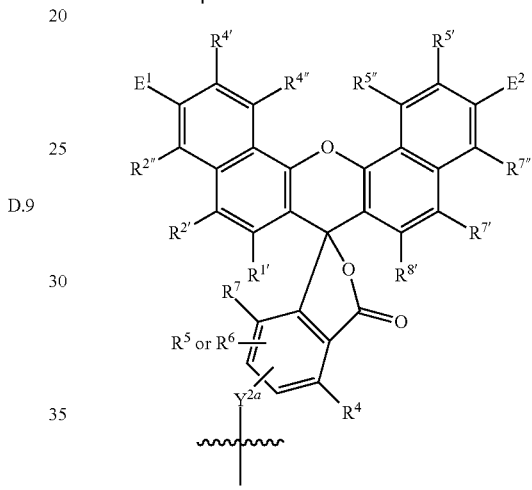

In structural formulae A.1-A.12 and D.1-D.12:
$E^1$ is selected from —NHR$^9$, —NR$^3$'R$^9$ and —OR$^{9b}$;
$E^2$ is selected from —NHR$^9$, —NR$^6$'R$^9$ and —OR$^{9b}$;
$R^{9b}$ is $R^9$;
$Y^{1a}$, $Y^{1b}$, $Y^{2a}$, $Y^{2b}$, $Y^{3a}$ and $Y^{3b}$ are each, independently of one another, selected from —O—, —S—, —NH—, —C(O)— and —S(O)$_2$—; and
R', R", R$^1$', R$^2$', R$^2$", R$^3$', R$^4$', R$^4$", R$^5$', R$^5$", R$^6$', R$^7$', R$^7$", R$^8$', R$^4$, R$^5$, R$^6$ and R$^7$ are as previously defined for structural formulae (IIIa), (IIIb) and (IIIc), with the proviso that when $E^1$ and $E^2$ are —OR$^{9b}$, then R$^1$' and R$^2$' and R$^7$' and R$^8$ may both include benzo and/or pyrido groups simultaneously.

In some specific embodiments of label moieties according to structural formula (VI), $Y^{1a}$, $Y^{2a}$ and $Y^{3a}$ are —NH—; $Y^{1b}$, $Y^{2b}$ and $Y^{3b}$ are selected from C(O)— and —S(O)$_2$—; Z' is selected from —C(O)— and —S(O)$_2$—; Z$^2$ is —NH— and Sp is a group selected from:

—(CH$_2$)$_a$—[Ar$_b$—(CH$_2$)$_a$]$_c$—      (Sp.1)

—(CH$_2$)$_a$—[C≡C—(CH$_2$)$_a$]$_c$—      (Sp.2)

—(CH$_2$)$_a$—[C≡C—(Ar)$_b$]$_c$—(CH$_2$)$_a$—      (Sp.3)

—(CH$_2$)$_d$—NH—C(O)—[(CH$_2$)$_a$—(Ar)—(CH$_2$)$_a$—C(O)—NH]$_c$—(CH$_2$)$_d$—; and      (Sp.3)

—[CH$_2$(CH$_2$)$_e$O]$_f$—CH$_2$(CH$_2$)—, where a, b, c, d, e, f and Ar are as previously defined.      (Sp.5)

In some specific embodiments of label moieties according to structural formula (VI), $R^9$ is selected from —C(O)CH$_3$ and C(O)CF$_3$ and $R^{9a}$ is —C(O)C(CH$_3$)$_3$.

5.5 Phosphate Ester Precursor Group

Many embodiments of the reagents described herein include a phosphate ester precursor group ("PEP"). When used in a step-wise synthesis to synthesize a labeled oligonucleotide, the PEP group is coupled to any available hydroxyl group, which may be the 5'-hydroxyl group of a nascent synthetic oligonucleotide, ultimately contributing, after any required oxidation and/or deprotection steps, a linkage linking the label moiety to the synthetic oligonucleotide. The linkage formed may be a phosphate ester linkage or a modified phosphate ester linkage as is know in the art.

A variety of different groups suitable for coupling reagents to primary hydroxyl groups to yield phosphate ester or modified phosphate ester linkages are well-known in the art. Specific examples include, by way of example and not limitation, phosphoramidite groups (see, e.g., Letsinger et al., 1969, J. Am. Chem. Soc. 91:3350-3355; Letsinger et al., 1975 J. Am. Chem. Soc. 97:3278; Matteucci & Caruthers, 1981, J. Am. Chem. Soc. 103:3185; Beaucage & Caruthers, 1981, Tetrahedron Lett. 22:1859; the disclosures of which are incorporated herein by reference), 2-chlorophenyl- or 2,5-dichlorophenyl-phosphate groups (see, e.g., Sproat & Gait, "Solid Phase Synthesis of Oligonucleotides by the Phosphotriester Method," In: *Oligonucleotide Synthesis, A Practical Approach*, Gait, Ed., 1984, IRL Press, pages 83-115), the disclosures of which are incorporated herein by reference), and H-phosphonate groups (see, e.g., Garegg et al., 1985, Chem. Scr. 25:280-282; Garegg et al., 1986, Tet. Lett. 27:4051-4054; Garegg et al. 1986, Tet. Lett. 27:4055-4058; Garegg et al., 1986, Chem. Scr. 26:59-62; Froehler & Matteucci, 1986, Tet. Lett. 27:469-472; Froehler et al., 1986, Nucl. Acid Res. 14:5399-5407, the disclosures of which are incorporated herein by reference). In a specific embodiment, the PEP group is a phosphoramidite group of the formula (P.1):

wherein:
$R^{20}$ is selected from a linear, branched or cyclic saturated or unsaturated alkyl containing from 1 to 10 carbon atoms, 2-cyanoethyl, an aryl containing from 6 to 10 ring carbon atoms and an arylalkyl containing from 6 to 10 ring carbon atoms and from 1 to 10 alkylene carbon atoms; and
$R^{21}$ and $R^{22}$ are each, independently of one another, selected from a linear, branched or cyclic, saturated or unsaturated alkyl containing from 1 to 10 carbon atoms, an aryl containing from 6 to 10 ring carbon atoms and an arylalkyl containing from 6 to 10 ring carbon atoms and from 1 to 10 alkylene carbon atoms, or, alternatively, $R^{21}$ and $R^{22}$ are taken together with the nitrogen atom to which they are bonded to form a saturated or unsaturated ring that contains from 5 to 6 ring atoms, one or two of which, in addition to the illustrated nitrogen atom, can be heteroatom selected from O, N and S.

In a specific embodiment, $R^{20}$ is 2-cyanoethyl and $R^{21}$ and $R^{22}$ are each isopropyl.

5.6 Synthesis Handles

Many embodiments of the reagents described herein include one or more synthesis handles that provide, after suitable deprotection, if necessary, sites that can be used for the attachment of additional groups or moieties to the synthetic labeled oligonucleotide. The groups can be attached to a synthesis handle during the course of synthesizing the labeled oligonucleotide, or, alternatively, the synthesis handle can be deprotected post-synthesis to reveal a functional group to which additional groups or moieties can be attached. For example, a synthesis handle could comprise a primary amine group that is protected with a protecting group that is stable to the conditions used to carry out the synthesis of the labeled oligonucleotide. Removal of the protecting group following synthesis, either concurrently with, or separately from, the removal of the various other protecting groups on the synthetic oligonucleotide, provides a primary amino group to which additional groups and/or moieties can be attached.

A variety of different types of reactive groups protected with protecting groups suitable for use in oligonucleotide synthesis are known in the art, and include by way of example and not limitation, amino groups (protected with, for example, trifluoroacetyl or 4-monomethoxytrityl groups), hydroxyl groups (protected with, for example, 4,4'-dimethoxytrityl groups), thiol groups (protected with, for example, trityl or alkylthiol groups) and aldehyde groups (protected with, for example, an acetal protecting group). All of these protected reactive groups can comprise the synthesis handle of the reagents described herein.

In some embodiments, the synthesis handle comprises a protected primary hydroxyl of the formula —OR$^e$, where R$^e$ represents an acid-labile protecting group that can be selectively removed during the course of synthesizing an oligonucleotide. Acid labile protecting groups suitable for protecting primary hydroxyl groups in the context of oligonucleotide synthesis are known in the art, and include, by way of example and not limitation, triphenylmethyl (trityl), 4-monomethoxytrityl, 4,4'-dimethoxytrityl, 4,4',4"-trimethoxytrityl, bis(p-anisyl)phenylmethyl, naphthyldiphenylmethyl, p-(p'-bromophenacyloxy)phenyldiphenylmethyl, 9-anthryl, 9-(9-phenyl)xanthenyl and 9-(9-phenyl-10-oxo) anthryl. All of these groups can be removed by treatment with mild acid, such as by treatment with 2.5% or 3% di- or trichloro acid and in dichloromethane. Methods of protecting primary hydroxyl groups with the above-listed acid-labile protecting groups are well-known.

5.7 Solid Supports

Many embodiments of the reagents described herein comprise solid supports to which the other moieties and/or groups are attached. The solid supports are typically activated with functional groups, such as amino or hydroxyl groups, to which linkers bearing linking groups suitable for attachment of the other moieties are attached.

A variety of materials that can be activated with functional groups suitable for attachment to a variety of moieties and linkers, as well as methods of activating the materials to include the functional groups, are known in the art, and include by way of example, controlled pore glass, polystyrene and graft co-polymers. Any of these materials be used as solid supports in the reagents described herein.

5.8 Synthesis Regents Useful for Terminal Hydroxyl Labeling

Some embodiments of the synthesis reagents described herein are described by structural formula (VII):

LM-L-PEP                    (VII)

where LM represents a label moiety as described herein, L represents an optional linker as described herein and PEP represents a phosphate ester precursor group as described herein. The reagents can include additional groups or moieties, such as synthesis handles. In some embodiments, the synthesis reagents comprise a label moiety and a PEP group, and do not include additional moieties or groups. Such synthesis reagents can be coupled to a hydroxyl group during the step-wise synthesis of an oligonucleotide, and are useful for, among other things, attaching a label moiety to a terminal hydroxyl group of a synthetic oligonucleotide, which is commonly the 5'-hydroxyl.

The PEP group can be attached directly to the label moiety, or it may be attached to the label moiety with the aid of a linker. As PEP groups are generally linked to molecules by coupling suitable reagents to primary hydroxyl groups, in embodiments in which the PEP group is attached directly to the label moiety, the label moiety should include a substituent group that comprises a primary hydroxyl group. In embodiments in which the PEP group is linked to the label moiety with the aid of a linker, the linker synthon should include a linking group suitable for forming a linkage with a linking group on the label moiety synthon and a primary hydroxyl group suitable for attachment to the PEP group. Suitable linker synthons include, but are not limited to, synthons of the formula $F^z$-Sp-OH, where $F^z$ is a functional group complementary to a functional group on the label moiety synthon and Sp represents a spacing moiety. The spacing moiety can comprise any combination of atoms and/or functional groups stable to the conditions that will be used to synthesize and deprotect the labeled synthetic oligonucleotide. Non-limiting exemplary linkers are illustrated in FIG. 2, where $Z^2$ is O. In some embodiments, Sp is an optionally substituted alkylene chain that contains from 1 to 10 chain atoms. In a specific embodiment, Sp is an unsubstituted alkylene chain containing from 1 to 9 carbon chain atoms.

In some embodiments, the synthesis reagents are compounds according to structural formula (VII) in which:
  LM is one of the embodiments of label moieties specifically exemplified above;
  L is selected from —Z—$(CH_2)_{3-6}$—O—, —Z—$(CH_2)_a$—[(Ar)_b—$(CH_2)_a]_c$—O—, —Z—$(CH_2)_a$—[C≡C—$(CH_2)_a]_c$—O—, —Z—$(CH_2)_a$—[C≡C—$(Ar)_b]_c$—$(CH_2)_a$—O—, —Z—$(CH_2)_d$—NH—C(O)—[$(CH_2)_a$—(Ar)—$(CH_2)_a$—C(O)—NH]_c—$(CH_2)_d$—O—, —Z—[$CH_2(CH_2)_eO]_f$—$CH_2(CH_2)_eO$— and one of the linkers illustrated in FIG. 2 in which $Z^2$ is O; and
  PEP is a phosphoramidite group, such as for example, a phosphoramidite group of structural formula P.1, as described above. In some specific embodiments, Z in linker L is —NH—.

Figure 4:
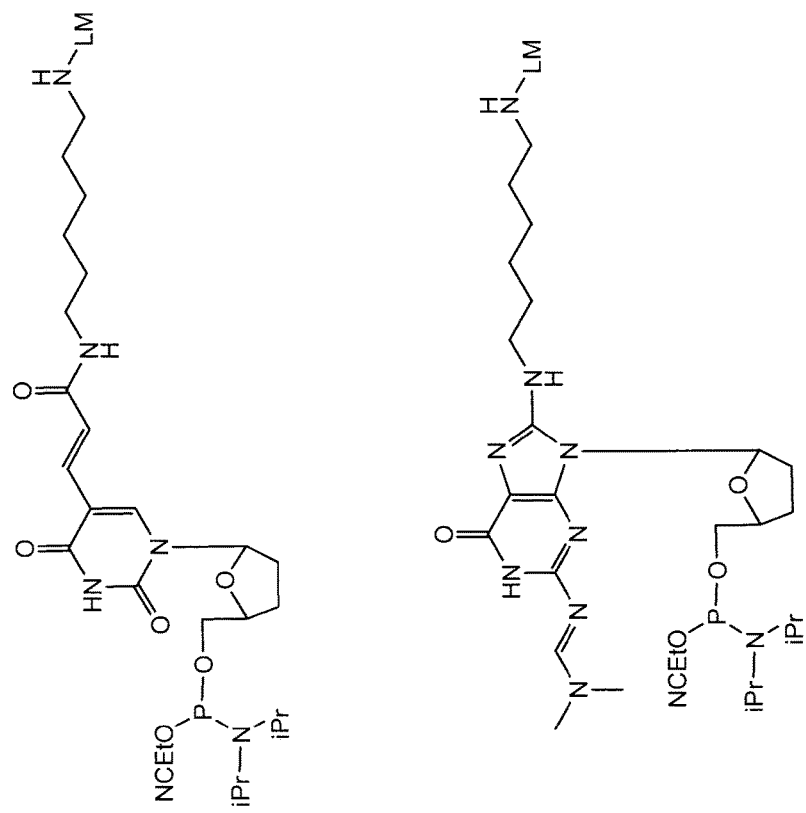
Figure 5:
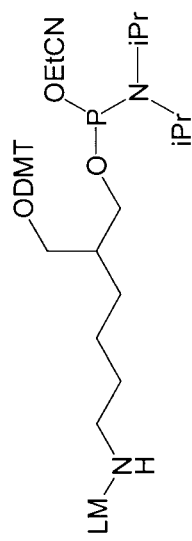
Figure 6:
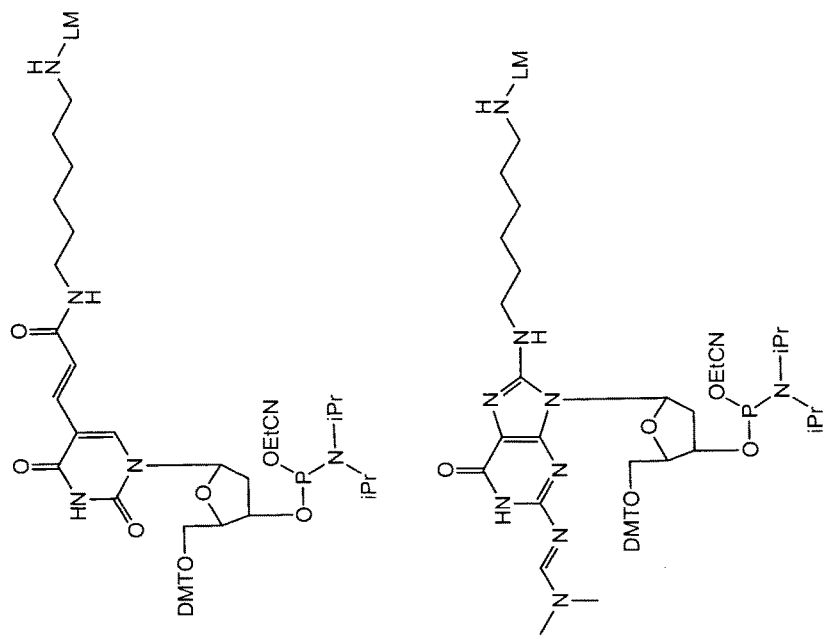

In some embodiments, the linker in synthesis reagents according to structural formula (VII) comprises a nucleoside, such that the synthesis reagent is nucleosidic. In some embodiments, nucleosidic synthesis reagents are compounds according to structural formula (VII.1):

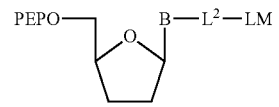
(VII.1)

where PEP represents the phosphate ester precursor group, B represents a nucleobase, LM represents the label moiety and $L^2$ represents a linker linking nucleobase B to linker LM. The features and properties of nucleobase B and linker L are described in more detail, below. Non-limiting exemplary nucleosidic synthesis reagents according to structural formula (VII.1) are illustrated in FIG. 4.

An exemplary scheme for synthesizing embodiments of synthesis reagents in which the PEP group is linked to the label moiety via an optional linker is provided in Scheme (I), below, where the various R, $F^y$, $F^z$, Y, Z and $S_p$ groups are as previously defined:

Scheme (I)

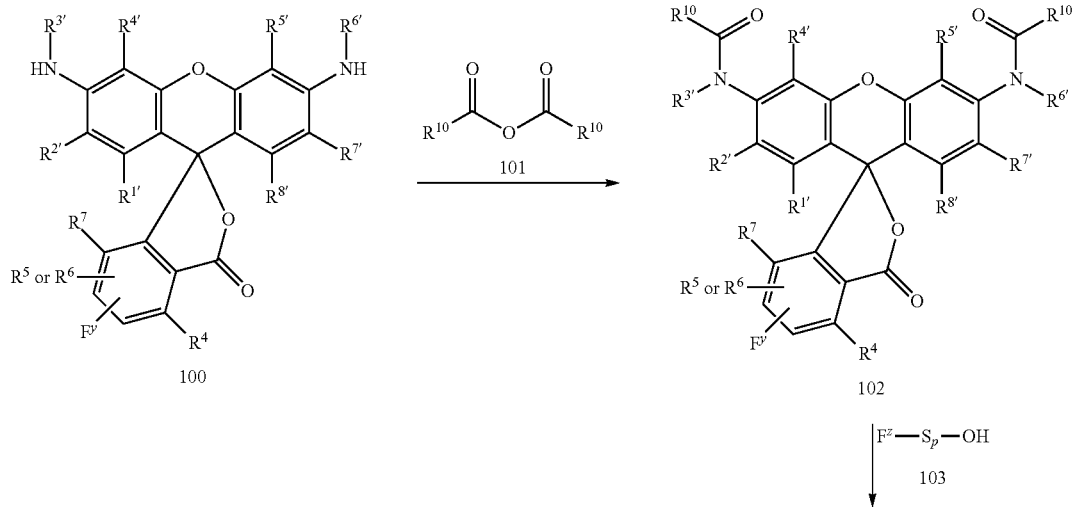

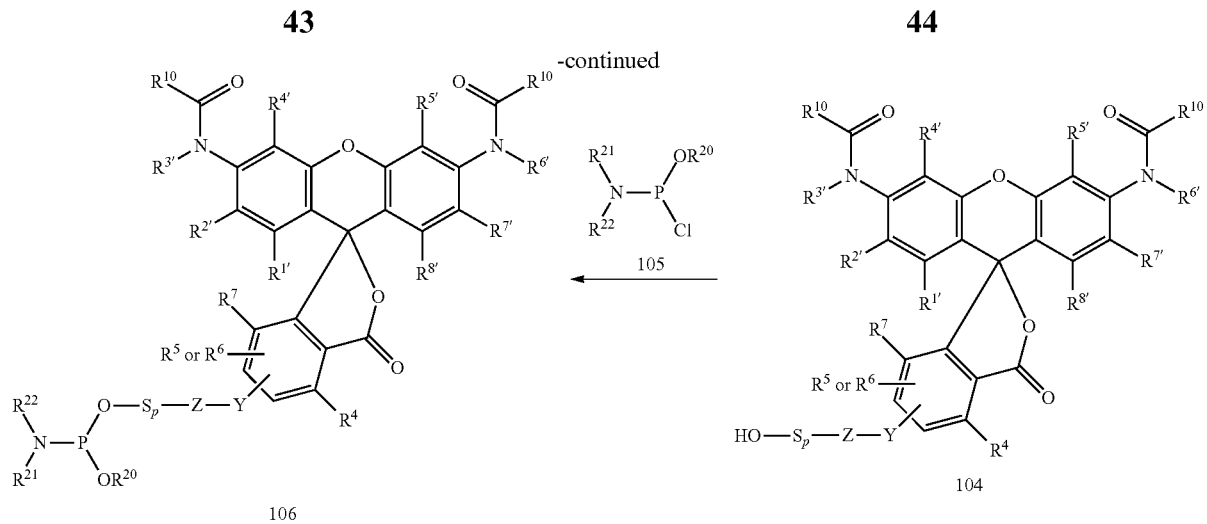

In Scheme (I) parent NH-rhodamine synthon 100, which includes a linking group that comprises functional group F$^y$, is acetylated with anhydride 101 to yield N-acetyl-protected NH-rhodamine synthon 102. Synthon 102 is then coupled to linker synthon 103 to yield compound 104. Depending upon the identity of F$^y$, synthon 102 may require activation prior to coupling. For example, if F$^y$ is a carboxyl group, it can be activated as an ester, such as an NHS ester, prior to coupling. In compound 104, —Y—Z— represents the linkage formed by complementary functional groups F$^y$ and F$^z$, where Y represents the portion contributed by F$^y$ and Z represents the portion contributed by F$^z$, as previously described. Compound 104 is then reacted with PEP synthon 105, which in the specific embodiment illustrated is a phosphine, to yield phosphoramidite synthesis reagent 106.

5.9 Synthesis Reagents Useful for Internal or 3'-End Labeling

The synthesis reagents described herein may optionally include one or more synthesis handles useful for the attachment of additional groups and/or moieties. Synthesis reagents that include a synthesis handle of the formula —OR$^e$, where R$^e$ represents an acid-labile protecting group as previously described, provide a primary hydroxyl group to which additional nucleotides can be attached. As a consequence, synthesis reagents that include such a synthesis handle can be used to label synthetic oligonucleotides at the 5'-hydroxyl, the 3'-hydroxyl or at one or more internal positions. They can also be coupled to one another, or to other phosphoramidite labeling reagents, permitting the synthesis of oligonucleotides containing a plurality of label moieties.

The label moiety, PEP group and synthesis handle —OR$^e$ comprising the synthesis reagent can be linked together in any fashion and/or orientation that permits them to perform their respective functions. As a specific example, the PEP group and synthesis handle can each be linked to the label moiety, optionally via linkers. In some embodiments, such synthesis reagents are compounds according to structural formula (VIII):

$$R^eO\text{-L-LM-L-PEP} \tag{VIII}$$

where each L represents, independently of the other, an optional linker, LM represents the label moiety and PEP represents the phosphate ester precursor group. Non-limiting examples of suitable protecting groups R$^e$, linkers L, label moieties LM and phosphate ester precursor groups include those specifically exemplified above.

As another specific example, the PEP group and synthesis handle —OR$^e$ may be attached to a branched linker that is attached to the label moiety. In some embodiments, such synthesis reagents are compounds according to structural formula (IX):

where L represent a linker, LM represents the label moiety and PEP represents the phosphate ester precursor group.

Figure 3:
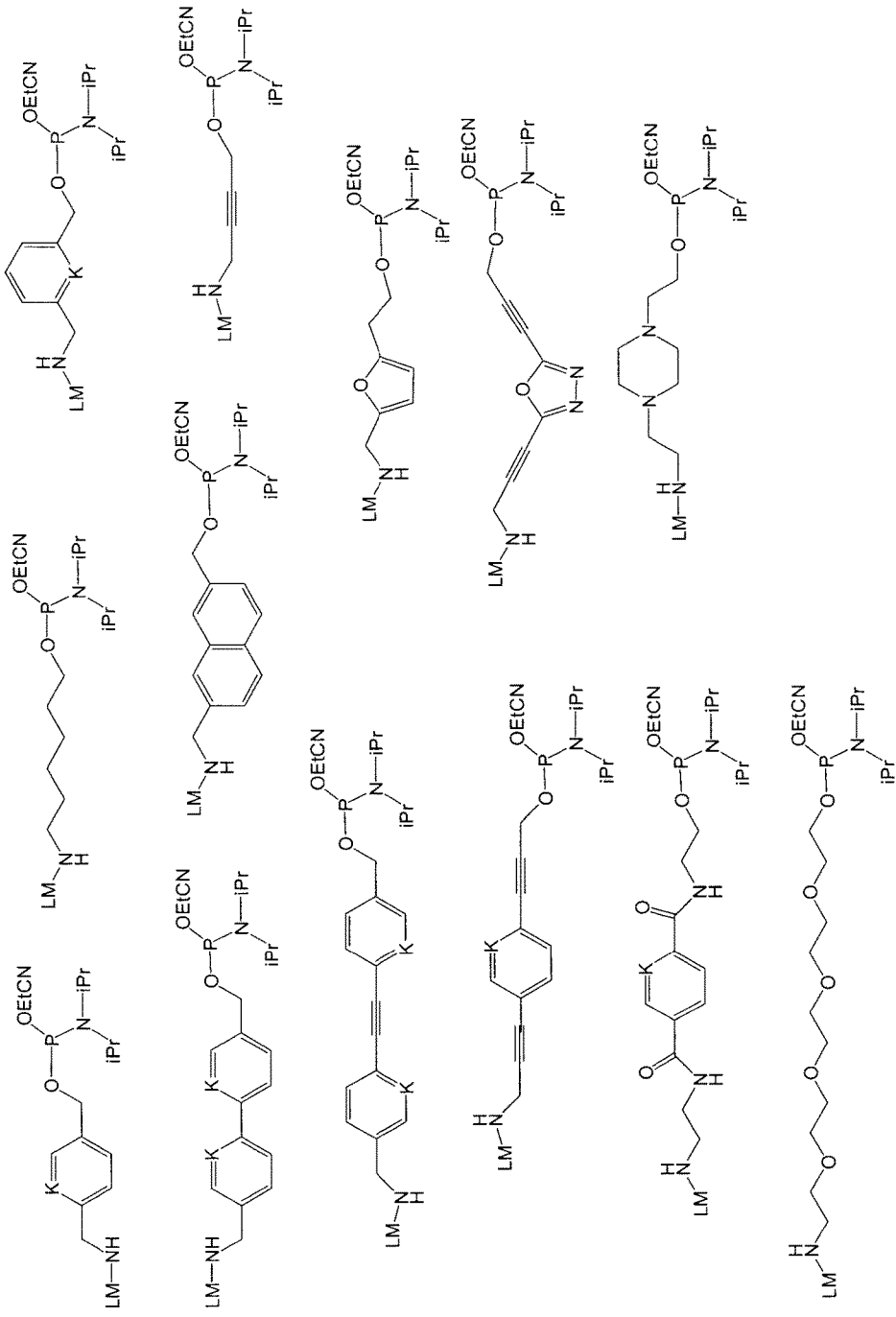

In a specific embodiment, synthesis reagents according to structural formula (IX) are compounds according to structural formula (IX.1):

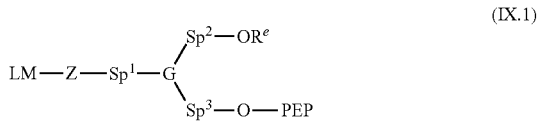

where LM represents the label moiety, —Z— represents a portion of a linkage contributed by a functional F$^z$ on the linker, Sp$^1$, Sp$^2$ and Sp$^3$, which can be the same or different, each represent spacing moieties, G represents CH, N, or a group comprising and arylene, phenylene, heteroarylene, lower cycloalkylene, cyclohexylene, and/or lower cycloheteroalkylene, and PEP represents the phosphate ester precursor group. In some embodiments, LM is one of the embodiments of label moieties specifically exemplified above, Sp$^1$, Sp$^2$ and Sp$^3$ are each, independently of one another, selected from an alkylene chain containing from 1 to 9 carbon atoms, Sp.1, Sp.2, Sp.3, Sp.4 and Sp.5 (defined above), and/or PEP is a phosphoramidite group according to structural formula P.1, supra. Non-limiting specific embodiments of exemplary synthesis reagents according to structural formula (IX.1) are illustrated in FIGS. 3 and 4.

In some embodiments, the synthesis handle —OR$^e$ is provided by a nucleoside, such that the synthesis reagent is nucleosidic. In such nucleosidic synthesis reagents, the label moiety is typically linked to the nucleobase of the nucleoside by way of a linker, and any exocyclic functional groups on the nucleobase that are reactive under the conditions used to synthesize the labeled oligonucleotide, such as, for example, exocyclic amines, are protected.

The nucleoside can be any nucleoside that can be suitably protected for use in the synthesis of oligonucleotides, and may comprise a 2'-deoxyribose sugar moiety, a 3'-deoxyribose sugar moiety (useful for synthesizing labeled oligonucleotides including a 2'-5' internucleotide linkage), a suitably protected ribose moiety, a substituted version of any of these ribose moieties, or even a non-ribose sugar moiety.

In some embodiments, such nucleosidic synthesis reagents are compounds according to structural formulae (IX.2), (IX.3), (IX.4) and (IX.5):

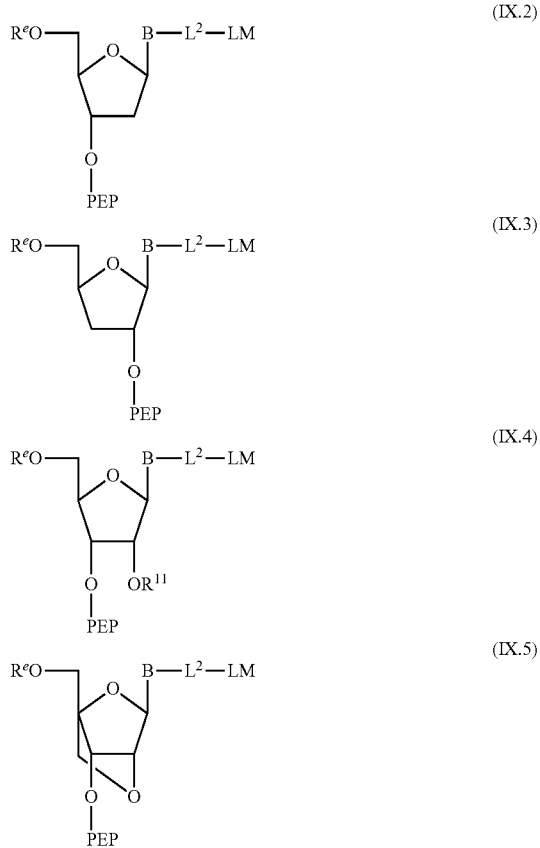

wherein LM represents the label moiety, B represents a suitably protected nucleobase, $L^2$ represents a linker linking the label moiety to the nucleobase, $R^e$ represents the acid-labile protecting group, PEP represents the phosphate ester precursor group, O is an oxygen atom and, in structural formula (IX.4), $R^{11}$ represents a 2'-hydroxyl protecting group.

In the synthesis reagents according to structural formulae (VII.1), (IX.2), (IX.3), (IX.4) and (IX.5), the nucleobase B can be virtually any heterocycle useful for incorporation into oligonucleotides. For example, the nucleobase may be one of the genetically encoding purines (adenine or guanine), one of the genetically encoding pyrimidines (cytosine, uracil or thymine), analogs and/or derivatives of the genetically encoding purines and/or pyrimidines (e.g., 7-deazaadenine, 7-deazaguanine, 5-methylcytosine), non-genetically encoding purines and/or pyrimidines (e.g., inosine, xanthene and hypoxanthene) or other types of heterocycles. A wide variety of heterocycles useful for incorporating into oligonucleotides are known in the art and are described, for example, in *Practical Handbook of Biochemistry and Molecular Biology*, Fasman, Ed., 1989, CRC Press (see, e.g., pages 385-393 and the references cited therein), the disclosures of which are incorporated herein by reference. All of these various heterocycles, as well as those that are later discovered, can be included in the nucleosidic synthesis reagents described herein.

When B is a purine in the synthesis reagents according to structural formulae (VII.1), (IX.2), (IX.3), (IX.4) and (IX.5), the illustrated sugar moiety is typically attached to the N9 position of the purine, and when B is a pyrimidine, the illustrated sugar moiety is typically attached at the N1 position of the pyrimidine. Attachment sites for other nucleobases will be apparent to those of skill in the art.

Any exocyclic amine or other reactive group(s) on the nucleobase are protected with protecting groups that are stable to the synthesis conditions used to synthesize the labeled oligonucleotide. A variety of groups that are suitable for protecting the exocyclic amine groups of nucleoside nucleobases in the context of oligonucleotide synthesis are well-known in the art, as are methods of preparing such protected nucleosides.

For example, groups that have been used to protect the exocyclic amine of adenine include benzyol (Bz), phenoxyacetyl (Pac) and isobutyryl (iBu). Groups that have been used to protect the exocyclic amine of cystosine include acetyl (Ac) and Bz. Groups that have been used to protect the exocyclic amine of guanine include iBu, dimethylformamide (Dmf) and 4-isopropyl-phenoxyacetyl (iPr-Pac). All of these protecting groups can be removed by treatment with ammonium hydroxide at 55-65° C. for 2-3 hr. However, certain of these protecting groups can be removed under milder conditions. For example, cleavage of the protecting groups from $A^{iBu}$, $A^{Pac}$, $C^{Ac}$ and $G^{iPr-Pac}$ can be effected in 4-17 hrs at room temperature with ammonium hydroxide, or with 0.05M potassium carbonate in methanol, or treatment with 25% t-butylamine in $H_2O$/EtOH. As some of the NH-rhodamine and/or other dyes comprising the reagents described herein may not be stable to the harsher deprotection conditions required by other protecting groups, nucleosidic reagents which utilize protecting groups that can be removed under these milder deprotection conditions are preferred.

The linker $L^2$ linking the label moiety LM to the nucleobase B may be attached to any position of the nucleobase. In some embodiments, when B is a purine, the linker is attached to the 8-position of the purine, when B is a 7-deazapurine, the linker is attached to the 7-position of the 7-deazapurine, and when B is a pyrimidine, the linker is attached to the 5-position of the pyrimidine.

In some embodiments, linkers $L^2$ useful for attaching LM to a nucleobase comprise an acetylenic or alkenic amino linkage, such as, for example, a linkage selected from —C≡C—CH$_2$—NH—, —C≡C—C(O)—, —CH═CH—NH—, —CH═CH—C(O)—, —C≡C—CH$_2$—NH—C(O)—(CH$_2$)$_{1-6}$—NH—, and —CH═CH—C(O)—NH—(CH$_2$)$_{1-6}$—NH—C(O)—, a propargyl-1-ethoxyamino linkage, such as, for example, a linkage having the formula —C≡CH—CH$_2$—O—CH$_2$CH$_2$—[O—CH$_2$CH$_2$]$_{0-6}$—NH— or a rigid linkage, such as for example, a linkage selected from —C≡C—C≡C—CH$_2$—O—CH$_2$CH$_2$—[O—CH$_2$CH$_2$]$_{0-6}$—NH—, —C≡C—(Ar)$_{1-2}$—C≡C—

CH₂—O—CH₂CH₂—[O—CH₂CH₂]₀₋₆—NH—,
—C≡C—(Ar)₁₋₂—O—CH₂CH₂—[O—CH₂CH₂]₀₋₆—NH— and —C≡C—(Ar)₁₋₂—O—CH₂CH₂—[O—CH₂CH₂]₀₋₆—NH—, where Ar is as defined previously.

In some embodiments, linkers L² useful for attaching LM to a purine nucleobase comprise an alkylamine, such as, for example, a linkage of the formula —NH—(CH₂)₁₋₆—NH—.

In some embodiments, linkers L² useful for attaching LM to a purine or pyrimidine nucleobase are anionic linkers as described in U.S. Pat. No. 6,811,979, the disclosure of which is incorporated herein by reference (see, e.g., the disclosure at Col. 17, line 25 through Col. 18, line 37 and FIGS. 1-17).

Methods of synthesizing nucleosides derivatized with linkers such as those described above that are suitable for incorporating into the reagents described herein are described, for example, in Hobbs et al., 1989, J. Org. Chem. 54:3420; U.S. Pat. No. 5,151,507 to Hobbs et al., U.S. Pat. No. 5,948,648 to Khan et al.; and U.S. Pat. No. 5,821,356 to Khan et al, the disclosures of which are incorporated herein by reference. The derivatized nucleosides can be used as synthons to synthesize nucleosidic synthesis reagents as will be described in more detail, below.

Specific exemplary embodiments of linker-derivatized nucleobases that may comprise the nucleosidic reagents described herein are illustrated below:

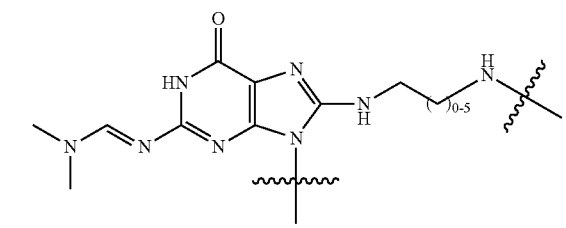

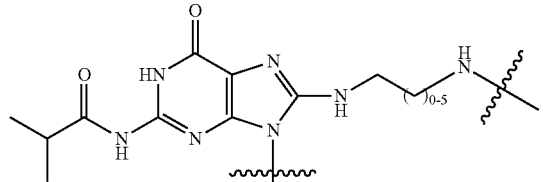

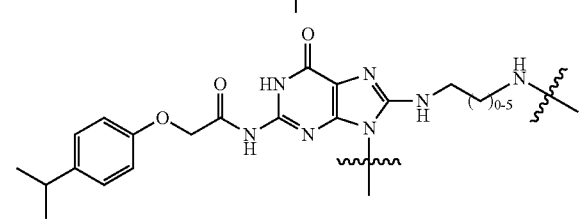

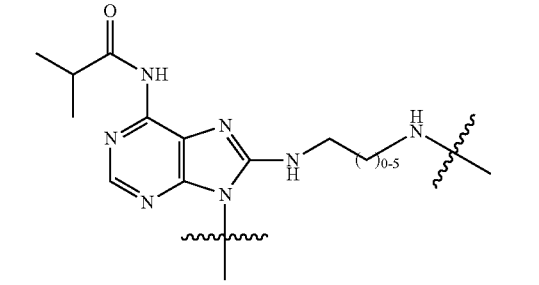

-continued

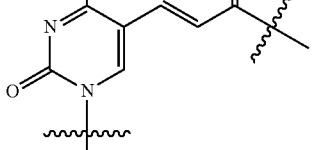

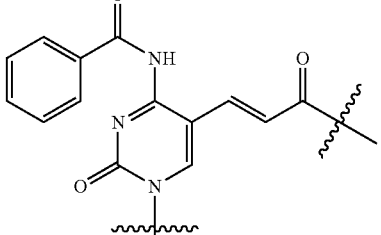

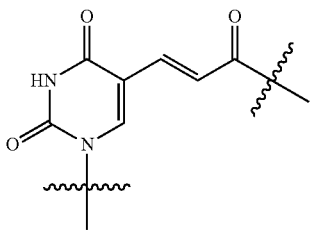

-continued

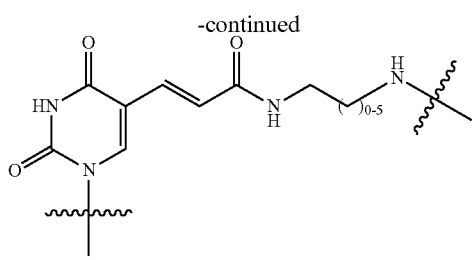

Nucleosidic synthesis reagents can be prepared from linker-derivatized nucleoside synthons as illustrated in Scheme (II), below:

by treatment with PEP synthon 105, which in this specific example illustrated is a phosphine (see Scheme (I), supra) yields nucleosidic synthesis reagent 114. Specific conditions for carrying out the various synthetic steps illustrated above are well known. Non-nucleosidic synthesis reagents that include a synthesis handle, such as a synthesis handle of the formula —$OR^e$, can be prepared by routine adaptation of Scheme (II).

5.10 Solid Support Reagents

Many embodiments of the reagents described herein include solid supports. Such reagents generally comprise a solid support, a label moiety as described herein and a

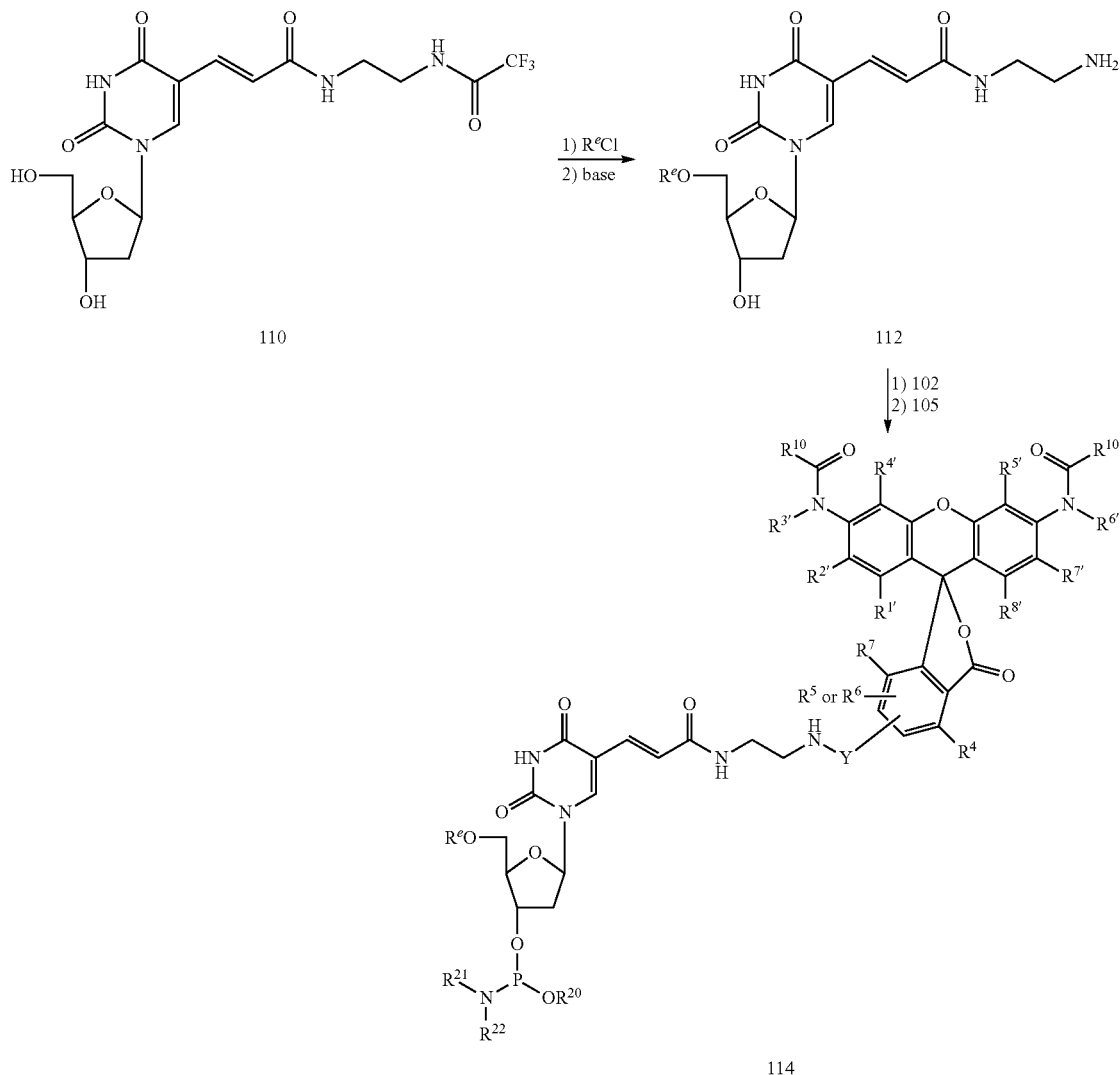

In Scheme (II), linker-derivatized nucleoside synthon 110 is protected at the 5'-hydroxyl with an acid-labile protecting group, which is illustrated in the Scheme with exemplary chloride reagent $R^eCl$, where $R^e$ is as previously defined. Treatment with base to remove the trifluoroacetyl protecting group yields synthon 112. Reaction of synthon 112 with label moiety synthon 102 (see Scheme (I), supra, followed synthesis handle, and may include additional groups or moieties, such as additional label moieties, quenching moieties, synthesis handles and/or groups useful for, among other things, stabilizing oligonucleotide duplexes, such as, for example, agents that intercalate between base pairs (intercalating agents) and agent that bind the duplex minor groove (minor groove binding, or MGB, agents). The solid support, label moiety, synthesis handle and any optional additional moieties may be linked to one another in any fashion or orientation that permits them to perform their respective functions.

In some embodiments, the solid support is attached to the remainder of the reagent via a linker Linkers attaching solid supports to the remainder of the reagent typically include linkages that are selectively cleavable under specified conditions such that, following synthesis, the synthesized labeled oligonucleotide can be released from the solid support. In some embodiments, the linkages are labile to the conditions used to deprotect the synthetic labeled oligonucleotide, such that the oligonucleotide is deprotected and cleaved from the solid support in a single step. Such linkers typically include ester linkages, but may include other linkages, such as, for example, carbonate esters, diisopropylsiloxy ethers, modified phosphates esters, etc.

Figure 7:
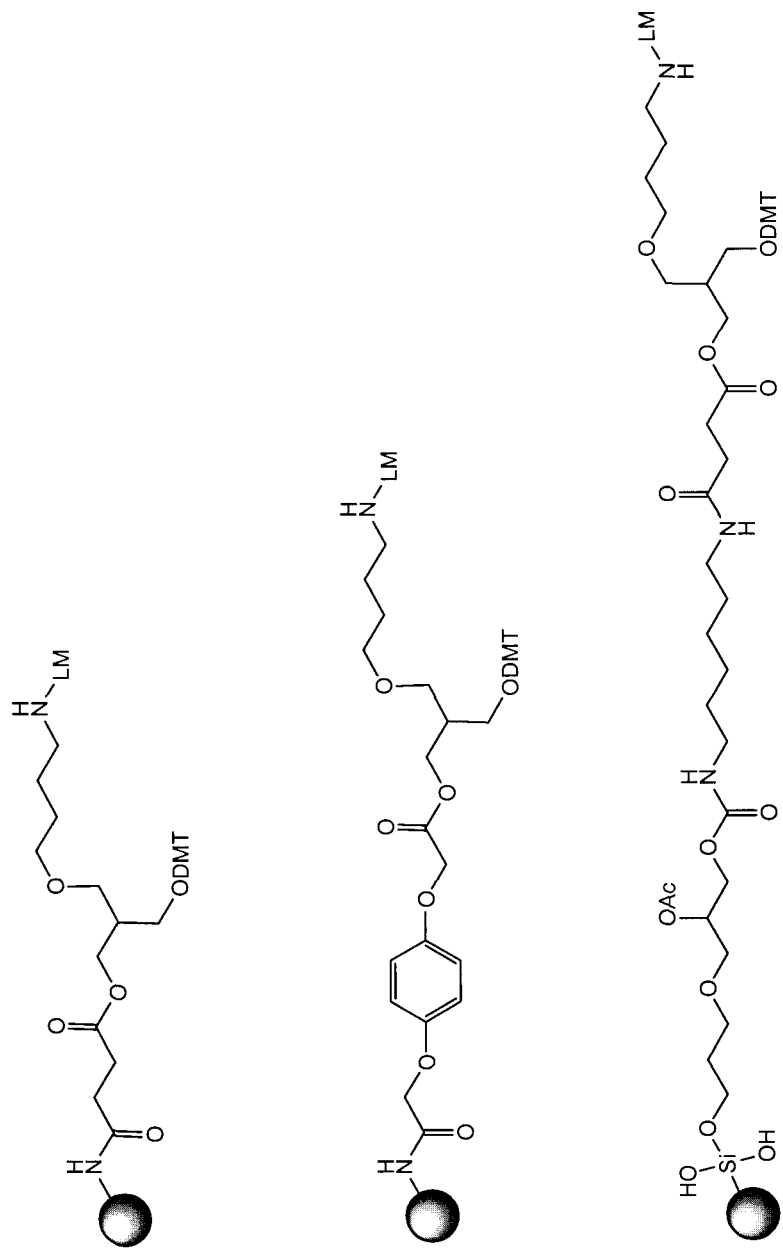
Figure 8:
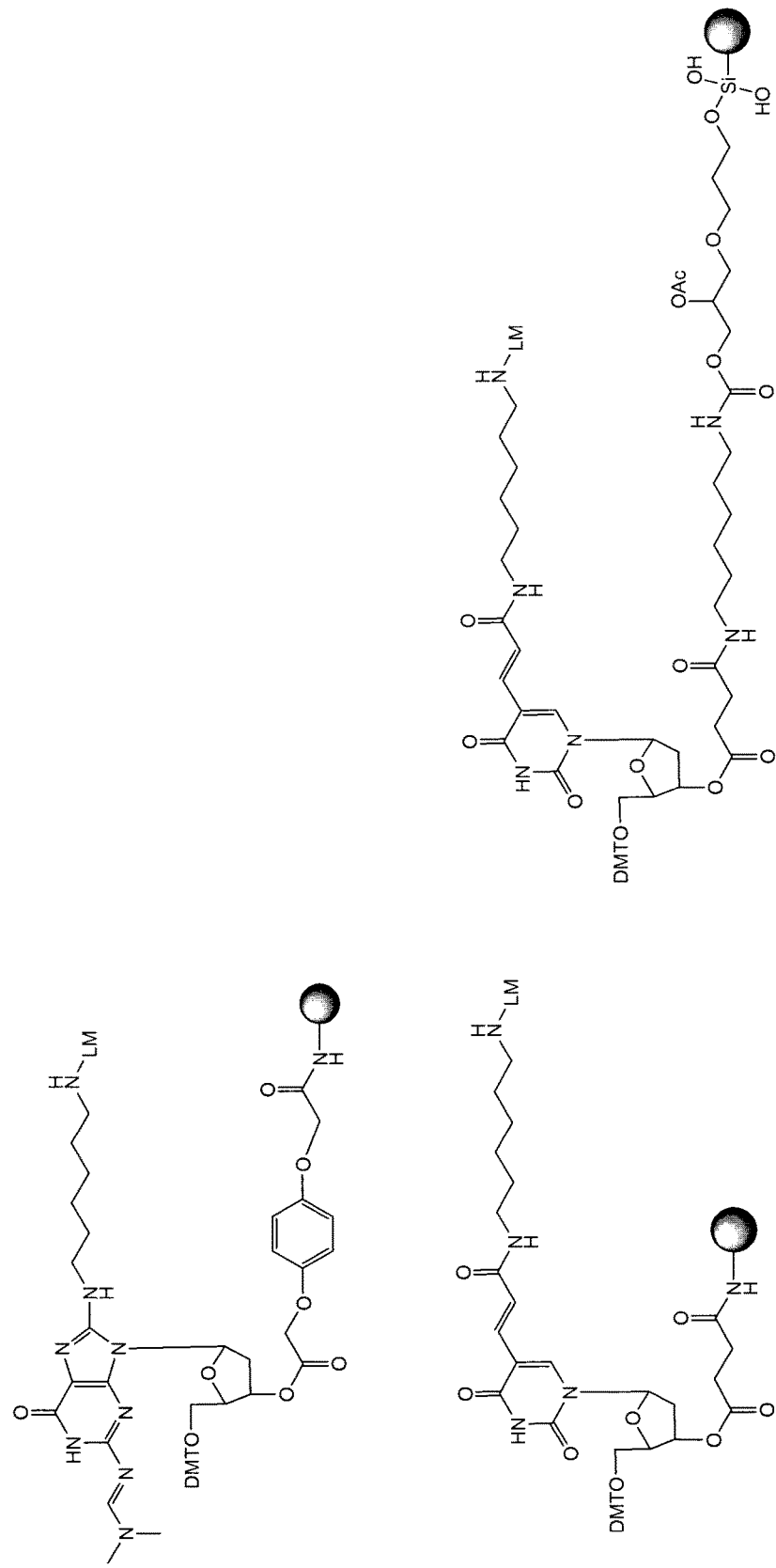

Myriad selectively cleavable linkers useful in the context of oligonucleotide synthesis are known in the art, as are methods of derivatizing solid supports with such linkers. All of these various linkers can be adapted for use in the solid support reagents described herein. Non limiting examples of solid support reagents comprising exemplary linkers that are cleavable under the basic conditions used to deprotect synthetic oligonucleotides are illustrated in FIG. 7.

Like the synthesis reagents, the solid support reagents can be non-nucleosidic or nucleosidic in nature. Exemplary embodiments of non-nucleosidic solid support reagents include reagents according to structural formula (X):

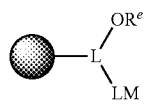

(X)

where LM represents the label moiety, L represents an optional selectively cleavable linker and —OR$^e$ represents the synthesis handle, where R$^e$ is an acid-labile protecting group, as previously described.

In some embodiments, the solid support synthesis reagents of structural formula (X) are non-nucleosidic reagents according to structural formula (X.1):

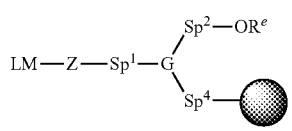

(X.1)

where Z, LM, G, Sp$^1$, Sp$^2$ and R$^e$ are as previously defined in connection with structural formula (IX.1) and Sp$^4$ represents a selectively cleavable spacing moiety. In some specific embodiments, selectively cleavable spacing moiety Sp$^4$ comprises an ester linkage.

In some embodiments, the solid support synthesis reagents of structural formula (X) are nucleosidic reagents according to structural formulae (X.2), (X.3), (X.4) or (X.5):

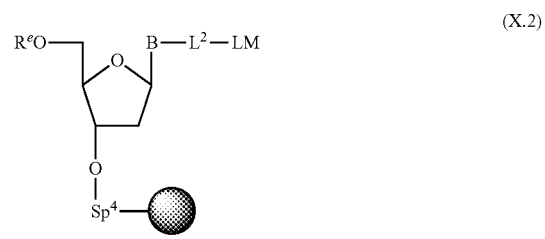

(X.2)

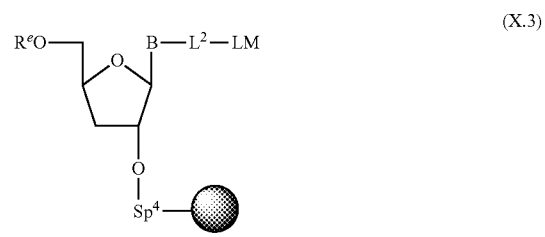

(X.3)

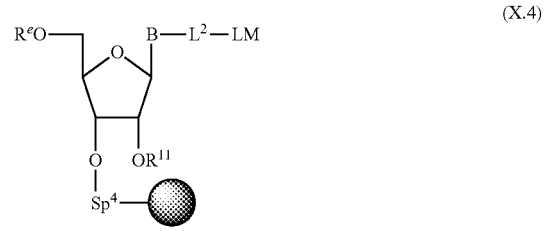

(X.4)

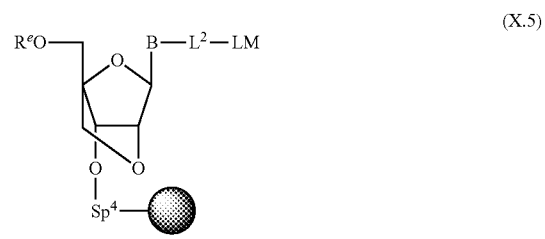

(X.5)

wherein LM, R$^e$, B. L$^2$ are as previously defined for structural formulae (X.2), (X.3), (X.4) and/or (X.5), R$^{11}$ is as previously defined for structural formula (IX.4) and Sp$^4$ represents a selectively cleavable spacing moiety, as described above, which in some embodiments comprises an ester linkage.

5.11 Additional Exemplary Embodiments

It is to be understood that the specific embodiments of the various moieties, groups and linkers described throughout the disclosure can be included in all of the reagents described herein. Moreover, the various specific embodiments can be combined with one another in any combination as though the specific combination had been specifically exemplified. As a specific example, any one of the specific embodiments of label moiety LM described herein can be included in any of the specifically exemplified embodiments of non-nucleosidic and nucleosidic solid support and synthesis reagents described herein. As another specific example, any one of the specific embodiments of phosphate ester precursor group PEP, such as the phosphoramidite group of structural formula (P.1), supra, can be included in any of the synthesis reagents described herein.

5.12 Uses of the Reagents

The various reagents described herein can be used in the step-wise synthesis of oligonucleotides to synthesize oligonucleotides labeled with rhodamine dyes directly on the synthesis resin. Thus, the various reagents make available the ability to synthetically label oligonucleotides with myriad different rhodamines, obviating the need for laborious post-synthesis modifications. The use of an exemplary synthesis reagents to synthesize an oligonucleotide labeled with an NH rhodamine dye is illustrated in FIG. 9.

Figure 10:
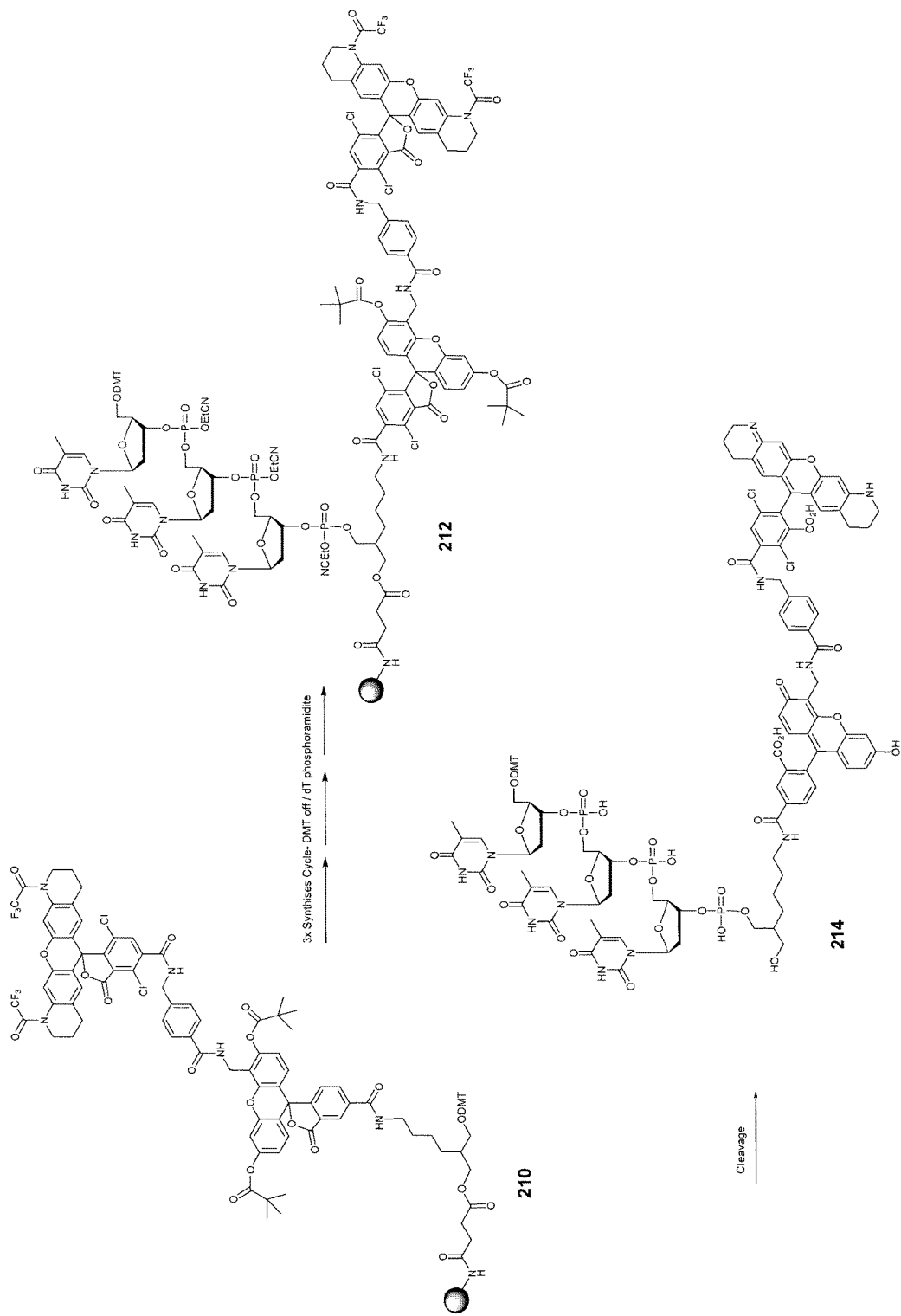
FIG. 10 illustrates the use of a specific embodiment of a synthesis reagent to synthesize an oligonucleotide labeled at its 3-hydroxyl with an energy-transfer dye.

As will be appreciated by skilled artisans, owing to the availability of phosphoramidite reagents that can act as donors, acceptors, or even quenchers for NH-rhodamine dyes, the reagents described herein permit the ability to synthesize oligonucleotides labeled with energy transfer dyes and/or NH-rhodamine-quencher dye pairs, that are synthesized in situ. Exemplary syntheses of oligonucleotides labeled with NH-rhodamine-fluorescein energy transfer dye pairs that illustrate the versatility provided by the reagents described herein are illustrated in FIGS. 10 and 11. Because the reagents described herein permit virtually any NH-rhodamine dye to be included in a solid support and/or synthesis reagent, oligonucleotides labeled with energy transfer dye pairs having spectral properties that are adjusted for specified applications can be conveniently synthesized in situ, without the need for post synthesis modification. Moreover, oligonucleotides labeled with myriad different energy transfer dye pair combinations can be synthesized from individual monomer reagents, obviating the need to make synthesis reagents containing specified dye pairs. Each member of the dye pair can be attached to the nascent oligonucleotide in a step-wise fashion, with or without the addition of intervening linking moieties.

Figure 9:
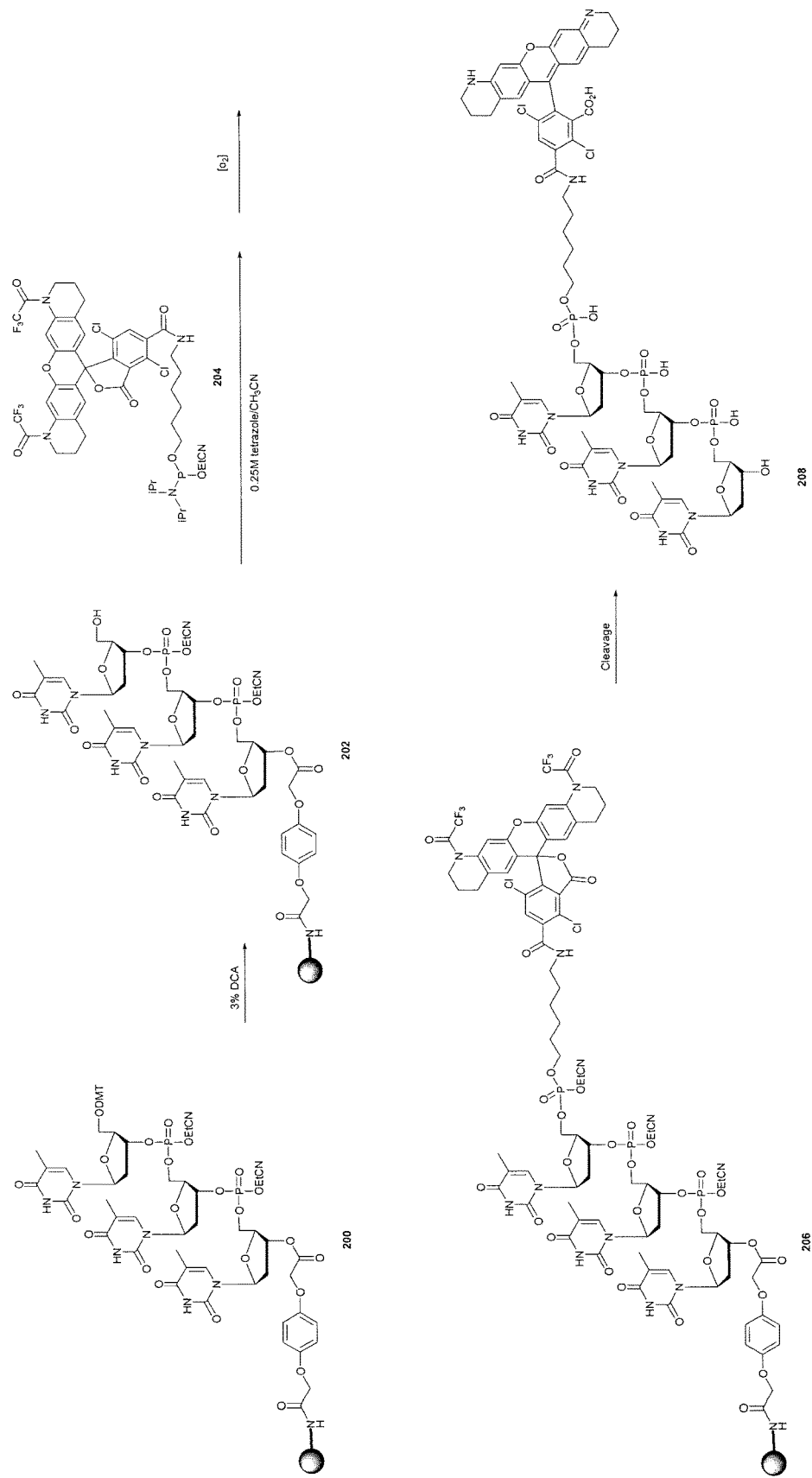
FIG. 9 illustrates the use of a specific embodiment of a synthesis reagent to synthesize an oligonucleotide labeled at its 5'-hydroxyl with an NH-rhodamine dye.

Referring to FIG. 9, support-bound synthetic oligonucleotide 200 is treated with acid to remove the DMT group protecting its 5'-hydroxyl, yielding 5'-deprotected support-bound oligonucleotide 202. Coupling of N-protected NH-rhodamine phosphoramidite reagent 204 followed by oxidation yields support-bound NH-rhodamine-labeled oligonucleotide 206. Treatment with concentrated ammonium hydroxide to remove any protecting groups and cleave the synthesized oligonucleotide from the solid support (resin) yields an oligonucleotide 208 that is labeled with an NH-rhodamine dye.

Referring to FIG. 10, solid support reagent 210, which includes a protected NH-rhodamine-fluorescein energy transfer dye pair as the label moiety, can undergo three cycles of synthesis to yield labeled support-bound oligonucleotide 212. Cleavage from the solid support yields deprotected, labeled oligonucleotide 214.

Figure 11A:
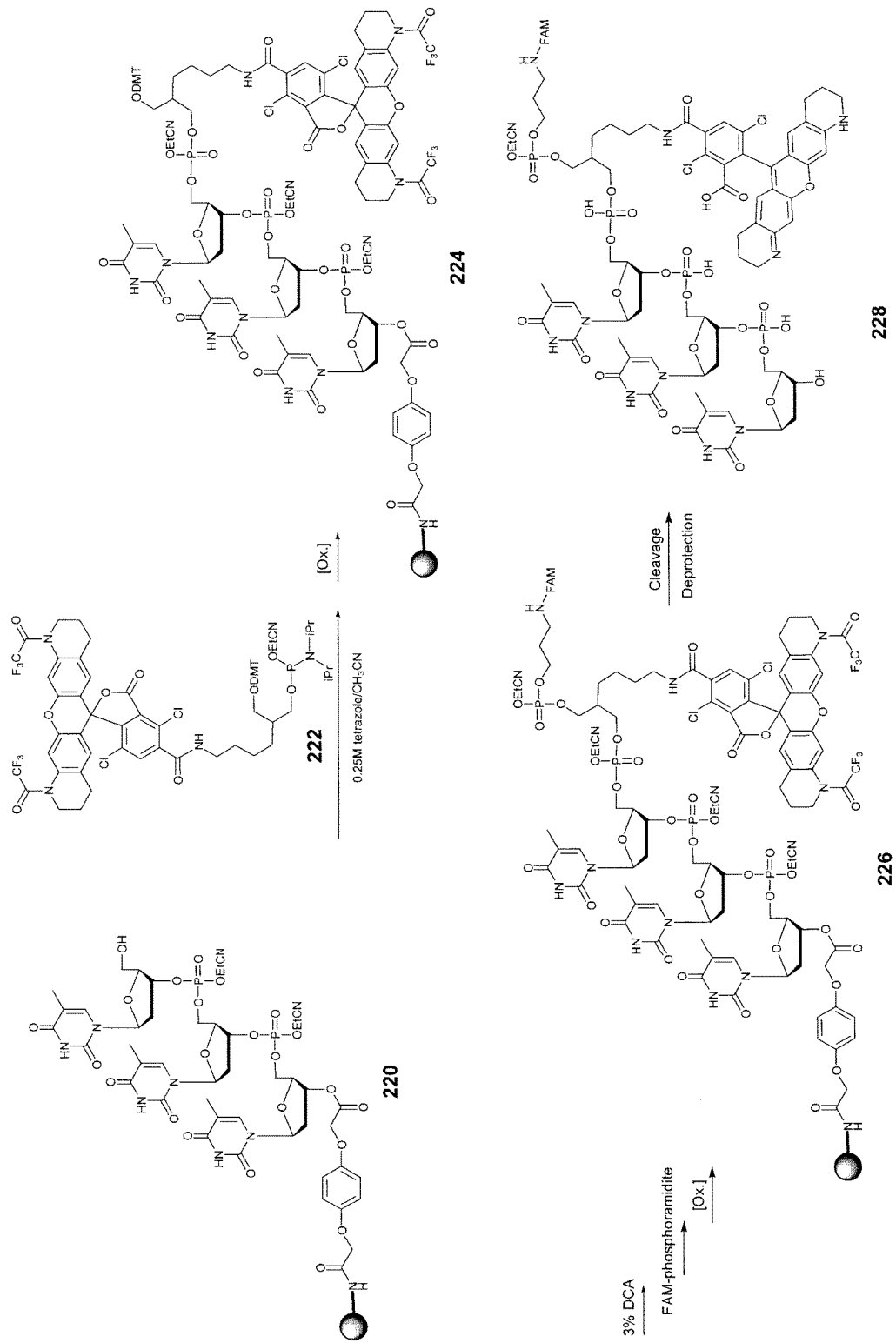
FIG. 11A illustrates the use of a specific embodiment of a synthesis reagent to synthesize in situ an oligonucleotide labeled at its 5'-hydroxyl with an energy-transfer dye.

Referring to FIG. 11A, nascent support-bound oligonucleotide 220 can be labeled with an NH-rhodamine-fluorescein dye pair synthesized in situ by coupling N-protected NH-rhodamine phosphoramidite synthesis reagent 222 to the 5'-hydroxyl of oligonucleotide 220, which, after oxidation, yields NH-rhodamine-labeled oligonucleotide 224. Removal of the DMT group followed by coupling with an O-protected phosphoramidite (which in the specific example illustrated is FAM-phosphoramidite) yields labeled, support-bound oligonucleotide 226. Cleavage and deprotection yields oligonucleotide 228, which is labeled with an NH-rhodamine-FAM energy transfer dye pair.

Figure 11B:
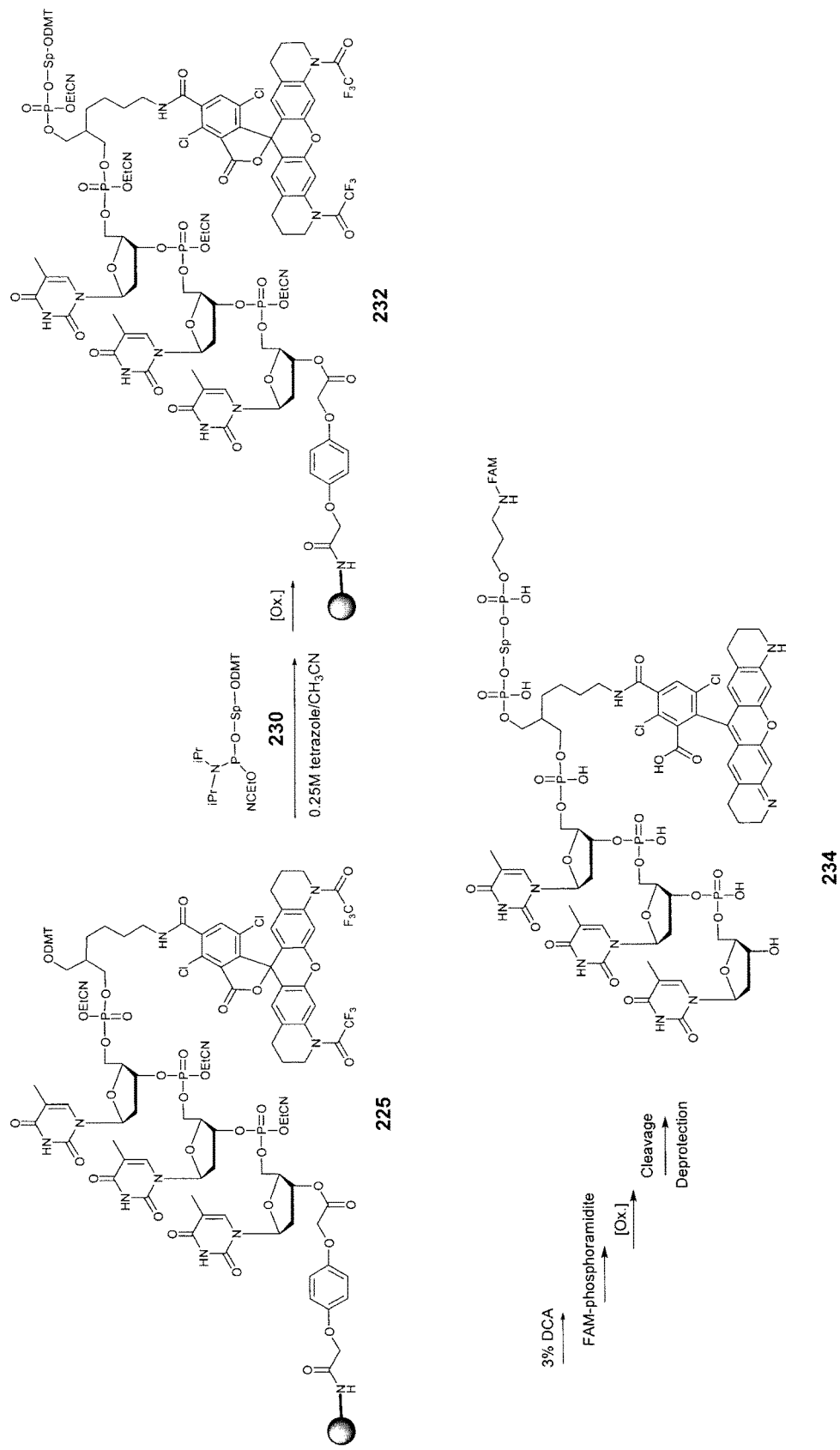
FIG. 11B illustrates the use of a linker phosphoramidite and a specific embodiment of a synthesis reagent to synthesize in situ an oligonucleotide labeled at its 5'-terminus with an energy transfer dye.

The length and character of the linkage linking the donor and acceptor dyes can also be manipulated through the use of phosphoramidite linker reagents. This aspect is illustrated in FIG. 11B, where linker phosphoramidite 230 is coupled to rhodamine-labeled oligonucleotide 225, yielding reagent 232. Coupling with FAM-phosphoramidite followed by oxidation, deprotection and cleavage yields oligonucleotide 234, which is labeled with an NH-rhodamine-FAM energy transfer dye pair. In linker phosphoramidite 230, "Sp" is a spacer, as previously defined. For example, "Sp" could represent (Sp.1), (Sp.2), (Sp.3), (Sp.4) or (Sp.5), as previously defined.

In the scheme illustrated in FIG. 11B, the length and properties of the linker linking the NH-rhodamine and FAM dyes can be adjusted by coupling additional linker phosphoramidites to reagent 232 prior to coupling with the FAM-phosphoramidite. The linker phosphoramites could be the same, or they could be different. In this way, oligonucleotides labeled with energy transfer dye pairs in which the donor and acceptor dyes, as well as the linker linking the donor and acceptors, are tailored for specific purposes can be readily synthesized in situ.

While FIGS. 11A & B exemplify the use of a specific N-protected NH-rhodamine reagent, skilled artisan will appreciate that any N-protected NH-rhodamine reagent that acts as an acceptor for FAM could be used. Moreover, other O-protected fluoresceins could be used, as could other types of phosphoramidite dyes. Since the dyes are added as monomers, the number of energy transfer dye labels available is greater than the number of phosphoramidite reagents necessary to synthesize them. For example, oligonucleotides labeled with 9 different energy-transfer dye pairs can be synthesized from 3 different N-protected NH-rhodamine phosphoramidite reagents (reagents A, B and C) and 3 different O-protected fluorescein phosphoramidite reagents (reagents 1, 2 and 3): oligo-A1, oligo-A2, oligo-A3, oligo-B1, oligo-B2, oligo-B3, oligo-C1, oligo-C2 and oligo-C3.

6. EXAMPLES

Example 1: Synthesis of N-Protected NH-Rhodamine Phosphoramidite Synthesis Reagents Parent NH-rhodamine dyes including a carboxyl substitutent at the C5- or C6-position were synthesized as described in U.S. Pat. No. 4,622,400, U.S. Pat. No. 5,750,409, U.S. Pat. No. 5,847,162, U.S. Pat. No. 6,017,712, U.S. Pat. No. 6,080,852, U.S. Pat. No. 6,184,379 or U.S. Pat. No. 6,248,884. The parent NH-rhodamine dyes were then protected at the exocyclic amines with either acetyl or trifluoroacetyl protecting groups, the resultant N-protected NH-rhodamine dyes were converted to hydroxyl-amide derivatives via the corresponding NHS ester derivative and the hydroxyl functionality converted to a phosphoramidite using standard procedures. The overall scheme is illustrated below:

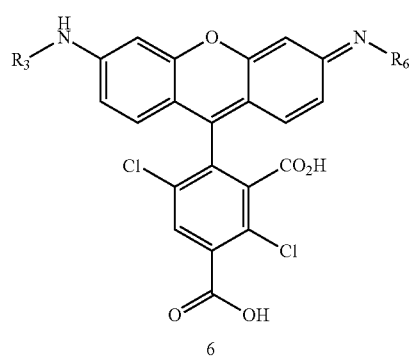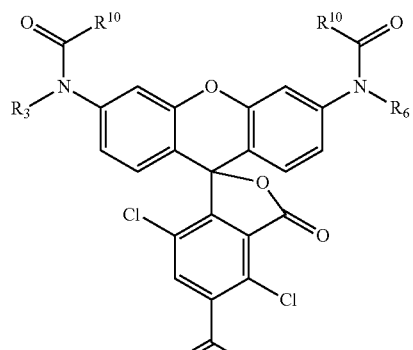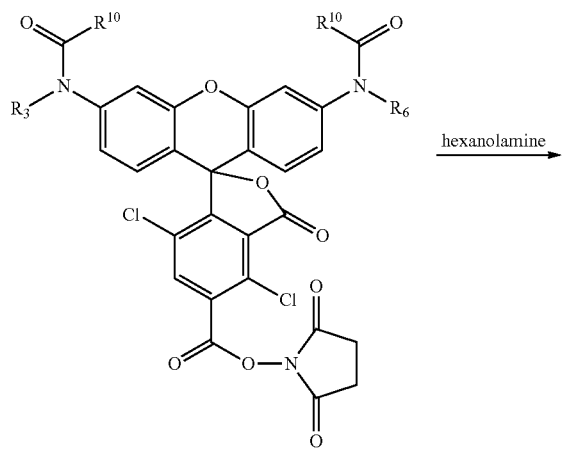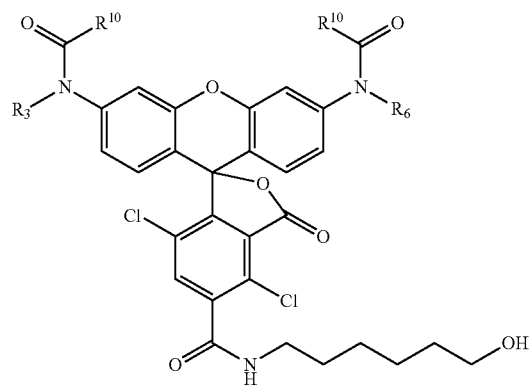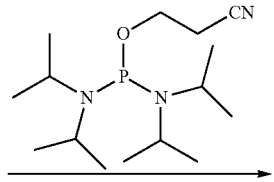

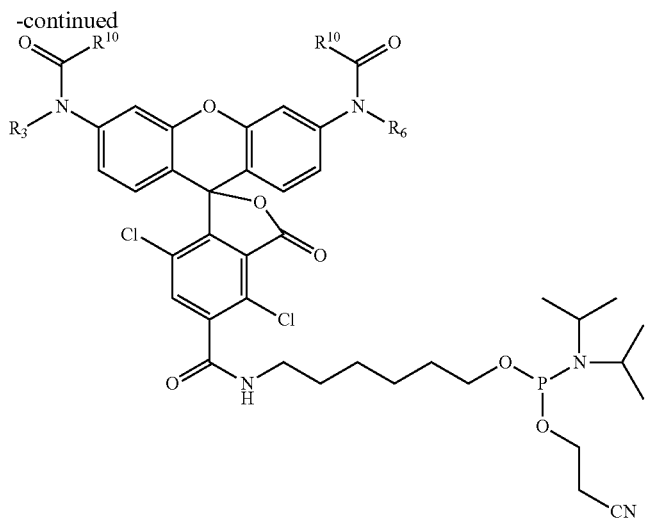

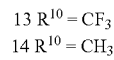

Protection with Acetyl Groups.

NH-rhodamine dye acid 6 (mono TEA salt, 1.676 mmol) was suspended in DCM (40 mL) and TEA (3.67 mL). Acetic anhydride (3.13 mL) was added, and the reaction mixture was stirred at room temperature for 3 days. $H_2O$ (10 mL) was added and stirring was continued for 30 min. The mixture was diluted with DCM (200 mL), washed with $NaHCO_3$ solution (200 mL×2), dried ($Na_2SO_4$), filtered, and evaporated. The residue was purified by flush chromatography on silica (using a gradient of MeOH/EtOAc/DCM as eluent, from 5:20:75 to 20:20:60). Evaporation of the appropriate fractions gave 881 mg (87%) of colorless lactonized bis acetyl N-protected NH-rhodamine dye 8.

Protection with Trifluoroacetyl Groups.

NH-rhodamine dye acid 6 (mono TEA salt, 1.5 g, 2.402 mmol) was suspended in DCM (30 mL) and TEA (6.696 mL). The suspension was cooled to 0° C. and trifluoroacetic anhydride (2.0 mL) added drop wise through a syringe. After the addition was complete, the reaction mixture was stirred at room temperature for 10 min (and sonicated to break up dye particles). The resultant brownish solution was evaporated, re-dissolved in DCM (50 mL), and stirred with 5% HCl (40 mL) at room temperature for 1 h. The reaction mixture was transferred to a separatory funnel and the two layers separated. The DCM layer was washed with a Brine solution (40 mL), dried ($Na_2SO_4$), filtered, and evaporated. The residue was co-evaporated with MeCN (2 x) to give 1.79 g of crude N-protected NH-rhodamine dye 7.

Synthesis of N-Protected NH-Rhodamine NHS Esters.

To a solution of bis-acetyl dye 8 (588 mg, 0.968 mmol) and NHS (334 mg, 2.904 mmol) in DCM (20 mL), was added DCC (599 mg, 2.904 mmol). The reaction mixture was stirred at room temperature for 2 h, and then the reaction mixture was filtered. The filtrate was diluted with DCM (80 mL), washed with $H_2O$ (50 mL×2), dried ($Na_2SO_4$), filtered, and evaporated. The residue was purified by flash chromatography on silica (using a gradient of AcOH/MeOH/EtOAc/DCM as eluent, from 1:1:20:78 to 1:5:20:74).

Evaporation of the appropriate fractions gave 680 mg (100%) of bis acetyl N-protected NH-rhodamine NHS ester 10.

Following the procedure described above for bis acetyl N-protected NH-rhodamine NHS ester 10, bis-TFA N-protected NH-rhodamine Dye 7 (0.322 mmol), gave bis-TFA N-protected NH-rhodamine NHS ester 9 in 80-90% yield.

Synthesis of N-Protected NH-Rhodamine Phosphoramidites.

NHS ester 9 (0.4 mmol) was dissolved in DCM (8 mL). To this stirred solution, a mixture of 6-amino-1-hexanol/DIPEA/DCM (56 mg/0.07 mL/2 mL) was added. The reaction was stirred at room temperature for 30 min. The solid byproduct was removed by filtration and the filtrate was purified by flush chromatography on silica (using a gradient of EtOAc/DCM as eluent, from 30% to 60%). Evaporation of the appropriate fractions gave 0.344 mmol (86%) of bis-TFA-hexanolamide rhodamine dye 11.

NHS ester 10 was converted to the bis-acetyl-hexanolamide NH-rhodamine dye 12 using a similar procedure.

To a solution of bis-TFA-hexanolamide rhodamine dye 11 (0.338 mmol) and 2-Cyanoethyl N,N,N',N'-tetraisopropylphosphorodiamidite (0.214 mL, 0.674 mmol, 2 equiv.) in DCM (10 mL), was added tetrazole amine (4 mg) in one portion. The reaction mixture was stirred at room temperature for 20 h Volatile materials were removed by evaporation and the residue was purified by precipitation three times from DCM/hexane. The solid product was dried in vacuo to give 0.256 mmol (76%) bis-TFA-N-protected NH-rhodamine dye phosphoramidite 13.

Similarly, bis-acetyl dye 12 was converted to phosphoramidite 14.

Example 2: Synthesis of Heterodimeric Dye Networks

A dye network comprising an O-protected fluorescein linked to an N-protected NH-rhodamine was synthesized as illustrated below:

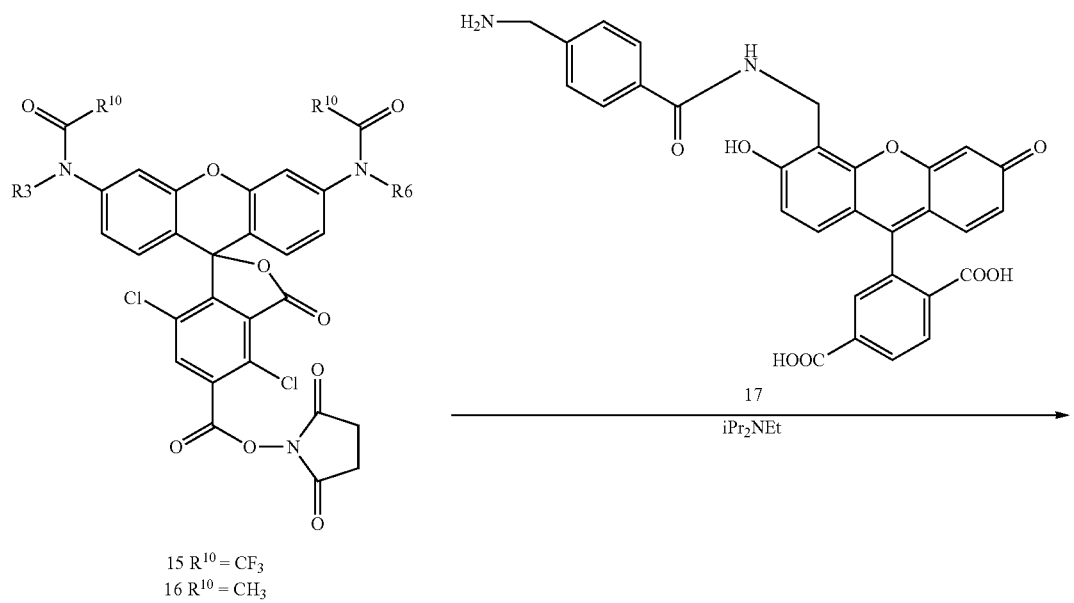

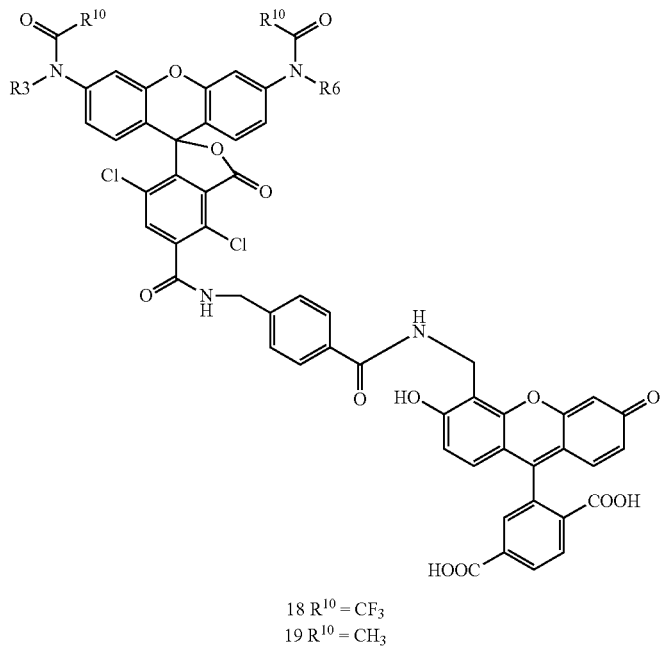

18 R¹⁰ = CF₃
19 R¹⁰ = CH₃

Bis-acetyl N-protected NH-rhodamine NHS ester 16 (324 mg, 0.460 mmol) was dissolved in a solution of DMF (8 mL) and DIPEA (0.3 mL). Fluoresecin derivative 17 (239 mg, 0.32 mmol; synthesized as described in U.S. Pat. No. 5,800,996) was added and the reaction mixture stirred at room temperature for 1 h. The mixture was evaporated and then co-evaporated with MeOH (2×). The residue was dissolved in 10% MeOH/DCM (100 mL) and washed with Brine solution (100 mL). The aqueous layer was extracted with 10% MeOH/DCM (50 mL×3), and the combined organic layer was dried ($Na_2SO_4$), filtered, and evaporated. The residue was purified by flush chromatography on silica (using a gradient of MeOH/DCM as eluent, from 10% to 30%). Evaporation of the appropriate fractions gave 270 mg (63%) of heterodimeric dye network 19 (as the DIPEA salt).

The corresponding bis-TFA protected dye network 18 was synthesized by a similar procedure.

Example 3: Synthesis of Heterodimeric Dye Network Phosphoramidite

A phosphoramidite synthesis reagent comprising the heterodimeric dye network as the label moiety was synthesized as illustrated below:

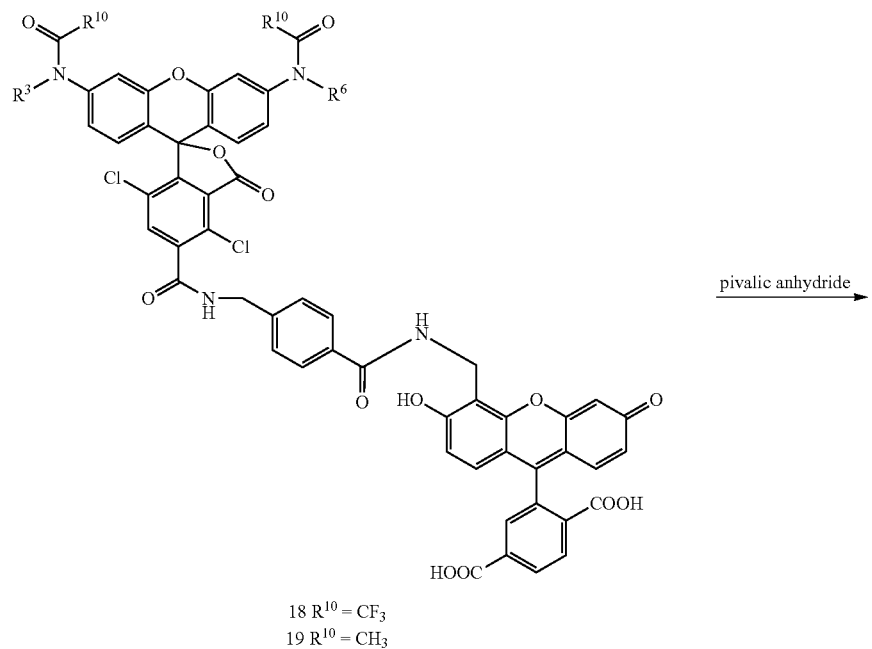
18 R¹⁰ = CF₃
19 R¹⁰ = CH₃
pivalic anhydride
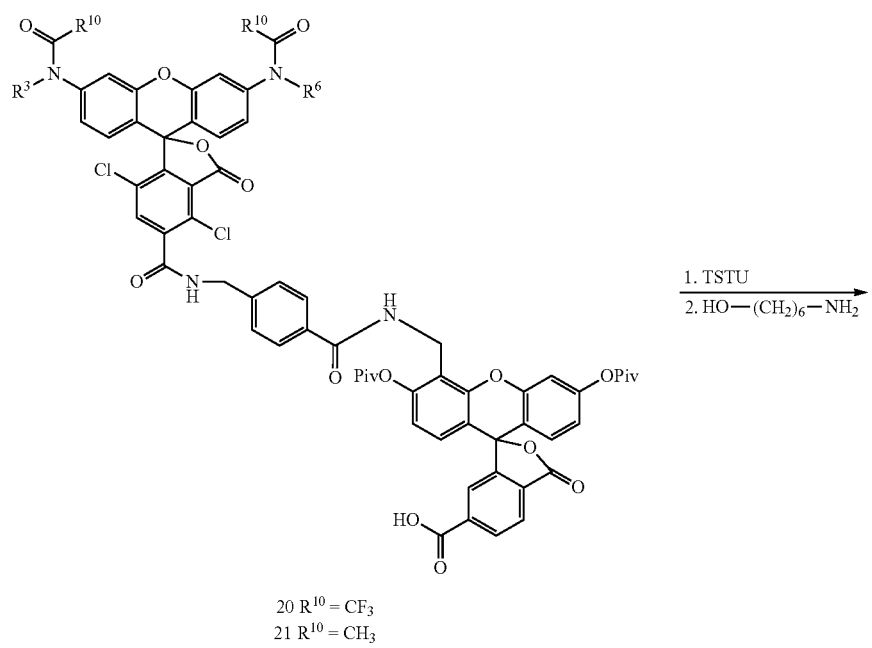
20 R¹⁰ = CF₃
21 R¹⁰ = CH₃
1. TSTU
2. HO—(CH₂)₆—NH₂

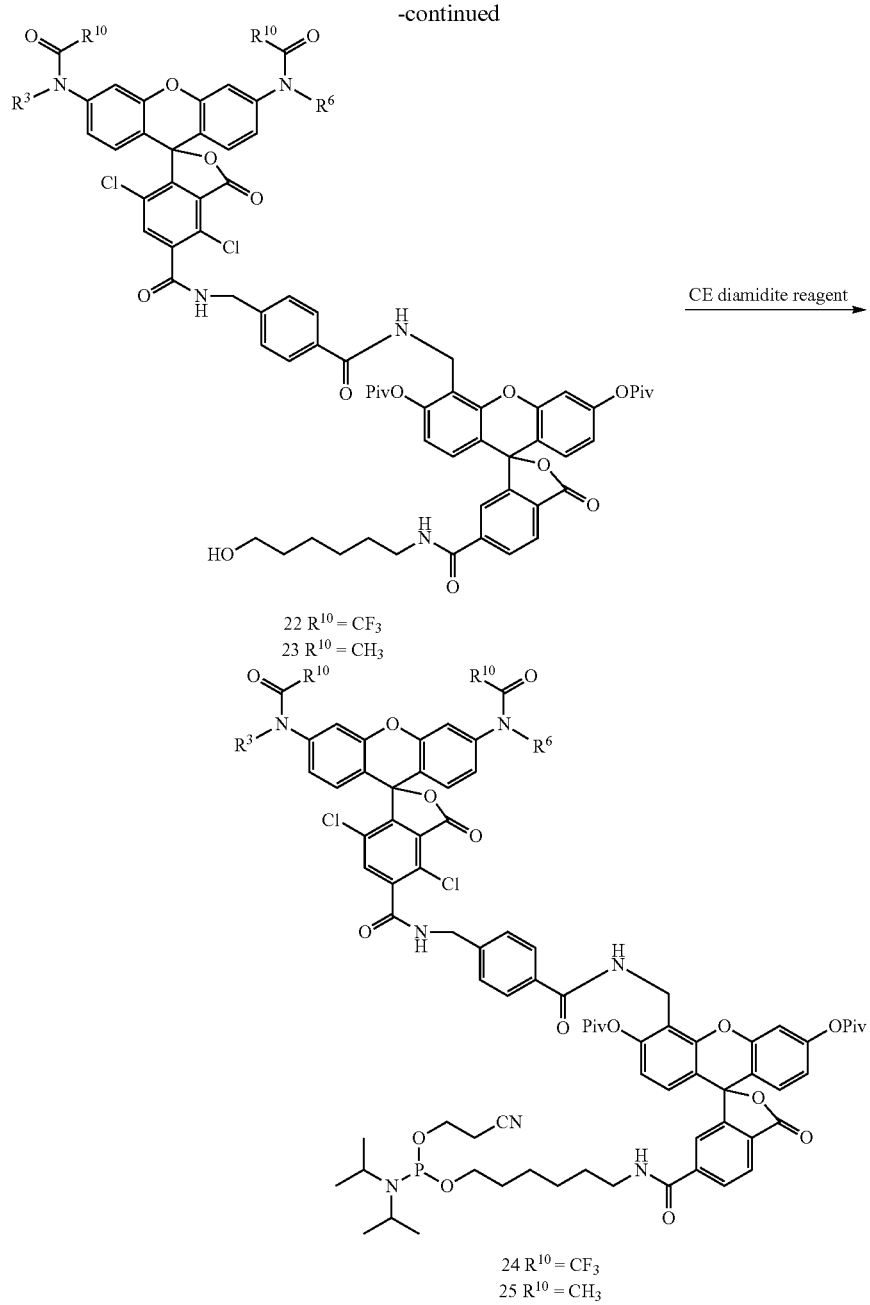

22 R[10] = CF₃
23 R[10] = CH₃

24 R[10] = CF₃
25 R[10] = CH₃

A solution of heterodimeric dye network 19 (0.173 mmol), DIPEA (1.028 mL) and pivalic anhydride (0.702 mL) in DCM (10 mL) was stirred at room temperature for 1 day. H$_2$O (5 mL) was added and stirring was continued for 1 h. The reaction mixture was diluted with DCM (50 mL) and washed with H$_2$O (40 mL). The aqueous layer was extracted with DCM (40 mL). The combined organic layer was dried (Na$_2$SO$_4$), filtered, and evaporated. The residue was purified by flush chromatography on silica (using a gradient of MeOH/DCM as eluent, from 3% to 15%). Evaporation of the appropriate fractions gave 0.145 mmol (84%) of bis-acetyl bis-pivaloyl heterodimeric dye derivative 21 (as the DIPEA salt).

Dye derivative 21 (0.146 mmol) was suspended in a dissolved of DIPEA (0.2 mL) and DCM (8 mL). Solid N-hydroxysuccinimide tetramethyluronium tetrafluoroborate (88 mg) was added and the reaction stirred at room temperature for 1 h. 6-Amino-1-hexanol (51 mg) was added and stirring was continued for 1 h. The reaction mixture was filtered and the filtrate was diluted with DCM (50 mL). The DCM solution was washed with brine solution (40 mL), dried (Na$_2$SO$_4$), filtered, and evaporated. The residue was purified by flush chromatography on silica gel (using a gradient of MeOH:EtOAc:DCM as eluent, from 5:20:75 to 15:20:65). Evaporation of the appropriate fractions gave 0.124 mmol (85%) of Dye hexanolamide derivative 23 (as the DIPEA salt).

Dye derivative 23 (91 mg, 0.057 mmol) and tetrazole amine (2 mg) were dissolved in DCM (5 mL). 2-cyanoethyl-N,N,N',N'-tetraisopropylphosphoramidite (CE diamidite)

(0.04 mL), and was added and the reaction stirred at room temperature for 16 h. The reaction mixture was diluted with a solution of TEA:EtOAc:DCM (3:20:77, 3 mL) and purified by silica gel chromatography (using a gradient of TEA:MeOH:EtOAc:DCM as eluent, from 3:0:20:77 to 3:5:20:72). Evaporation of the appropriate fractions and precipitation from DCM/hexane gave 75 mg (74%) of heterodimeric dye phosphoramidite 25.

Example 4: Synthesis of a Non-Nucleosidic Phosphoramidite Synthesis Reagent Including an Optional Synthesis Handle A non-nucleosidic phosphoramidite synthesis reagent that includes an optional synthesis handle of the formula —$OR^e$ was synthesized as illustrated below:

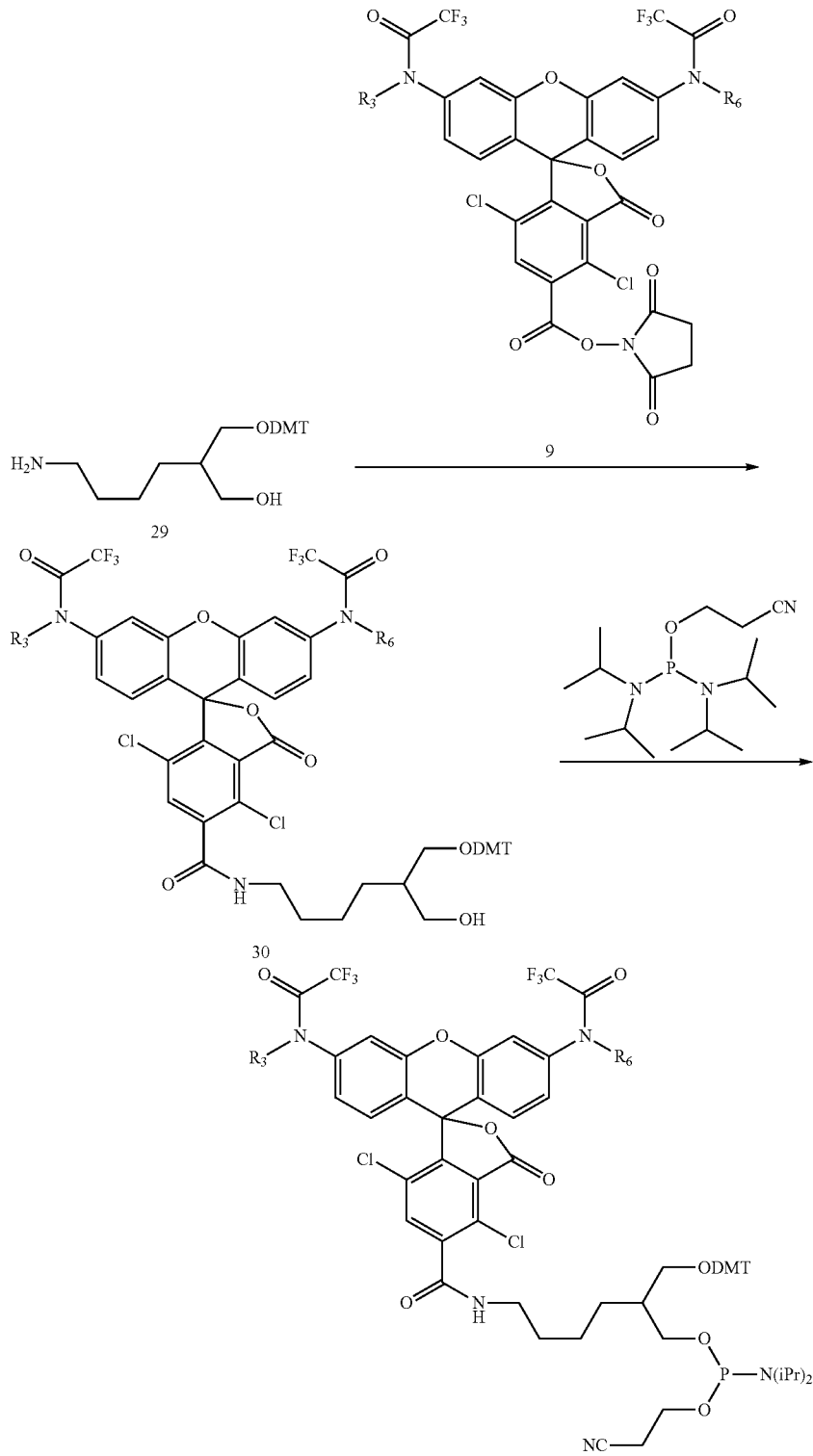

Bis-TFA derivative 9 (1.354 mmol) was dissolved in a solution of DIPEA (0.236 mL) in DCM (30 mL). To the stirred solution, linker synthon 29 and DCM (0.609 g, 1.355 mmol; synthesized as described in Nelson et al., 1992, Nucl. Acids Res. 20:6253-6259) was added stirring continued at room temperature for 2 h. EtOAc was added and the mixture was loaded on a silica column. Pure product was isolated by elution using a gradient of EtOAc:DCM from 5:95 to 1:5. Evaporation of the appropriate fractions gave 1.25 g (80%) of bis-TFA-rhodamine-hydroxy amide 30.

A solution of bis-TFA-rhodamine-hydroxy amide 30 (1.081 mmol) and tetrazole amine (18.5 mg) were dissolved in DCM (35 mL). CE diamidite was added (0.685 mL) and the reaction stirred at room temperature for 18 h. The solvent was removed under reduced pressure and the residue precipitated from DCM/hexane (3 x) to give 1.081 mmol (100%) of pure bis-TFA-rhodamine DMT phosphoramidite 31.

Example 5: Solid Phase Synthesis of a Labeled Oligonucleotide

Oligonucleotides labeled with the N-protected NH-rhodamine phosphoramidite synthesis reagents were synthesized on polystyrene solid supports using the standard operating conditions on an AB 3900 automated DNA synthesizer. The N-protected NH-rhodamine phosphoramidites were soluble in the acetonitrile solvent for the coupling reactions, and the N-protected Nh-rhodamine dye adducts were stable to repeated synthesis cycles which employed removal of DMT with dichloroacetic acid, addition of nucleoside phosphoramidite monomers, capping with acetic anhydride and oxidation with iodine to generate the internucleotide phosphate linkages. This class of NH-rhodamine was also found to be stable to the conditions used to deprotect and cleave the synthesized labeled oligonucleotide from the solid support (treatment with ammonium hydroxide at 60° C. for 1-2 h). The overall scheme used to synthesize the labeled oligonucleotide is illustrated below:

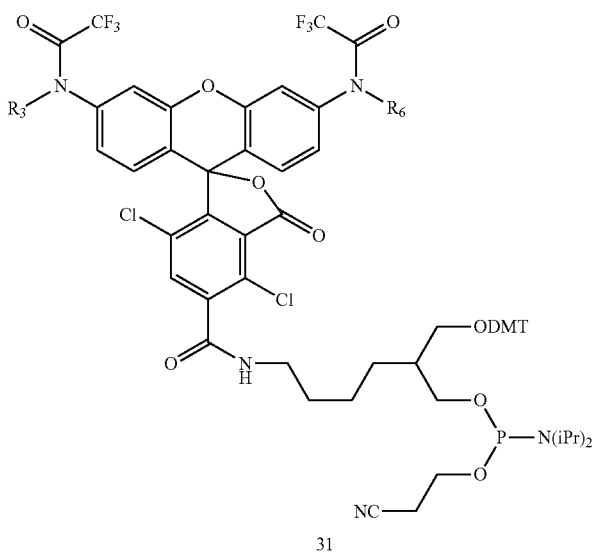

31

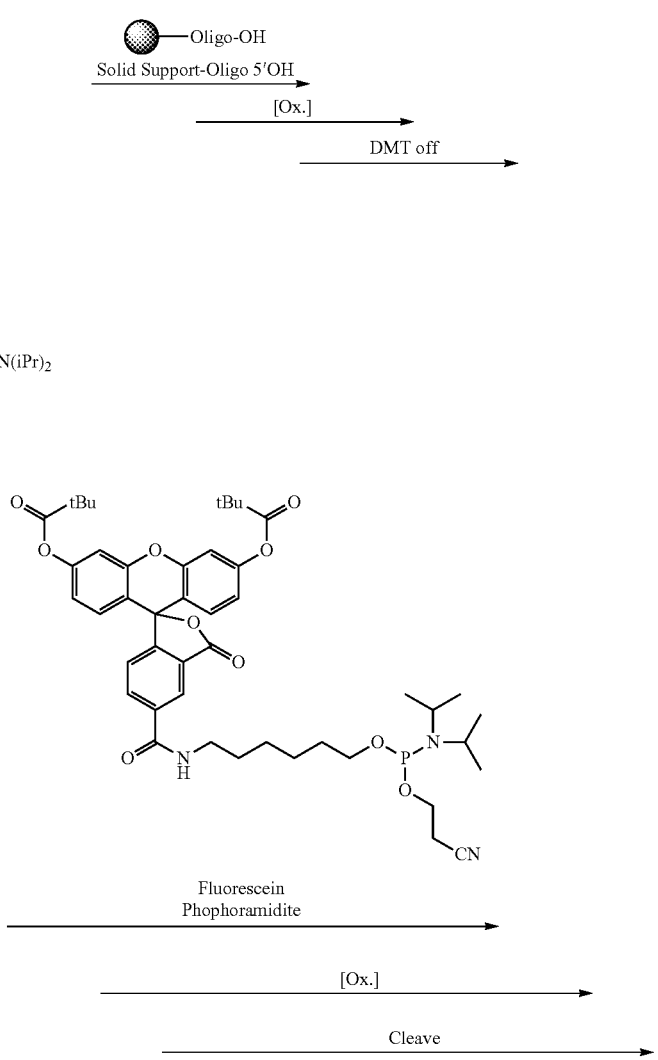

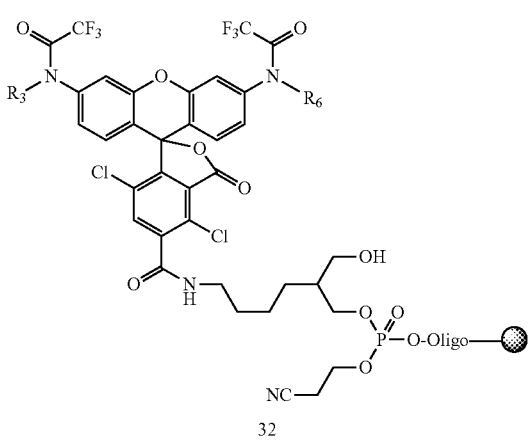

32

-continued

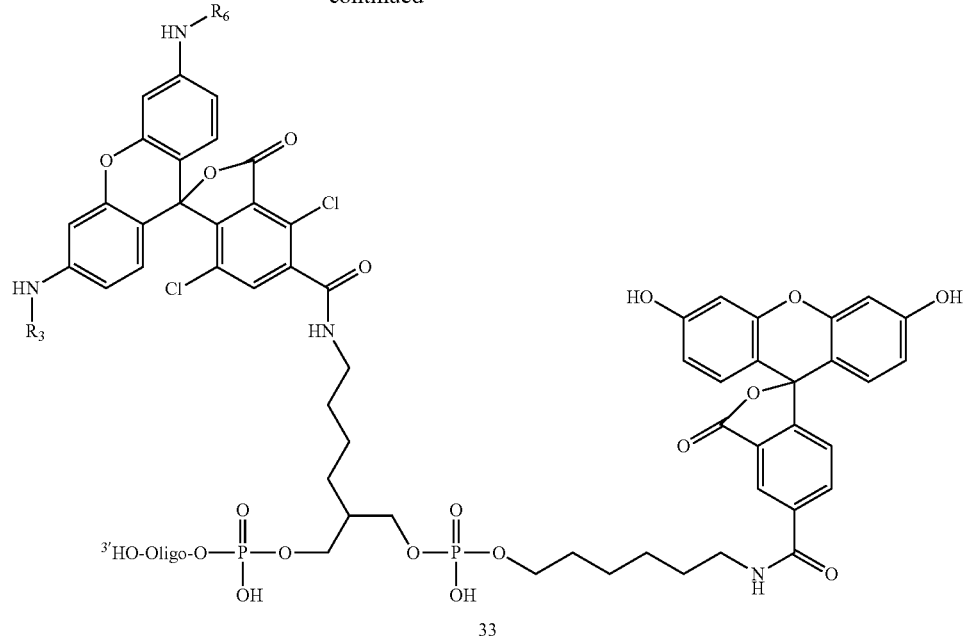

33

By this process, TFA-rhodamine DMT phosphoramidite 31 was coupled to the 5'-hydroxyl of a support-bound oligonucleotide to give the phosphite intermediate 32. Fluorescein phosphoramidite (Glenn Research) was coupled to the free hydroxyl of intermediate 32. The resultant labeled oligo was oxidized, cleaved from the support with concentrated ammonia hydroxide for 1 to 2 hours at 60° C., washed with acetonitrile/water and dried under reduced pressure to yield labeled oligonucleotide 33. Oligo 33 was re-precipitated using a standard sodium acetate/EtOH precipitation protocol. Labeled oligo 33 was produced in greater then 90% purity and in greater than 85% yield (170,000 pM from 0.2 uM support) and used without further purification.

Example 6: Labeled Oligonucleotides Synthesized with the Synthesis Reagents Exhibit Good Spectral Properties Poly(dT)$_{10}$ oligonucleotides labeled with NH-rhodamines or NH-rhodamine-fluorescein dye pairs were synthesized as illustrated above. Following cleavage, fluorescence spectra were recorded. All labeled oligos synthesized exhibited good fluorescence properties.

Although the foregoing inventions have been described in some detail to facilitate understanding, it will be apparent that certain changes and modifications may be practiced within the scope of the appended claims. Accordingly, the described embodiments are to be considered as illustrative and not restrictive, and the various inventions described herein are not to be limited to the details provided herein.

All literature and patent references cited throughout the disclosure are incorporated into the application by reference for all purposes.

What is claimed is:

1. A reagent useful for labeling an oligonucleotide, which is a compound according to structural formula (VII):

LM-L-PEP      (VII)

wherein LM represents a label moiety that comprises an N-protected NH-rhodamine moiety, PEP represents a phosphate ester precursor group which comprises a phosphoramidite group or an H-phosphonate group, and L represents an optional linker linking the label moiety to the phosphate ester precursor group, and further wherein the in which the N-protected NH-rhodamine moiety comprises a structure selected from structural formulae (IIIc), (IIIb) and (IIIc):

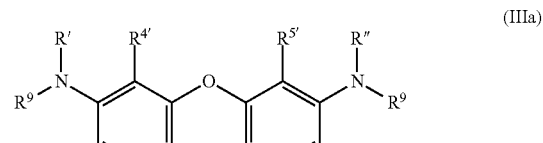

(IIIa)

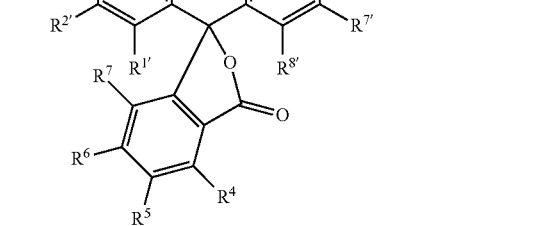

(IIIb)

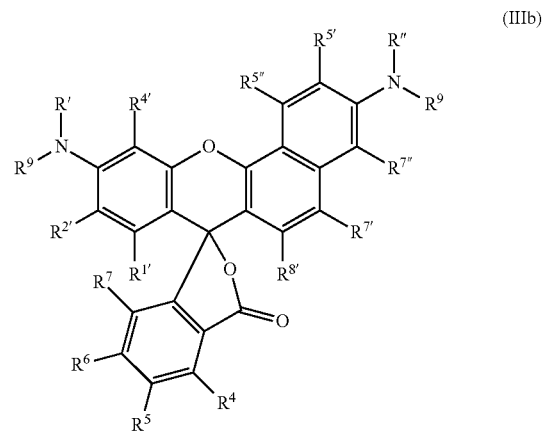

-continued

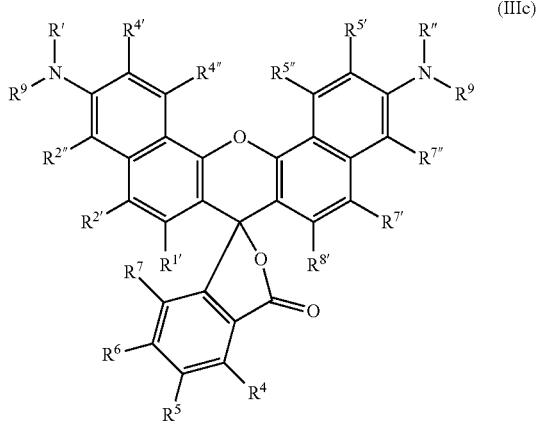

(IIIc)

wherein:
R' is selected from $R^{3'}$ and hydrogen;
R" is selected from $R^{6'}$ and hydrogen;
$R^9$ is a protecting group having a structure of the formula —C(O)$R^{10}$, wherein $R^{10}$ is selected from hydrogen, a lower alkyl, —$CX_3$, —$CHX_2$, —$CH_2X$, —$CH_2$—$OR^d$, and phenyl optionally monosubstituted with a lower alkyl, —X, —$OR^d$, cyano or nitro group, wherein $R^d$ is selected from a lower alkyl, phenyl and pyridyl, and each X is a halo group;
each of $R^{1'}$, $R^{2'}$, $R^{2''}$, $R^{4'}$, $R^{4''}$, $R^{5'}$, $R^{5''}$, $R^{7'}$, $R^{7''}$, $R^{8'}$, $R^4$, $R^5$, $R^6$, and $R^7$, when taken alone, are each, independently of one another, selected from hydrogen, lower alkyl, (C6-C14) aryl, (C7-C20) arylalkyl, 5-14 membered heteroaryl, 6-20 membered heteroarylalkyl, —$R^b$ and —$(CH_2)_x$—$R^b$, where x is an integer ranging from 1 to 10 and $R^b$ is selected from —X, —OH, —$OR^a$, —SH, —$SR^a$, —$NH_2$, —$NHR^a$, —$NR^cR^c$, —$N^+R^cR^cR^c$, perhalo lower alkyl, trihalomethyl, trifluoromethyl, —$B(OH)_3$, —$B(OR^a)_3$, —$B(OH)O^-$, —$B(OR^a)_2O^-$, —$B(OH)(O^-)_2$, —$B(OR^a)(O^-)_2$, —$P(OH)_2$, —$P(OH)O^-$, —$P(OR^a)_2$, —$P(OR^a)O^-$, —$P(O)(OH)_2$, —$P(O)(OH)O^-$, —$P(O)(O^-)_2$, —$P(O)(OR^a)_2$, —$P(O)(OR^a)O^-$, —$P(O)(OH)(OR^a)$, —$OP(OH)_2$, —$OP(OH)O^-$, —$OP(OR^a)_2$, —$OP(OR^a)O^-$, —$OP(O)(OH)_2$, —$OP(O)(OH)O^-$, —$OP(O)(O^-)_2$, —$OP(O)(OR^a)_2$, —$OP(O)(OR^a)O^-$, —$OP(O)(OR^a)(OH)$, —$S(O)_2O^-$, —$S(O)_2OH$, —$S(O)_2R^a$, —C(O)H, —C(O)$R^a$, —C(S)X, —C(O)$O^-$, —C(O)OH, —$C(O)NH_2$, —C(O)$NHR^a$, —C(O)$NR^cR^c$, —$C(S)NH_2$, —C(O)$NHR^a$, —C(O)$NR^cR^c$, —$C(NH)NH_2$, —C(NH)$NHR^a$, and —C(NH)$NR^cR^c$, where X is halo, each $R^a$ is, independently of the others, selected from lower alkyl, (C6-C14) aryl, (C7-C20) arylalkyl, 5-14 membered heteroaryl and 6-20 membered heteroarylalkyl, and each $R^c$ is, independently of the others, an $R^a$, or, alternatively, two $R^c$ bonded to the same nitrogen atom may be taken together with that nitrogen atom to form a 5- to 8-membered saturated or unsaturated ring that may optionally include one or more of the same or different ring heteroatoms, which are typically selected from O, N and S, or, alternatively, $R^{1'}$ and $R^{2'}$ or $R^{7'}$ and $R^{8'}$ are taken together with the carbon atoms to which they are bonded to form an optionally substituted (C6-C14) aryl bridge and/or $R^{4'}$ and $R^{4''}$ and/or $R^{5'}$ and $R^{5''}$ are taken together with the carbon atoms to which they are bonded to form a benzo group; and
each of $R^{3'}$ and $R^{6'}$, when taken alone, are each, independently of one another, selected from lower alkyl, (C6-C14) aryl, (C7-C20) arylalkyl, 5-14 membered heteroaryl and 6-20 membered heteroarylalkyl, or alternatively, $R^{3'}$ and $R^{2'}$ or $R^{4'}$ and/or $R^{6'}$ and $R^{5'}$ or $R^{7'}$ in the compounds of structural formula (IIIa), $R^{3'}$ and $R^{2'}$ or $R^{4'}$ and/or $R^{6'}$ and $R^{5'}$ or $R^{7''}$ in the compounds of structural formula (III6), or $R^{3'}$ and $R^{2''}$ or $R^{4'}$ and/or $R^{6'}$ and $R^{5'}$ or $R^{7''}$ in the compounds of structural formula (IIIc) are taken together with the atoms to which they are bonded to form a 5- or 6-membered saturated or unsaturated ring which is optionally substituted with one or more of the same or different lower alkyl, benzo or pyrido groups,
with the proviso that at least one of $R^{2'}$, $R^{4'}$, $R^{5'}$, $R^{7'}$, $R^5$ or $R^6$ in the compounds structural formula (IIIa), at least one of $R^{2'}$, $R^{4'}$, $R^{5'}$, $R^{7''}$, $R^5$ or $R^6$ in the compounds of structural formula (IIIb) and at least one of $R^{2''}$, $R^{4'}$, $R^{5'}$, $R^{7''}$, $R^5$ or $R^6$ in the compounds of structural formula (IIIc) comprises a group of the formula —Y—, where Y is chosen from —C(O)—, —$S(O)_2$—, —S—, and —NH.

2. The reagent of claim 1 in which L is selected from —Z—$(CH_2)_{3-6}$—O$^-$, —Z—$(CH_2)_a$—[(Ar)$_b$—$(CH_2)_a$]$_c$—O—, —Z—$(CH_2)_a$—[C≡C—$(CH_2)_a$]$_c$—O—, —Z—$(CH_2)_a$—[C≡C—(Ar)$_b$]$_c$—$(CH_2)_a$—O—, —Z—$(CH_2)_d$—NH—C(O)—[$(CH_2)_a$—(Ar)—$(CH_2)_a$—C(O)—NH]$_c$—$(CH_2)_d$—O—, and —Z—[$CH_2(CH_2)_eO$]$_f$—$CH_2(CH_2)_eO$—, wherein:
each Z represents, independently of the others, a portion of a linkage contributed by a functional group $F^z$;
each a represents, independently of the others, an integer ranging from 0 to 4;
each b represents, independently of the others, an integer ranging from 1 to 2;
each c represents, independently of the others, an integer ranging from 1 to 5;
each d represents, independently of the others, an integer ranging from 1 to 10;
each e represents, independently of the others, an integer ranging from 1 to 4;
each f represents, independently of the others, an integer ranging from 1 to 10; and
each Ar represents, independently of the others, an optionally substituted monocyclic or polycyclic cycloalkylene, cycloheteroalkynene, arylene or heteroarylene group.

3. The reagent of claim 2 in which each Ar is, independently of the others, a group derived from cyclohexane, piperazine, benzene, napthalene, phenol, furan, pyridine, piperidine, imidazole, pyrrolidine or oxadizole.

4. The reagent of claim 1 which is a compound according to structural formula (VII.1):

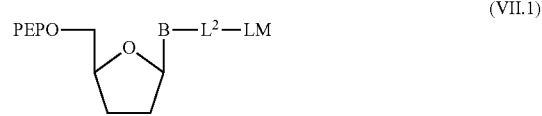

(VII.1)

wherein B represents a suitably protected nucleobase and $L^2$ represents a linker linking nucleobase B to label moiety LM.

5. The reagent of claim 4 in which the nucleobase is selected from adenine, 7-deazaguanine, guanine, 7-deazaguanine, cytosine, uracil, thymine, inosine, xanthene and hypoxanthene.

6. The reagent of claim 4 in which B is selected from $A^{iBu}$, $A^{Pac}$, $C^{Ac}$, $G^{iPr-Pac}$, T and U.

7. The reagent of claim 4 in which $L^2$ is selected from —C≡C—CH₂—NH—, —C≡C—C(O)—, —CH═CH—NH—, —CH═CH—C(O)—, —C≡C—CH₂—NH—C(O)—(CH₂)₁₋₆—NH—, —CH═CH—C(O)—NH—(CH₂)₁₋₆—NH—C(O)—, —C≡CH—CH₂—O—CH₂CH₂—[O—CH₂CH₂]₀₋₆—NH—, —C≡C—C≡C—CH₂—O—CH₂CH₂—[O—CH₂CH₂]₀₋₆—NH—, —C≡C—(Ar)₁₋₂—C≡C—CH₂—O—CH₂CH₂—[O—CH₂CH₂]₀₋₆—NH—, —C≡C—(Ar)₁₋₂—O—CH₂CH₂—[O—CH₂CH₂]₀₋₆—NH— and —C≡C—(Ar)₁₋₂—O—CH₂CH₂—[O—CH₂CH₂]₀₋₆—NH—, where Ar is as defined in claim 2.

8. The reagent of claim 4 in which —B-L²- is selected from

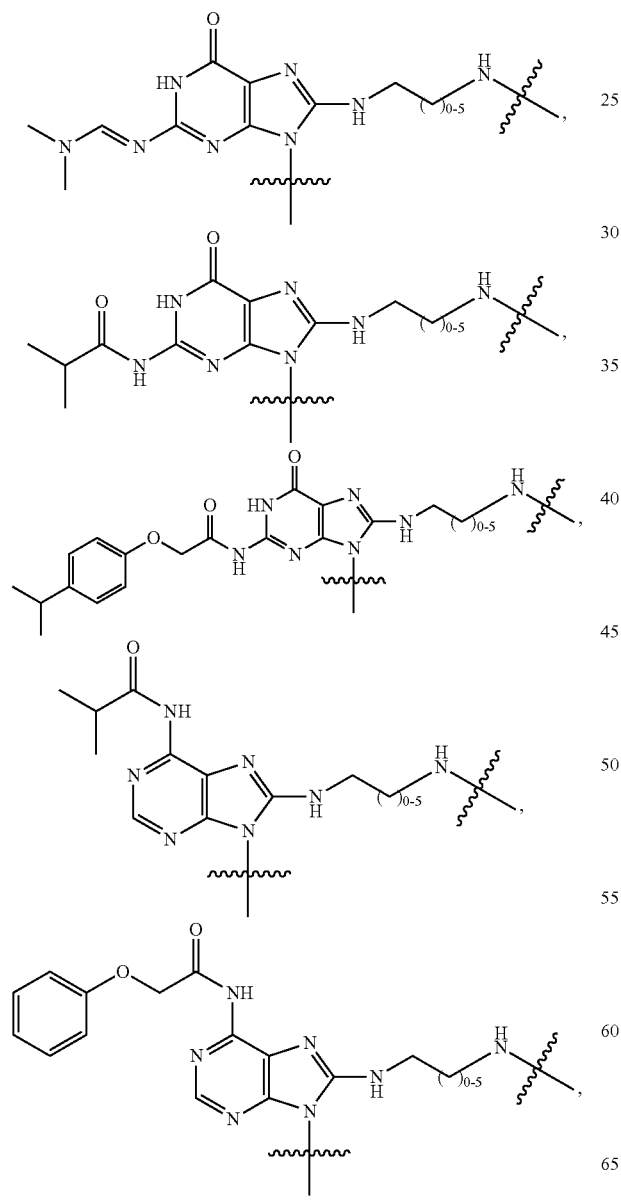

-continued

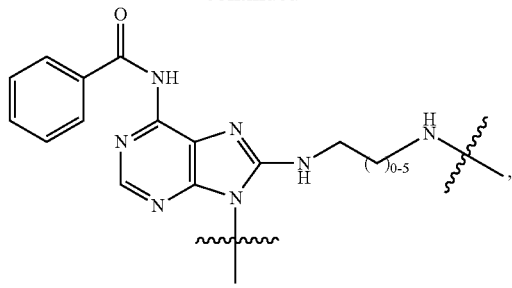

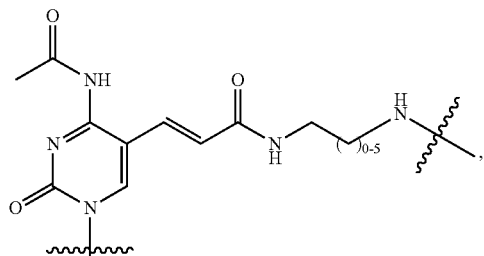

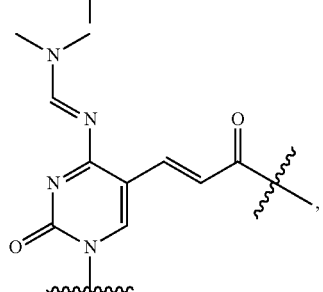

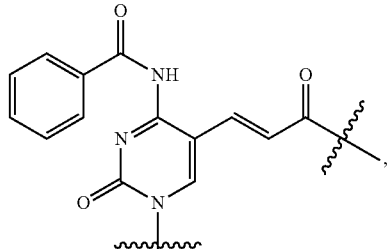

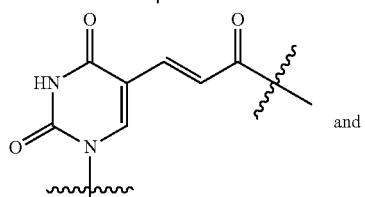

and

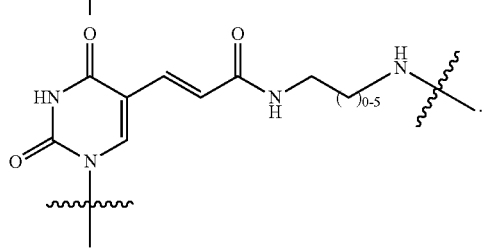

9. The reagent of claim 1 further comprising a suitably protected synthesis handle.

10. The reagent of claim 9 which is a compound according to structural formula (VIII):

R$^e$O-L-LM-L-PEP    (VIII)

wherein R$^e$ represents an acid-labile protecting group, each L represents, independently of the other, an optional linker, LM represents the label moiety and PEP represents the phosphate ester precursor group.

11. The reagent of claim 9 which is a compound according to structural formula (IX):

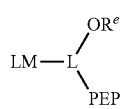
(IX)

wherein LM represents the label moiety, L represents a linker, R$^e$ represents an acid-labile protecting group and PEP represents the phosphate ester precursor group.

12. The reagent of claim 1 in which the phosphate ester precursor group comprises a phosphoramidite of the formula (P.1):

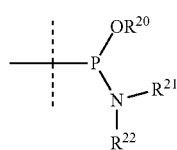
(P.1)

wherein:
- R$^{20}$ is selected from a linear, branched or cyclic saturated or unsaturated alkyl containing from 1 to 10 carbon atoms, 2-cyanoethyl, an aryl containing from 6 to 10 ring carbon atoms and an arylalkyl containing from 6 to 10 ring carbon atoms and from 1 to 10 alkylene carbon atoms; and
- R$^{21}$ and R$^{22}$ are each, independently of one another, selected from a linear, branched or cyclic, saturated or unsaturated alkyl containing from 1 to 10 carbon atoms, an aryl containing from 6 to 10 ring carbon atoms and an arylalkyl containing from 6 to 10 ring carbon atoms and from 1 to 10 alkylene carbon atoms, or, alternatively, R$^{21}$ and R$^{22}$ are taken together with the nitrogen atom to which they are bonded to form a saturated or unsaturated ring that contains from 5 to 6 ring atoms, one or two of which, in addition to the illustrated nitrogen atom, can be heteroatom selected from O, N and S.

13. The reagent of claim 12 in which R$^{20}$ is beta-cyanoethyl and R$^{21}$ and R$^{22}$ are each isopropyl.

14. The reagent of claim 9 in which the suitably protected synthesis handle comprises 4',4''-dimethoxytrityl.

15. The reagent of claim 1 in which the N-protected NH-rhodamine moiety comprises a structure selected from structural formulae (IIIa.1), (IIIa.2), (IIIb 0.1), (IIIb 0.2), (IIIc.1) and (IIIc.2):

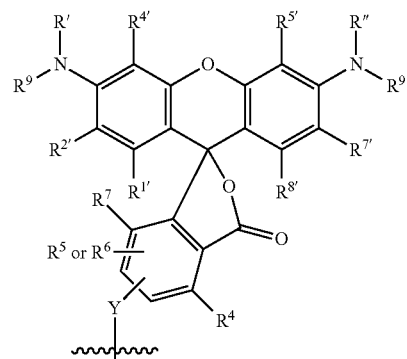
(IIIa.1)

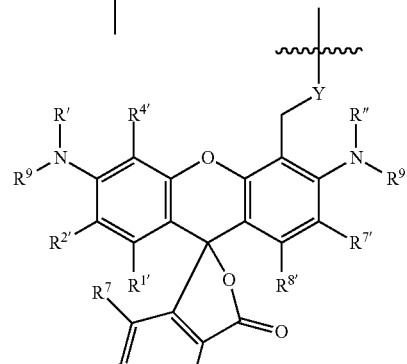
(IIIa.2)

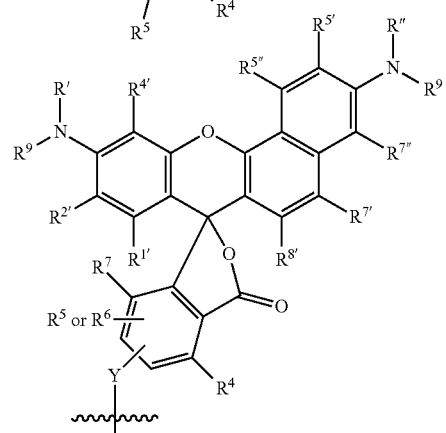
(IIIb.1)

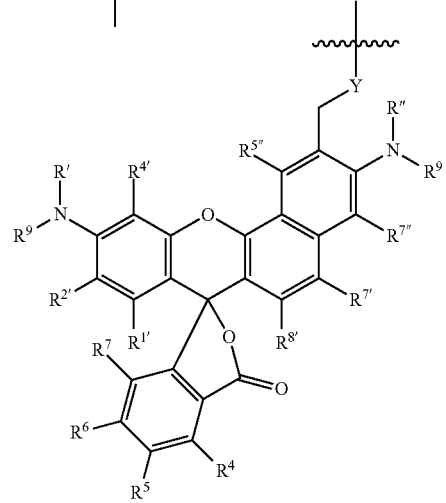
(IIIb.2)

-continued

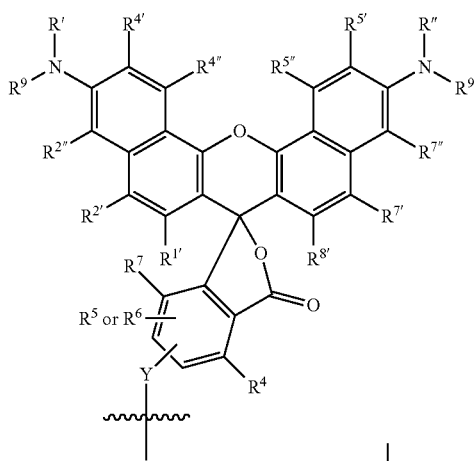

(IIIc.1)

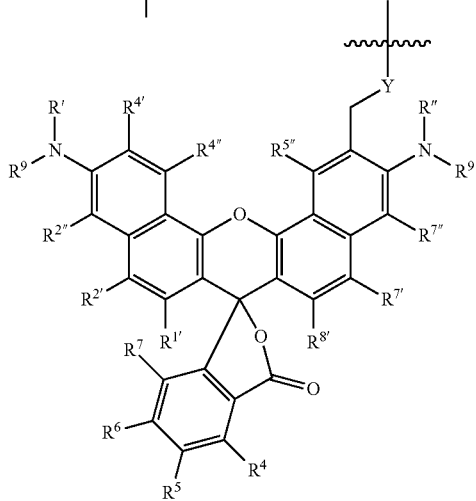

(IIIc.2)

wherein R', R", R$^{2'}$, R$^{2''}$, R$^{3'}$, R$^{4'}$, R$^{4''}$, R$^{5'}$, R$^{5''}$, R$^{6'}$, R$^{7'}$, R$^{7''}$, R$^{8'}$, R$^4$, R$^5$, R$^6$, R$^7$, R$^9$ and Y are as previously defined in claim 1.

16. The reagent of claim 15 in which the N-protected NH-rhodamine moiety has one or more applicable features selected from:

(i) Y is selected from —C(O)—, —S(O)$_2$—, —S— and —NH—;

(ii) R$^4$ and R$^7$ are each chloro;

(iii) R$^{1'}$ and R$^{8'}$ are each hydrogen;

(iv) R$^{1'}$ and R$^{2'}$ or R$^{7'}$ and R$^{8'}$ are taken together to form a benzo group;

(v) R$^{2'}$ and R$^{7'}$ are each hydrogen or lower alkyl;

(vi) R' is R$^{3'}$ and R" is R$^{6'}$; and (vii) R' is R$^{3'}$, R" is R$^{6'}$, and R$^{3'}$ and R$^{6'}$ are taken together with a substituent group on an adjacent carbon atom to form a group selected from —CH$_2$CH$_2$—, —CH$_2$CH$_2$CH$_2$—, —C(CH$_3$)$_2$CH=C(CH$_3$)—, —C(CH$_3$)$_2$CH=CH—, —CH$_2$—C(CH$_3$)$_2$— and

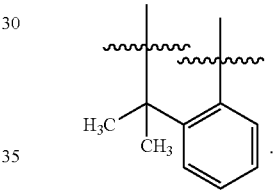

\* \* \* \* \*

UNITED STATES PATENT AND TRADEMARK OFFICE
CERTIFICATE OF CORRECTION

PATENT NO. : 9,783,560 B2
APPLICATION NO. : 14/702499
DATED : October 10, 2017
INVENTOR(S) : Scott C. Benson et al.

Page 1 of 1

It is certified that error appears in the above-identified patent and that said Letters Patent is hereby corrected as shown below:

In the Claims

In Claim 1, Column 71, Line 57, delete "$R^e$" and insert --$R^c$--

In Claim 6, Column 73, Line 5, delete "claim 4" and insert --claim 5--

In Claim 15, Column 78, Line 1, insert --$R^1$-- between "R'" and "$R^2$"

Signed and Sealed this
Fifth Day of December, 2017

Joseph Matal
*Performing the Functions and Duties of the*
*Under Secretary of Commerce for Intellectual Property and*
*Director of the United States Patent and Trademark Office*